US008486617B2

(12) United States Patent
Ho et al.

(10) Patent No.: US 8,486,617 B2
(45) Date of Patent: Jul. 16, 2013

(54) METHODS FOR PREPARING FREEZE-DRIED PLATELETS, COMPOSITIONS COMPRISING FREEZE-DRIED PLATELETS, AND METHODS OF USE

(75) Inventors: David Ho, McLean, VA (US); Cindy S. Orser, McLean, VA (US); Alan S. Rudolph, Potomac, MD (US); Keith Moskowitz, Germantown, MD (US); Joshua Dee, Germantown, MD (US)

(73) Assignee: Cellphirc, Inc, Rockville, MD (US)

( * ) Notice: Subject to any disclaimer, the term of this patent is extended or adjusted under 35 U.S.C. 154(b) by 616 days.

(21) Appl. No.: 11/659,708

(22) PCT Filed: Aug. 12, 2005

(86) PCT No.: PCT/US2005/028559
§ 371 (c)(1),
(2), (4) Date: Apr. 18, 2007

(87) PCT Pub. No.: WO2006/020773
PCT Pub. Date: Feb. 23, 2006

(65) Prior Publication Data
US 2007/0243178 A1 Oct. 18, 2007

Related U.S. Application Data

(60) Provisional application No. 60/600,838, filed on Aug. 12, 2004, provisional application No. 60/619,930, filed on Oct. 20, 2004.

(51) Int. Cl.
*A01N 1/02* (2006.01)
*A01N 63/00* (2006.01)

(52) U.S. Cl.
USPC .......................................... 435/2; 424/93.72

(58) Field of Classification Search
None
See application file for complete search history.

(56) References Cited

U.S. PATENT DOCUMENTS

| | | | |
|---|---|---|---|
| 5,656,498 | A | 8/1997 | Iijima et al. |
| 5,736,313 | A | 4/1998 | Spargo et al. |
| 5,993,804 | A | 11/1999 | Read et al. |
| 6,221,575 | B1 | 4/2001 | Roser et al. |
| 7,169,606 | B2 | 1/2007 | DePablo et al. |
| 2003/0022333 | A1 | 1/2003 | Bronshtein |
| 2005/0074402 | A1 | 4/2005 | Cagnolini et al. |

FOREIGN PATENT DOCUMENTS

| | | |
|---|---|---|
| JP | 09-109136 | 4/1996 |
| WO | 91/17655 | 11/1991 |
| WO | 98/34478 | 8/1998 |
| WO | WO 01/58266 | 8/2001 |
| WO | 03/014305 | 2/2003 |
| WO | WO 2004/050896 | 6/2004 |

OTHER PUBLICATIONS

"Platelet." The American Heritage® Dictionary of the English Language, Fourth Edition. Houghton Mifflin Company, 2004. Mar. 23, 2010. <Dictionary.com http://dictionary.reference.com/browse/platelet>.*
Merten et al., "Platelet Microparticles Promote Platelet Interaction with Subendothelial Matrix in a Glycoprotein IIb/IIIa Dependent Mechanism", Circulation 99 :2577-2582 (1999).*
"Cryoprotein." Merriam-Webster's Medical Dictionary. Merriam-Webster, Inc. Mar. 24, 2010. <Dictionary.com http://dictionary.reference.com/browse/cryoprotein>.*
"Cryoprotein." The American Heritage® Stedman's Medical Dictionary. Houghton Mifflin Company. Mar. 24, 2010. <Dictionary.com http://dictionary.reference.com/browse/cryoprotein>.*
Diener "Antiplatelet agents and randomized trials", Review in Neurological Diseases 4 (4) : 177-83 (2007), abstract only.*
Galila Agam et al. "Passive Participation of Fixed Platelets in Aggregation Facilitated by Covalently Bound Fibrinogen" Blood 61:1 (Jan. 1983) pp. 186-191.
Thomas Fischer et al. "Primary and secondary hemostatic functionalities of rehydrated, lyophilized platelets" Transfusion V46 (Nov. 2006) pp. 1943-1950.
C.R. Valeri et al. "Survival of baboon biotin-X-N-hydroxysuccinimide and In-oxine-labelled autologous fresh and lyophilized reconstituted . . ." Vox Sanguinis (2005) 88, 122-129.
Strong, D.M., Transfusion Medicine Bulletin, Vo. 2, No. 2, Jul. 1999.
Wolkers, W.F. et al., "Human Platelets Loaded with Trehalose Survive Freeze-Drying", *Cryobiology* 42:79-87, 2001.
International Search Report, PCT/US05/28559, Apr. 2007.
Office Action, European Patent Application No. EP 05 78 4165; Jul. 2008.
Decision to Grant, European Patent Application No. EP 05 78 4165; Dec. 2009.
Office Action, Chinese Patent Application No. 2005800348733, Feb. 2009.
Decision to Grant, Chinese Patent Application No. 2005800348733, Jan. 2010.
Examination Report, New Zealand Patent Application No. 553389, Jul. 2008.
Notice of Acceptance, New Zealand Patent Application No. 553389, Oct. 2009.
Japanese Office action that issued with respect to patent family member Japan Patent Application No. 2007-525791, mail date Aug. 23, 2011.
Office Action in corresponding Canadian patent application No. 2,557,068, mailed Jul. 2011.
Office Action in corresponding Canadian patent application No. 2,557,068, mailed May 2012.

(Continued)

Primary Examiner — Sandra Saucier
(74) Attorney, Agent, or Firm — Latimer IP Law, LLC

(57) ABSTRACT

The present invention provides processes for preparing freeze-dried platelets, freeze-dried platelets made by those processes, platelets reconstituted from those freeze-dried platelets, methods of using the platelets for therapeutic, diagnostic, and research purposes, and kits comprising the freeze-dried platelets.

15 Claims, 47 Drawing Sheets

OTHER PUBLICATIONS

First Examiner's Report in corresponding Australian patent application No. 2005272821, mailed May 2010.

Notice of Acceptance in corresponding Australian patent application No. 2005272821, mailed Aug. 2010.

Notice of Allowance in corresponding Japanese patent application No. 2007-525791, mailed Oct. 2012.

Funheer, R., et al., "Platelet activation during preparation of platelet concentrates: a comparison of the platelet-rich plasma and the buffy coat methods", Transfusion, vol. 30, No. 7, pp. 634-638, 1990.

* cited by examiner

Figure 41B
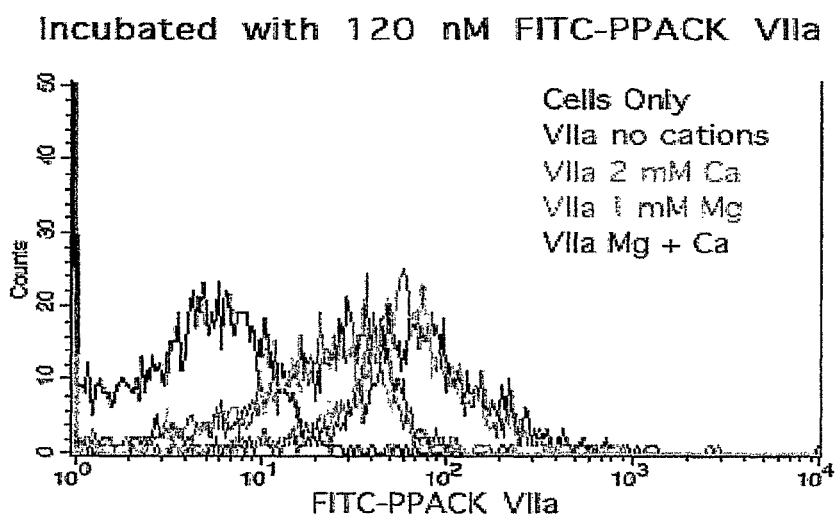
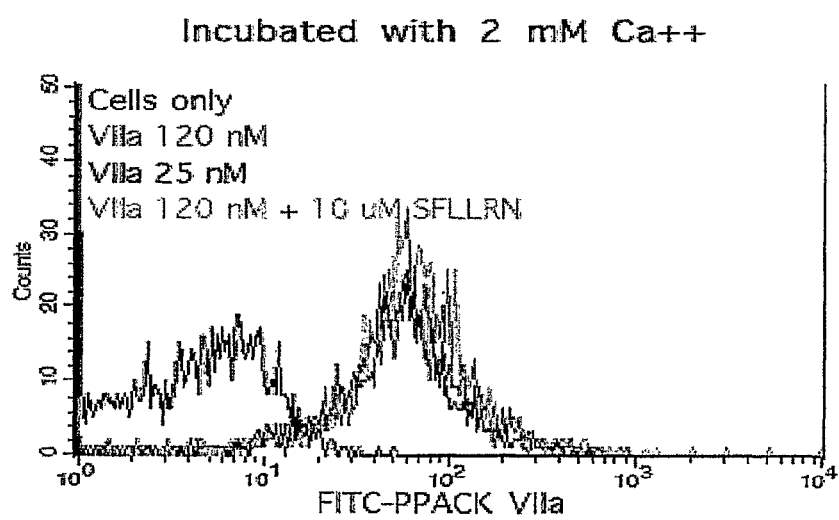
Figure 41C

METHODS FOR PREPARING FREEZE-DRIED PLATELETS, COMPOSITIONS COMPRISING FREEZE-DRIED PLATELETS, AND METHODS OF USE

CROSS-REFERENCE TO RELATED APPLICATIONS

The present application relies on the disclosure of, and claims the benefit of the filing date of the following patent applications, the entire disclosures of all of which are hereby incorporated herein by reference: U.S. provisional patent application No. 60/600,838, filed on 12 Aug. 2004; and U.S. provisional patent application No. 60/619,930, filed on 20 Oct. 2004.

BACKGROUND OF THE INVENTION

1. Field of the Invention

The present invention relates to the field of blood and blood products. More specifically, it relates to platelets and platelet compositions, particularly those containing freeze-dried platelets or rehydrated freeze-dried platelets, that are useful for therapeutic, diagnostic, and research purposes.

2. Description of Related Art

Blood is a complex mixture of numerous components. In general, blood can be described as comprising four main parts: red blood cells, white blood cells, platelets, and plasma. The first three are cellular or cell-like components, whereas the fourth (plasma) is a liquid component comprising a wide and variable mixture of salts, proteins, and other factors necessary for numerous bodily functions. The components of blood can be separated from each other by centrifugation. Typically, centrifugation results in a large volume/mass of the dense red blood cells migrating to the bottom of the centrifuge tube. Above the red blood cells, one will find a relatively thin layer of white blood cells and platelets, which is known as the "buffy coat", due to its whitish grey color. Above the buffy coat is the liquid plasma fraction.

Red blood cells, which are also commonly referred to as erythrocytes, are responsible for carrying oxygen from the lungs to cells for use in cellular processes, and waste carbon dioxide from cells to the lungs for excretion. Red blood cells do not have a nucleus, and are thus short lived cellular components of blood that are constantly being replaced in healthy individuals. The percentage of blood volume composed of red blood cells is called the hematocrit, and this number is often used to indicate the presence of one or more diseases or disorders of or affecting the blood system. Normal hematocrit values are between 37% and 47% for females, and 40% and 54% for males. Red blood cells are routinely transfused into patients in need of them, such as those with chronic anemia or who have sustained an injury or trauma or who have undergone surgery, which resulted in blood loss. In addition, red blood cells are often used to treat anemia caused by any number of diseases or disorders.

White blood cells, which are also commonly referred to as leukocytes, are nucleated cells that are responsible for protecting the body from damage caused by foreign substances. As a general rule, white blood cells function to combat pathogenic organisms, such as bacteria, fungi, and viruses, or substances that might be detrimental to the body, such as protein toxins. However, in certain individuals, white blood cells mount a protective response against apparently harmless substances, such as pollen, resulting in allergic reactions. Indeed, in some cases, white blood cells inappropriately react against a body's own cells or proteins, resulting in autoimmune diseases and destruction of body tissues, which can, in certain circumstances, be fatal. Among other things, purified white blood cells have found use in treating patients who are unresponsive to antibiotic therapy.

Platelets, which are also commonly referred to as thrombocytes, are small, irregularly-shaped megakaryocyte-derived components of blood that are formed in the bone marrow and are involved in the clotting process, and thus aid in protecting the body from excessive blood loss due not only to trauma or injury, but to normal physiological activity as well. Indeed, platelets are crucial in normal hemostasis, providing the first line of defense against blood escaping from injured blood vessels. Platelets generally function by adhering to the lining of blood vessels and interacting with components of the clotting system that are present in plasma or are released by other cellular components of the blood. Purified platelets have found use in treating patients with abnormal platelet function (thrombasthenia) and low platelet count (thrombocytopenia). Concentrated platelets are often used to control bleeding after injury or during acquired platelet function defects, for example those occurring during bypass surgery. The normal circulating platelet count is between 150,000 and 450,000 per microliter (ul) of blood.

When bleeding from a wound suddenly occurs, the platelets gather at the wound and attempt to block the blood flow by forming a clot. There are two general mechanisms to clot formation. In one mechanism, a clot begins to form when the blood is exposed to air. The platelets sense the presence of air and react with fibrinogen to begin forming fibrin. The resulting fibrin forms a web-like mesh that traps blood cells within it. In the other general mechanism, damaged blood vessels release a chemical signal that increases the stickiness of platelets in the area of the injury. The sticky platelets adhere to the damaged area and gradually form a platelet plug. At the same time, the platelets release a series of chemical signals that prompt other factors in the blood to reinforce the platelet plug. Between the platelet and its reinforcements, a sturdy clot is created that acts as a patch while the damaged area heals.

Platelets, in the form of platelet gels, have been used extensively to accelerate wound healing and, in conjunction with autologous fibrin glue, autologous platelet gel has been shown to improve perioperative hemostasis and reduce blood transfusion needs in surgery to replace the ascending aorta (Christenson and Kalangos, 2004). Costasis Surgical Hemostat (Costatis®). A combination of bovine thrombin, bovine collagen, and plasma as the source of fibrinogen and platelets has been shown to work well in the in vivo bleeding rabbit kidney and spleen model (Prior et al., 1999). Nevertheless, other studies have shown that platelet gel, when used alone, is not an effective hemostasis agent (Wajon et al., 2001). Despite of the contradicting findings regarding platelets and their role as hemostasis agents, there is little doubt about the pro-coagulant nature of platelet microparticles; these essential components, often overlooked, are increasingly being recognized as active participants in the in vitro and in vivo clotting process (Nieuwland et al., 1997). When platelets are stimulated with a combination of physiological agonists, such as thrombin and collagen, they release large quantities of microparticles (Sims et al., 1988; Tans et al., 1991). The activated platelets and microparticles express an aminophospholipid, which provides a procoagulant surface to support the formation of activated clotting enzymes in the intrinsic, extrinsic, and common pathways (Rosing et al., 1985).

Compared with activated platelets, microparticles contain a higher density of high-affinity binding sites for activated factor IX (IXa) (Hoffman et al., 1992) and factor Va (Sims et al., 1988). They have a continuous expression of high-affinity binding sites for factor VIII (Gilbert et al., 1991) and support both factor Xa activity (Gilbert et al., 1991; Holme et al., 1995) and prothrombinase activity (Sims et al., 1989).

Aside from the fact that platelet microparticles are important components in the hemostatic response, platelets, in the form of platelet gels, have been used in surgical wound healing applications as well as to treat difficult to heal wounds (Mazzucco et al., 2004). Moreover, the use of platelets in the form of platelet rich plasma has expanded into novel applications, such as bio-tissue engineering or autologous and allogenic tissue grafts, as well as osseous bone integration and soft tissue regeneration (Oikarinen et al., 2003). This is because platelets contain a number of important growth factors within their alpha granules that contribute to the process of hemostasis and wound healing. Studies have found that growth factors, such as platelet derived wound healing factors (PDWHF), platelet-derived growth factor (PDGF), transforming growth factor (TGF), and insulin growth factors (IGF), among others, are important in different stages of the wound-healing cascade and greatly influence mitogenic and cellular differentiation activities (Pierce et al., 1989; Steed, 1997).

These findings have lead to the development of strategies for growth factor replacement. For example, Regranex®, a recombinant human PDGF in a carrier gel, is used to treat diabetic wounds, while others, such as TGF, are currently being tested for FDA approval. Nevertheless, a single growth factor applied into a wound is not as effective as multiple growth factors. This is not surprising since wound healing is a complex integration of cascades that requires multiple growth factors for different stimulatory and inhibitory functions at different phases within the process.

The liquid portion of the blood, which is commonly referred to as plasma, is a complex solution containing various proteins and salts. In general terms, plasma is the substance that remains when red blood cells, white blood cells, and platelets are removed from blood. Due to the presence of numerous proteins in high concentrations, plasma is a straw colored liquid that is unstable at room temperature (i.e., plasma must be stored well below room temperature to protect the proteins present in it from losing activity). The major protein constituents of plasma are: albumin; fibrinogen; antibodies; and numerous proteins necessary for clotting and hemostasis. As can be seen from this brief listing of plasma proteins, plasma serves a variety of functions, from maintaining a satisfactory blood pressure and providing volume to supplying critical proteins for blood clotting and immunity. For example, gamma globulin isolated from plasma can be used to treat patients in need of an antitoxin, and the presence of certain antibodies can be assayed to indicate whether a patient is infected with a certain virus or bacteria. In addition, clotting factor VIII, which can be isolated from plasma, is often used in the treatment of classical congenital hemophilia.

The major functions of blood are to transport oxygen and carbon dioxide and to enable immune system components to quickly and effectively reach all parts of the body to fight off invading microbes. However, because blood is a fluid and needs to be not only retained within the body, but restricted to specific areas of the body (such as blood vessels or other parts of the circulatory system), an important function of blood is to monitor its own distribution within the body, and repair damage that permits the blood to escape from the body or specific areas within the body where it should be retained. The process of monitoring and maintaining blood distribution within its normal boundaries is a balance of the physiological processes that, on the one hand, prevent excessive bleeding after vessel injury (through formation of clots), while on the other hand, maintain a normal blood circulation by keeping the blood in an uncoagulated (i.e., unclotted) fluid state. These seemingly competing processes are part of a complex system that has many control points and feedback loops.

The main process for maintenance of proper blood flow and containment is called hemostasis, which is the process of formation and ultimate degradation of blood clots and the repair of injured tissue. Hemostasis is comprised of four main events: vascular constriction; aggregation of platelets at the site of injury, mediated by fibrinogen, and activation of the platelets by thrombin; creation of a clot (also referred to as a thrombus or fibrin mesh) by platelets and a complex interaction of numerous clotting factors; and, finally, degradation of the clot and repair of the injured tissue.

Blood clotting is a complicated process: if the clot formation is unchecked, the vessel will become occluded; if the clot is not sturdy, excessive blood loss will occur. Therefore, a delicate balance must be maintained for normal hemostasis. In situation where normal hemostasis is unbalanced, clot formation may be compromised. Such an abnormality could be acquired due to ingestion of aspirin or caused by immune dysfunction. The abnormality could also be congenital, such as through genetic diseases and clotting factor defects. For example, defects in the process of hemostasis that lead to bleeding disorders have been identified, and most of such defects are in the enzymes involved in the cascade of activities required for clotting, in platelet activation and function, or in contact activation. Included among these disorders are vWD and hemophilia. Other diseases or disorders of the blood clotting system are a result (i.e., side effect) of treatments for other diseases or disorders. Treatments for such diseases and disorders typically involve reducing the dose of the drug causing the side effect, or discontinuing treatment with the drug.

Blood clotting relies on a complex cascade of enzymatic activities that are tightly controlled through numerous feedback loops and control points. Clotting begins when platelets adhere to the cut wall of an injured blood vessel or other lesion site. In doing so, platelets adhere to collagen that is present on cells at the site of injury, a process that is mediated by a clotting factor known as von Willebrand factor (vWF). vWF is a complex protein that is produced in megakaryocytes and endothelial cells, and stored in platelets or in certain connective tissues. It is often found complexed with Factor VIII, and is known to be necessary for stabilization of Factor VIII in plasma. Defects in quantity and function of vWF are typically genetic in nature, and result in a disease known as von Willebrand disease (vWD).

Adhesion of platelets to the site of injury is mediated by vWf binding to collagen in the subendothelium. Fibrinogen, which exists in plasma as a soluble protein, can bridge activated platelets together in a process termed aggregation or cohesion. Fibrinogen is converted to insoluble strands of fibrin by the enzyme thrombin (which is activated by activated Factor X (Factor Xa)), which also is a potent platelet activating agent. The fibrin, which spontaneously polymerizes into filaments, binds to surface proteins or phospholipids on the platelets to ensnare the platelets in a mesh. The fibrin filaments are then cross-linked through the activity of Factor XIIIa, which is formed from Factor XIII by thrombin. The fibrin-platelet mesh that forms is referred to as a fibrin mesh, thrombus, or clot.

Factor X can be activated by either of two pathways, termed the extrinsic and intrinsic pathways. The intrinsic pathway involves a series of enzymatic reactions that activates various proteases. The process begins with binding of Factor XII to a negatively charged surface, presumably supplied by components of the subendothelium, and activation of Factor XII to Factor XIIa by Kallikrein in a reaction mediated by High Molecular Weight Kininogen (HMWK). Factor XIIa then converts Factor XI to Factor XIa (plasma thromboplastin antecedent). In the presence of calcium ions, Factor XIa converts Factor IX to its activated form, Factor IXa. Factor IXa combines with the non-enzyme protein Factor VIII (antihemophilic globulin or AHG), and in the presence of calcium ions and cell derived phospholipids, activates circulating Factor X to form Factor Xa.

In the extrinsic pathway, which is widely regarded as the primary physiological pathway for initiation of coagulation, the activated form of Factor VII, Factor VIIa, associates with Factor m (tissue thromboplastin), commonly referred to as tissue factor (TF). In the presence of calcium ions, the Factor VIIa/TF complex activates circulating Factor X to form Factor Xa. Factor Xa can also be formed from the action of Factor VII through Factors IX and XI. In this scenario, Factors IX and X can be activated by the combined activities of TF and Factor VIIa. The Factor VIIa/TF complex is recognized as the most potent trigger of the clotting cascade. As discussed above, Factor IXa, in the presence of calcium, phospholipids on the surface of platelets, and Factor VIIIa, activates Factor X to Factor Xa, which then converts prothrombin to thrombin. Thrombin converts soluble fibrinogen to insoluble fibrin fibers to create a mesh.

Thus, Factor X is activated by either the intrinsic or extrinsic activation pathway. Factor Xa, with activated Factor V and in the presence of calcium ions and phospholipids present on the surface of platelets, activates prothrombin to thrombin, which forms fibrin from fibrinogen, leading to formation of a clot. The coagulation of blood is a complex process that involves interaction of a number of components, including fibrinogen, thrombin, Factor VII, Factor VIII, Factor IX, Factor X, Factor XI, and Factor XII. The loss of one of these components invariably leads to a clinical presentation of a blood disorder, which can be life-threatening for some patients.

Defects in the process of hemostasis that lead to bleeding disorders have been identified, and most of such defects are in the enzymes involved in the cascade of activities required for clotting, in platelet activation and function, or in contact activation. Included among these disorders are vWD and hemophilia. Various treatments for these two disorders are known, most of which rely on supplying one or more of the clotting factors mentioned above.

Congenital Hemophilia is classified in three different groups: classical hemophilia or Hemophilia A (FVIII deficiency); Christmas disease or Hemophilia B (FIX deficiency); and Hemophilia C (FXI deficiency). Hemophilia is recognized as a disorder in which bleeding is not stopped within the normal amount of time. That is, hemophiliacs do not bleed more profusely or more quickly, they bleed for a longer period of time. Approximately 20,000 Americans have hemophilia. The vast majority of cases are either Hemophilia A or B, with Hemophilia A accounting for about 80 percent of all hemophilia cases. Hemophilia C is rare, occurring in approximately one in 100,000 Americans.

Hemophilia A is an X-linked disorder resulting from a deficiency of Factor VIII, and is defined as the absence or less than normal levels of Coagulation Factor VIII. Hemophilia A arises from a variety of mutations in the gene for Factor VIII. Current treatment of Hemophilia A involves infusion of Factor VIII concentrates or concentrates of complexes of Factor VIII and vWF prepared either from human plasma or by recombinant DNA technology. In contrast to Hemophilia A, Hemophilia B results from deficiencies in Factor IX. Current treatment of Hemophilia B involves infusion of plasma-derived or recombinant Factor IX concentrates. Finally, Hemophilia C results from deficiencies in Factor XI.

Due to continuing concerns about the safety of the public blood supply and emerging diseases that are transmissible through blood and blood products, the source of choice for Factor VIII has become a recombinantly produced form. Recombinant Factor IX has been approved for human use (Benefix®, Genetics Institute) and will likely become the source of choice. In addition, gene therapy has been proposed as a treatment or cure for hemophilia. However, to date, transgenic approaches for the treatment of hemophiliacs have not resulted in long term stable expression of coagulation factors, have encountered unanticipated mortality issues, and still may result in inhibitor production in recipients (discussed below).

Treatment of hemophilia with concentrates of Factor VIII causes, in about 15% to about 30% of patients with Hemophilia A, and in about 3% of patients with Hemophilia B, production of antibodies against the introduced Factor VIII or IX, respectively. Although recombinant Factor VIII appears to cause this response in only about 5% of patients with Hemophilia A, it is still a significant problem in the treatment of this disorder. This process and the resulting disorder are referred to as "Hemophilia with Inhibitors", often described as the induction of antibodies to transfused proteins normally used to treat a missing clotting factor. In contrast, Acquired Hemophilia is the development of inhibitors in persons containing normal levels of coagulation proteins. Acquired Hemophilia is therefore a pseudo-autoimmune disease, and can occur in otherwise normal non-hemophilia individuals who are treated with products containing factors involved in clotting. In general, the antibodies that are generated react with the Factor VIII that is administered, and result in inhibition of the Factor VIII activity, thus rendering the treatment useless in patients lacking endogenous Factor VIII, and ironically rendering the treatment harmful in patients who originally possessed a low, but insufficient, level or activity of endogenous Factor VIII.

Numerous ways of avoiding Acquired Hemophilia and Hemophilia with Inhibitors have been proposed and implemented. For example, rather than treating with exogenous Factor VIII, another strategy to treat Hemophilia A is to administer exogenous Factor VIIa, thus eliminating the need for Factor VIII for hemostasis. Likewise, treating with excessive amounts of Factor VIII and with anti-idiotype anti-Factor VIII antibodies have been tested. Other approaches include using FEIBA bypassing agents, Prothrombin Complex Concentrates, Recombinant Factor VIIa, Porcine Factor VIII, infusion of high dose intravenous Immunoglobulin, Immune Tolerance Therapy (ITT), and plasmapheresis either with or without Protein A adsorption to remove the inhibiting antibodies.

Furthermore, treatment with purified recombinant Factor VIIa has become common. For example, dosages of 10 to 15 ug/kg, and even as high as 150 ug/kg, a range that can provide a circulating level of Factor VIIa of about 0.2 to 2.0 ug/ml blood, of Factor VIIa have been found to be safe and effective in some Hemophilia A patients with inhibitors. These doses are quite high compared to the normal estimated concentration of Factor VIIa, which is about 0.005 ug/ml blood. Although these methods have seen success, none of the current methods are completely effective, and all are quite expensive. Furthermore, at least 5-10% of patients receiving recombinant FVIIa therapy fail to achieve hemostasis.

In addition, Type III or severe von Willebrand Disease often presents clinically as Hemophilia A. Factor VIII is normally transported and protected from plasma proteases by vWf. In the absence of circulating vWf, the endogenous Factor VIII is rapidly degraded and cleared from circulation, resulting in symptoms of Hemophilia A. Treatments for vWD vary depending upon the nature and severity of the disease. Treatments include DDAVP therapy, either by injection or through the nasal passage. The DDAVP therapy acts by releasing endothelial cell vWf to the circulation. Treatments also include plasma cryoprecipitate, which provides a concentrated form of vWf and other clotting factors.

Traditional treatment of hemophilia typically occurs only after bleeding symptoms are recognized. More recent treatment regimens have been developed in which periodic prophylactic infusion of missing clotting factors is performed, regardless of bleeding status at the time. This approach maintains the factor level high enough that bleeding, joint destruction, and life-threatening hemorrhage are minimized and almost entirely avoided. While highly effective, this therapy regimen is quite expensive.

Platelet functionality is another critical component of blood clots. Dysfunctional platelets may lead to abnormal hemorrhage, such as bleeding or thrombosis. Thus platelet function assays are an integral part of the diagnosis and monitoring of blood related diseases. For example, acquired platelet defects, such as ingestion of aspirin, cardiac disease, renal disease, or congenital platelet defects such as Bernard-Soulier syndrome, Glanzmann's thrombasthenia and storage pool disease, to name a few, can influence the normal hemostatic function of the platelets. To assess the platelet function, at the very minimal, a complete blood count with a peripheral blood smear will provide some basic information. Other tests, such as bleeding time, platelet function tests using an aggregometer to assess the aggregation of platelets to a panel of platelet agonists performed on whole blood or platelet rich plasma will classify the defect. However, such analyses, although accurate, are not highly sensitive, and can fail to detect slight perturbances in normal clotting function at early stages of a disorder. Likewise, determination of the precise point of failure of the blood clotting cascade may require numerous assays using freshly drawn blood.

Although it is known that platelets are involved in the clotting process and are the source of at least one clotting factor, to date, there is no disclosure of the use of resting, activated, fixed, frozen, or lyophilized platelets, or any combination of these, for the treatment of Acquired or Congenital Hemophilia or for treatment of persons with bleeding disorders who have normal platelet counts and platelet functions. Kirby & Gregoriadis (1984) prepared liposomes containing Factor VIII in an attempt at oral treatment of hemophilia. Later, Giles et al. (1988) showed a combination of Factor Xa and phosphatidylcholine-phosphatidylserine vesicles bypassed Factor VIII in vivo, while Hong & Giles (1992) demonstrated the normalization of the hemostatic plugs of dogs with Hemophilia A (Factor VIII deficiency) following the infusion of a combination of Factor Xa and phosphatidylcholine-phosphatidylserine vesicles. More recently, Yarovoi et al. (2003), using a transgenic approach, demonstrated that Factor VIII ectopically expressed in platelets showed efficacy in Hemophilia A treatment in a mouse model. Further, Hrachovinova et al. (2003) showed that the interaction of P-selectin and PSGL1 generates leukocyte-derived micro particles that correct hemostasis in a mouse model of Hemophilia A. However, none of these researchers used or proposed using normal platelets or platelet derivatives to treat hemophilia.

Typically, detection of a blood clotting disease or disorder involves analyzing the patient's blood for platelet counts, various markers involved in blood clotting, and clot-forming ability. The coagulation assays measured the activated clotting time (ACT), the prothrombin time (PT), the plasma thrombin time (PTT), and the activated partial thromboplatin time (APTT) are used to evaluate the intrinsic and extrinsic coagulation pathways. These assays are generally performed in the laboratory and analysis often requires multiple samples of blood to be drawn from the patients. Moreover, these assays are potentially unreliable as they are end-point tests in which results are based on the time of clot formation in vitro. Another limitation relates to the fact that exogenous reagents, such as kaolin, thrombin, calcium, etc. must be added thus, the results are based on an artificial system, and do not necessarily reflect the patent's thrombotic potential.

As discussed above, a critical function of the blood clotting system is to stop blood loss from injured tissues, such as tissues that have been damaged by wounds, surgery, or other trauma. However, sometimes the wound or trauma is so great that the blood system of the injured person is unable to rapidly and effectively stop all of the bleeding. Furthermore, while the clotting function is provided satisfactorily in most persons, in some persons the clotting system is impaired such that adequate clotting is not provided and extensive, sometimes deadly bleeding occurs as a result of injury or trauma. Thus, there are often times where a person is in need of additional platelets to provide the clotting function that is missing or inadequate.

In addition to their use "as is" to supply blood clotting functions to persons in need, platelets are studied extensively in the laboratory to characterize their properties and understand their precise role in the blood clotting cascade. Research on platelets provides information on blood clotting factors that are provided by the platelets, factors that interact with the platelets to promote clotting and wound healing, and factors that are necessary to activate platelets or otherwise attract the platelets to, and retain them at, a site of injury.

Both the therapeutic and research uses for platelets require that platelets be available in a form that is biologically active. Currently, platelets for therapeutic uses (e.g., infusion for wound healing) are typically provided as freshly isolated products, which are less than five days old. As can be immediately recognized, maintaining an adequate supply of fresh platelets for use by patients in need is costly and results in loss of a large amount of supplies due to expiration prior to use. Furthermore, because fresh platelets are so important for use in therapy, it is difficult and expensive to obtain those platelets for research purposes. Thus, there is a need in the art for alternatives to fresh platelets for therapy and research.

U.S. Pat. No. 5,622,867 to Livesey et al. discloses a system for cryoprotecting platelets for storage. The system treats fresh platelets with an inhibitor system comprising second messenger effectors. Inhibitors of one or more of the following pathways are added: cAMP, sodium channel, cGMP, cyclooxygenase, lipoxygenase, phospholipase, calcium, proteinase and proteinase, and membrane modification. A cryoprotectant, such as DMSO, maltodextrin, dextran, hydroxyethyl starch, and glucose, is also added where the platelets are to be maintained at low temperatures. Prior to use, the platelets are washed to remove the inhibitors and cryoprotectant.

U.S. Pat. No. 5,656,498 to Iijima et al. discloses freeze-dried platelets and methods of making them. The method comprises pre-treating platelets in blood plasma with a solution containing a saccharide, a biopolymer, an acid, or an acid salt, granulating the treated plasma, rapidly cooling the granules, and freeze-drying the granules.

U.S. Pat. No. 5,736,313 to Spargo et al. discloses freeze-dried platelets and a process for making them. The process of making the freeze-dried platelets comprises pre-incubating the platelets in a phosphate-citrate buffer or a phosphate-phosphate-citrate buffer, both of which contain a carbohydrate (e.g., glucose). After pre-incubation, the platelets are loaded with a carbohydrate, then suspended in a lyophilization buffer containing a matrix-forming polymer and a carbohydrate. The platelets are then slowly cooled to about −50° C. while the pressure is reduced to a vacuum state.

U.S. Pat. Nos. 5,958,670 and 5,800,978, both to Goodrich et al., also disclose freeze-dried platelets and methods of making them. The inventions disclosed in these patents rely on use of compositions having glass transition temperatures of above about −60° C. The compositions generally comprise a component that is permeable to the platelets (e.g., a carbohydrate, such as a sugar) and a component that is impermeable to the platelets (e.g., gelatin, PEG). To create the freeze-dried platelets, the temperature of the composition is reduced to a point below the glass transition temperature of the composition, and vacuum evaporating or subliming the liquid from the composition. An earlier patent, U.S. Pat. No. 5,213,814, also to Goodrich et al., discloses stabilized platelets and methods of making them. The methods and platelets are suitable for storage of the platelets for extended periods of time at about 4° C. The methods generally comprise immersing platelets in a buffered aqueous solution containing a carbohydrate and a biologically compatible polymer or mixture of polymers, then freezing the solution and drying the frozen solution to produce freeze-dried platelets containing less than 10% by weight of moisture.

U.S. Pat. Nos. 6,127,111 and 6,372,423, both to Braun, disclose freeze-dried platelets and methods of making them. The methods of making the freeze-dried platelets comprise exposing the platelets to a coagulation inhibitor (e.g., EDTA or citrate) and a "cake forming agent" (e.g., a protein such as serum albumin, or a polysaccharide such as mannitol) for about 5 to 60 minutes at room temperature, then freeze-dried to reduce the moisture content to below 10%.

Investigators at the University of California, Davis, have developed a process for making freeze-dried platelets. The process comprises loading the platelets with trehalose prior to freeze-drying. In U.S. Pat. No. 6,723,497, a method of preparing freeze-dried platelets is disclosed in which platelets are loaded with trehalose by incubating the platelets at a temperature from about 25° C. to less than about 40° C. with up to 50 mM trehalose, cooling the loaded platelets to below −32° C., and lyophilizing the cooled platelets. Published U.S. patent application 2005/0048460 discloses a method for making freeze-dried platelets that includes exposing the platelets to a carbohydrate (e.g., trehalose) and an amphiphilic agent (e.g., arbutin), and freeze-drying the platelets. See, for example, U.S. Pat. Nos. 6,770,478, 6,723,497, 5,827,741, and U.S. published patent applications Nos. 2005/0048460, 2004/0152964, 2004/0147024, and 2004/0136974.

U.S. Pat. No. 6,833,236 to Stienstra discloses a method for the production of stabilized platelets, and platelets made by the method. The method comprises pre-activating the platelets, for example by exposing them to stress, to induce formation of microvesicles, contacting the pre-activated platelets with a carbohydrate to introduce the carbohydrate into the platelets, and drying the loaded platelets.

Even though numerous advances in blood products and wound healing have taken place over the last several years, there is still a need for improved compositions for treating wounds, such as by hemostasis or clotting of wounds. There is accordingly a need for improved methods of making compositions for treating wounds. Likewise, there is a need for methods of treating wounds to stop blood loss that are rapid, effective, and suitable for use in multiple settings. Furthermore, there is still a need for improved diagnostic assays for bleeding diseases and disorders.

SUMMARY OF THE INVENTION

The current invention addresses needs in the art by providing platelets, platelet microparticles, and compositions comprising platelets and/or platelet microparticles. The platelets, microparticles, and/or compositions can be used for numerous purposes, including, but not limited to, use as hemostats, use to form clots at sites of injury involving bleeding, and use to promote tissue regeneration and healing. They also can be used for treating hemophilia, including Hemophilia A, Hemophilia B, Hemophilia C, and Acquired Hemophilia with Inhibitors. It also provides compositions and methods for prophylactically preventing or treating active excessive bleeding associated with anticoagulant therapy or other therapies or environmental effects that result in inhibition of the clotting cascade. The current invention also addresses needs in the art by providing compositions and methods that can be used as diagnostics for detection of blood clotting disorders. Accordingly, the present invention provides methods of making diagnostic compositions and using them in methods of diagnosing bleeding disorders. The present invention further addresses needs in the art by providing methods for preparing freeze-dried platelets, freeze-dried microparticles, methods of reconstituting or rehydrating freeze-dried platelets, and reconstituted platelets. These methods of the invention provide freeze-dried platelets that are stable for extended periods of time at room temperature or lower. They also provide freeze-dried platelets that, upon reconstitution, function well in the process of blood clotting, and thus can be used successfully in therapeutic applications, such as for wound healing and treatment of bleeding diseases and disorders. Kits are provided to contain the platelets, microparticles, and/or compositions.

In embodiments, the present invention uses platelets and various preparations of platelets and/or microparticles as an active agent to provide normal or pseudo-normal hemostasis properties, such as to hemophiliacs, and to provide hemostatic properties to hemophiliacs and others who have experience traumas resulting in bleeding. The invention further provides freeze-dried (lyophilized) trehalose stabilized platelet derivatives for the treatment of drug-induced coagulopathy, and for the accelerated efficacy of procoagulant drugs in the presence of freeze-dried platelet derivatives. Other non-limiting examples of uses for the platelets, microparticles, and/or compositions include use in diagnostic assays and use in research on platelet function and blood clotting. The platelets, microparticles, and/or compositions can be produced following the methods provided herein. Accordingly, the present invention provides methods of making hemostats and methods of using the hemostats, such as for treating wounds and bleeding.

It has been unexpectedly discovered that platelets or preparations of platelets, such as freeze-dried platelets, can provide normal or almost normal clotting properties, and thus hemostasis properties. They have been found to be suitable for providing these functions to sites of traumatic injury and to the blood of hemophiliacs. Accordingly, they can be used prophylactically to treat hemophilia, whether it be Hemophilia A, Hemophilia B, Hemophilia C, or Acquired Hemophilia. They likewise can provide enhanced clotting properties to blood that is subject to anticoagulant therapy. The discovery, as it relates to bleeding diseases and disorders, is unexpected, at least in part, because diseases and disorders that can be treated with the platelet compositions of the invention typically do not present a clinical symptom of low platelets. That is, blood platelet counts in hemophiliacs, for example, are typically normal, and thus have been generally expected to provide all of the necessary components that platelets typically provide. It is believed that platelets of the invention provide Factor VIII or Factor IX, or one or more essential components that are involved in steps in the clotting cascade that occur before steps involving Factor VIII or Factor IX, and thus overcome these deficiencies in hemophilia. Likewise, the compositions of the invention overcome the deficiencies seen in anticoagulant therapy patients and other subjects showing delayed or absent clotting by providing at least one component in the clotting cascade that is downstream of the component that is lacking in these patients. Because the platelets of the invention are maintained in the body for relatively long periods of time (as compared to small molecule drugs, for example), treatment can be accomplished on a schedule, and need not be performed at the time of an injury, although treatment according to the invention does not exclude such "on demand" treatment.

In a first aspect, the invention provides platelets and compositions comprising platelets. Typically, the platelets and compositions comprise freeze-dried platelets or rehydrated freeze-dried platelets. In general, the compositions also comprise platelet microparticles. The platelets, microparticles, and compositions can be made using methods of the invention. The freeze-dried platelets of the invention are highly stable, having a shelf-life of at least six months. The freeze-dried platelets and rehydrated platelets derived from them retain most, if not all, of the characteristics necessary for blood clotting function of the platelets when introduced into individuals, patients, or subjects (all used interchangeably herein) in need of platelet functions. Thus, the freeze-dried platelets of the invention may be used for both in vivo therapeutic purposes and in vitro diagnostics or research. The platelets, whether freeze-dried or reconstituted, can be used for numerous purposes, including, but not limited to, use as an injectable or infusible substance for treatment of bleeding in a patient, use as a direct treatment for bleeding that is accessible from outside the body. They likewise can be used for diagnostic purposes, such as to diagnose a disorder of the blood clotting system, or for in vitro studies, such as for studies on the blood clotting process. They likewise can be used to monitor the blood clotting ability of a patient's blood clotting system over a period of time, such as, for example, during a treatment regimen for a disease or disorder of the blood clotting system or another system or tissue within the patient's body. The freeze-dried platelets, or rehydrated platelets made from them, can have properties of freshly obtained or in-dated platelets sufficient to provide clotting functions, and promote wound healing. The platelets can be present in any suitable composition, and in any concentration. In various embodiments, they are provided as concentrated platelets from blood or as concentrated platelets from blood that have been freeze-dried and optionally reconstituted. The compositions can comprise other blood components, and in particular can comprise other blood clotting factors in their normal or activated states, such as Factor VII, Factor VIII, or Factor IX.

In another aspect, the invention provides methods of making or preparing (used interchangeably herein) freeze-dried platelets, freeze-dried microparticles, and/or compositions comprising freeze-dried platelets and/or microparticles. The methods generally comprise obtaining platelets, exposing the platelets to at least one saccharide under conditions that are sufficient for the saccharide to be taken into the platelets; adding a cryoprotectant; and lyophilizing. For example, the method can comprise providing platelets, suspending the platelets in a salt buffer that comprises at least one saccharide to make a composition, incubating the composition at a temperature above freezing for at least a sufficient time for the at least one saccharide to come into contact with the platelets, adding a cryoprotectant to make a second composition, and lyophilizing the second composition. The methods can further comprise adding the freeze-dried platelets to other platelets or to plasma, to form a mixture. Freeze-dried platelets according to the present invention, alone or in conjunction with other platelets and plasma, are useful for, among other things, diagnosing various diseases and disorders of the blood clotting system. The freeze-dried platelets can be re-constituted or re-hydrated (used interchangeably herein) by exposure to an aqueous liquid, such as water or an aqueous buffer. Alternatively, the freeze-dried platelet preparations can be used directly in treating a subject or patient (used interchangeably herein), such as one suffering from a bleeding wound or a bleeding disorder. The platelets used to make the freeze-dried platelets or the compositions may be indated (freshly isolated) or outdated (older than permitted by USFDA regulations for therapeutic uses of blood).

In an additional aspect, the invention provides a method of making rehydrated or reconstituted platelets from the freeze-dried platelets of the invention. In general, the method of reconstituting comprises exposing freeze-dried platelets to an aqueous liquid in a sufficient amount and for a sufficient amount of time to rehydrate the platelets such that they regain a normal shape and fluid content. In embodiments, the amount of aqueous liquid is two times the volume of the dried platelets. In embodiments, the amount of aqueous liquid is equal to the volume of the dried platelets. In embodiments, the amount of aqueous liquid is equal to one-half the volume of the dried platelets. In other embodiments, the volume of the aqueous liquid is two times the volume of the composition prior to lyophilization. In other embodiments, the volume of the aqueous liquid is equal to the volume of the composition prior to lyophilization. In yet other embodiments, the volume of the aqueous liquid is one-half the volume of the composition prior to lyophilization.

In yet another aspect, the invention provides rehydrated platelets. The rehydrated platelets of the invention possess all of the characteristics of platelets that are needed for normal blood clotting, when introduced into a subject in need of blood clotting functions. For example, the rehydrated platelets comprise all of the surface molecules necessary to participate in blood clot formation in a subject into which platelets are introduced (i.e., a subject to whom the platelets are administered).

A further aspect of the invention provides kits. In general, a kit of the invention comprises the freeze-dried platelets of the invention. The kits of the invention typically comprise at least one container containing the platelets of the invention, and can further comprise optional components, such as sterile aqueous liquid for rehydrating the platelets, equipment for administering the platelets, and the like. Thus, at its basic level, a kit of the invention is a container comprising platelets, microparticles, or a composition according to the invention. The container can be any material suitable for containing these substances, such as a vial or ampule. In embodiments, the container comprises a sufficient amount of platelets to perform at least one embodiment of at least one method according to the invention. Thus, the kits can be, among other things, diagnostic kits, blood clotting monitoring kits for coagulation proteins or platelets, or drug treatment monitoring kits. In embodiments, the container is provided as a component of a larger kit, which includes suitable packaging and, optionally, instructions and other information relating to use of the compositions. In embodiments, the container or kit comprises other components, such as purified components of the clotting cascade. The kit can be configured to supply the freeze-dried platelets for use in in vivo treatments, for use in in vitro diagnostics, or for use in in vitro or in vivo research. Often, the kits will comprise some or all of the supplies and reagents to perform one or more control reactions to ensure the kits are performing properly and to provide baseline results against which test samples can be compared. In embodiments, platelets are provided in a sufficient amount to treat a subject in need of platelets, such as a patient undergoing surgery or having a bleeding wound. In other embodiments, platelets are provided in a sufficient amount to perform studies on platelets or the blood clotting system of the species of animal from which the platelets originate.

In a further aspect, the present invention provides methods of treating a subject in need, or suspected of being in need, of one or more component of the blood clotting system, such as individuals in need or suspected of being in need of platelets. In general, the methods comprise obtaining freeze-dried platelets (either purified or as part of a composition), and administering them to a subject in need. Administering can be through any known technique, but is typically through infusion, injection, or direct application to a site of bleeding. The methods can comprise the optional step of rehydrating the platelets prior to administering them to the subject. The subject can be any subject in need, such as one that is suffering from a bleeding wound or one who has a bleeding disease or disorder. In various embodiments, the individuals are hemophiliacs or patients who are undergoing treatment with anticoagulant agents. In yet other embodiments, the individuals are patients who have had their clotting system compromised in some other way, such as by liver failure, dialysis, or by exposure to environmental agents. In general, the method of this aspect of the invention comprises administering the composition of the invention to an individual in an amount sufficient to raise the hemostatic properties of that individual's blood to a level that is detectably higher than it was before administration. The method can further comprise administering other biologically active agents, such as clotting factors, and chemotherapeutic agents for treatment of cancer. It can also comprise treatment with physical modalities, such as with radiation. It is envisioned that if fresh, indated platelets are used, one may optionally activate the platelets to provide a better hemostatic benefit towards the treatment of clotting disorders. The freeze-dried platelets, rehydrated platelets, or compositions can be used in conjunction with other hemostatic agents, such as recombinant FVIIa, to enhance the efficacy of the latter at otherwise sub-pharmacologic amounts, thereby saving cost and simplifying administration and treatment.

This aspect of the invention provides a method of treating subjects suffering from congenital or acquired bleeding, such as congenital or acquired Hemophilia with Inhibitors; platelet defect diseases, such as Bernard-Soulier syndrome and Glanzmann thrombasthenia; autoimmune thrombocytopenia, alloimmune thrombocytopenia, drug-induced thrombocytopenia, thrombotic thrombocytopenic purpura, and other platelet-associated disorders. It also provides compositions and methods for prophylactically preventing or treating active excessive bleeding associated with anticoagulant therapy or other therapies or environmental effects that result in inhibition of the clotting cascade.

In yet a further aspect, the invention provides for use of the platelets, microparticles, and compositions as active agents to provide normal or pseudo-normal hemostasis properties to individuals, including but not limited to hemophiliacs, and to provide hemostatic properties to individuals, including but not limited to hemophiliacs, who have experience traumas resulting in bleeding. The invention further provides for use of the platelets, microparticles, and/or compositions for the treatment of drug-induced coagulopathy, and for the accelerated efficacy of procoagulant drugs. Thus, the invention provides for use of the platelets, microparticles, and compositions in conjunction with other hemostatic agents, such as recombinant FVIIa, to enhance the efficacy of the latter at otherwise sub-pharmacologic amounts, thereby saving cost and simplifying administration and treatment.

In another aspect, the present invention provides methods of using the freeze-dried platelets (or reconstituted platelets derived therefrom), microparticles, and/or compositions for diagnostic or research purposes. Thus, the invention provides methods of diagnosing a disease or disorder of the blood clotting system. The methods generally comprise obtaining freeze-dried platelets, microparticles, and/or compositions comprising them (or rehydrated platelets, microparticles, and/or compositions), combining them with platelets and/or plasma removed from a patient having, or suspected of having, a disease or disorder of the blood clotting system to form a mixture, and determining whether the person has a defect in the blood clotting system by assaying one or more biological or biochemical functions of the mixture, where the defect decreases or abolishes the patient's blood clotting system's ability to function normally or to cause clot formation in a pre-defined period of time. Typically, determining whether the patient's blood clotting system is defective comprises assaying clotting time of the mixture. The methods of diagnosis are typically performed in vitro, but may be performed in vivo on test animals if desired. The methods of diagnosis generally are performed to identify bleeding disorders and causes of those disorders. Research methods generally relate to discovery of causes of bleeding disorders, such as the molecular basis for a particular person's inability to normally control bleeding in response to wounds or other injuries. The research methods can also relate to study of the effects of drug treatments on the blood clotting system of individuals (e.g., side effects that negatively affect blood clotting).

In yet an additional aspect, the invention provides methods of monitoring the progression of a disease or disorder of the blood clotting system. The methods generally comprise obtaining freeze-dried platelets or rehydrated platelets derived from freeze-dried platelets, combining them with platelets and/or plasma removed from the patient suffering from the disease or disorder to make a mixture, and determining the blood clotting ability of the mixture. Typically, determining the blood clotting ability of the mixture indicates the blood clotting ability of the patient's blood, and comprises assaying clotting time of the mixture. Furthermore, typically, multiple assays are performed over time to give an indication of progression over time.

In another aspect, the invention provides methods of monitoring the effects of a treatment regimen for a patient on the blood clotting system of that patient. In general, the methods comprise obtaining freeze-dried platelets or rehydrated platelets derived from freeze-dried platelets, combining them with platelets and/or plasma removed from the patient undergoing the treatment regimen to make a mixture, and determining the blood clotting ability of the mixture. Typically, determining the blood clotting ability of the mixture indicates the blood clotting ability of the patient's blood, and comprises assaying clotting time of the mixture. Furthermore, typically, multiple assays are performed over time to give an indication of the effects of the treatment regimen over time.

BRIEF DESCRIPTION OF THE DRAWINGS

The accompanying drawings, which are incorporated in and constitute a part of this specification, illustrate several embodiments of the invention and, together with the description, serve to explain certain principles of certain aspects of the invention.

FIG. 41B demonstrates the specific interaction of FITC-PPACK Factor VII with RHP.

DETAILED DESCRIPTION OF VARIOUS EMBODIMENTS OF THE INVENTION

Figure 1:
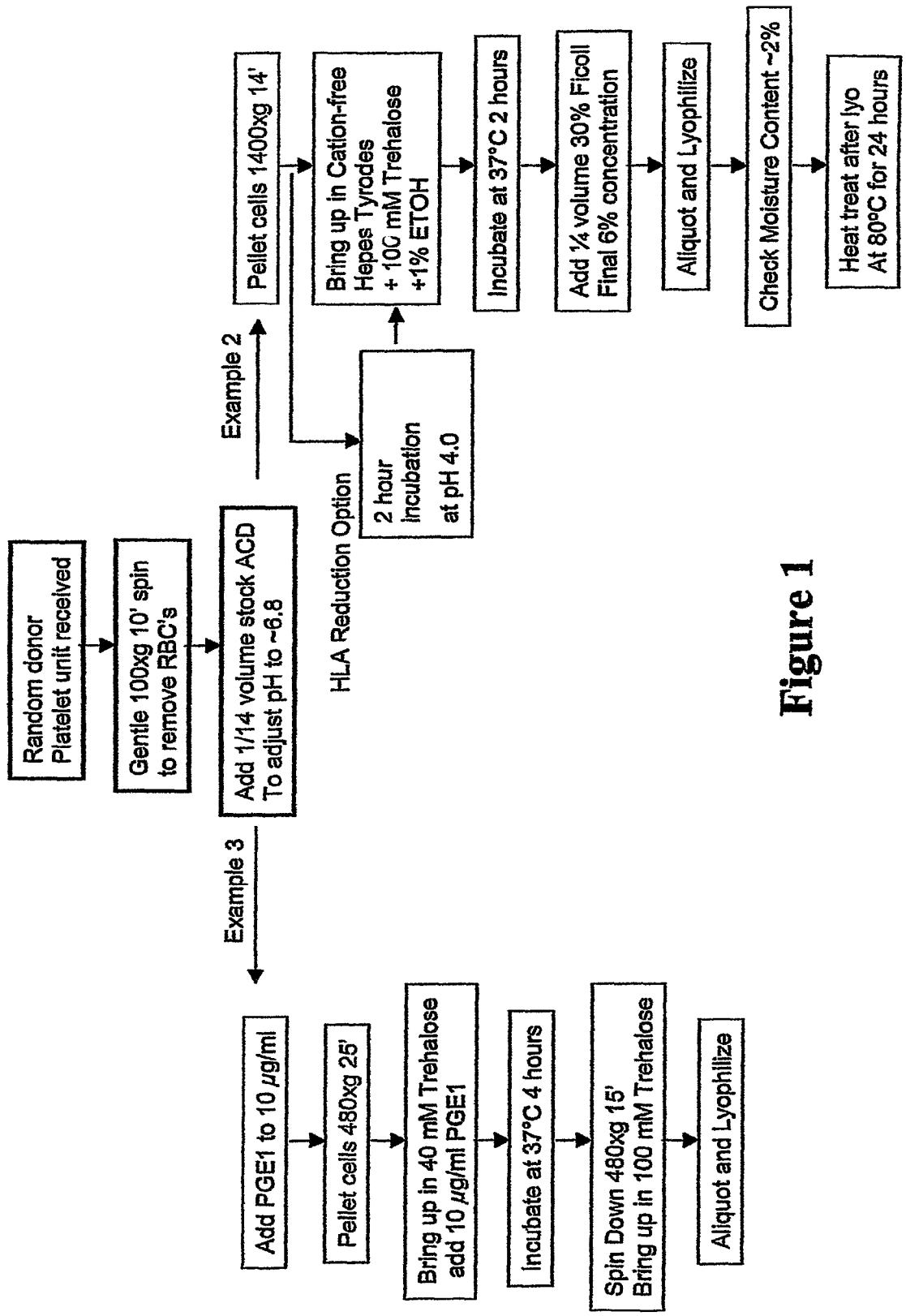
FIG. 1 is a flow diagram showing steps involved in preparation of freeze-dried platelets according to a method known in the art and a method according to embodiments of the present invention.

Reference will now be made in detail to various exemplary embodiments of the invention, examples of which are illustrated in the accompanying drawings.

In one aspect, the invention provides freeze-dried platelets, rehydrated freeze-dried platelets, and compositions comprising freeze-dried platelets or rehydrated freeze-dried platelets. The compositions can, but do not necessarily, comprise microparticles in addition to the platelets, and these microparticles can be included as a result of preparation of the freeze-dried platelets, or can be intentionally added as a component of the compositions. Regardless of how the compositions are made, depending on the method used to make the freeze-dried platelets, the platelets can have varying degrees of similarity to freshly-isolated platelets or platelets that have been stored for a short period of time, for example fewer than six days (in-dated platelets). In exemplary embodiments, the platelets retain all of the characteristics that are essential for platelet clotting function in the presence of normal platelets in blood. In other exemplary embodiments, the platelets are lacking or are deficient in one or more characteristic.

Freeze-dried platelets and rehydrated platelets derived from these freeze-dried platelets can be made from freshly isolated platelets (less than a few hours after removal from a donor subject's body) in-dated platelets (less than six days after removal from a donor subject's body), or out-dated platelets (six or more days after removal from a donor subject's body). It has surprisingly been found that out-dated platelets can be used as a source for freeze-dried platelets, and that such platelets, or rehydrated platelets derived from them, can be used not only for research purposes, but for treatment of bleeding and bleeding disorders as well.

The platelets of the invention can have essentially all of the gross morphological characteristics of normal, freshly obtained platelets in blood. For example, in certain compositions where reconstituted freeze-dried platelets are present, about 70% of the particles in the composition are retained when the composition is filtered through a mesh size that retains particles of the size of a typical platelet. Likewise, generally the platelet particles show the same array of cell surface proteins as fresh, untreated platelets. For example, size, granularity, and surface receptors, such as GPIb and GPIIb/IIIa, can be retained or partially retained on the surface of the freeze-dried platelets at the levels comparable to fresh platelets. The platelets can also contain characteristic that are not commonly found in fresh platelets, such as expression of charged lipids and granule proteins, such as P-selectin and Factor V. Due to this, such platelets confer addition functions that fresh platelets can not perform, such as binding to Vitamin K-dependent proteins and the like. In particular embodiments, the platelets retain most, if not all, of the characteristics needed for adequate blood clotting. Thus, for example, the freeze-dried platelets of the invention can retain normal size (upon rehydration), intact membranes, normal aggregation properties, proper surface protein arrays, and internal factors that participate in the clotting cascade. That is, the freeze-dried platelets of the invention can retain most, if not all, of the characteristics necessary for blood clotting function of the platelets when introduced into patients or subjects in need of platelet functions.

The platelets can be obtained from any source, including, but not limited to, mammals, such as humans, dogs or other canines, cats or other felines, mice, rats, or other rodents; pigs, horses, sheep, goats, cows, or other farm animals; and monkeys, chimps, apes, or other primates. That is, the compositions can comprise platelets from any mammalian species, including, but not limited to, humans, primates, canines, felines, bovines, ovines, porcines, equines, and rodents. In addition, the platelets can be autologous or heterologous, with respect to the blood with which they are mixed in the methods of the invention. For example, in embodiments, the methods of the invention generally comprise mixing platelets, such as freeze-dried platelets, with freshly obtained blood from a patient. The platelets are preferably, but not necessarily, obtained from the same patient as the blood (i.e., autologous platelets). However, in embodiments, the platelets are obtained from one or more individuals other than the patient (i.e., heterologous platelets). In certain embodiments, the freeze-dried platelets originate from a pool of platelets obtained from two or more donors. In certain embodiments that relate to compositions comprising both freeze-dried platelets and fresh platelets, the fresh platelets originate from a pool of platelets obtained from two or more donors.

As mentioned above, platelets for use in the invention can be obtained from indated or outdated blood. Indated blood is blood that has freshly been obtained from a donor, and includes blood that is less than six days old. In contrast, outdated blood is blood that was obtained from a donor six or more days earlier, and thus is no longer deemed by some governmental regulatory agencies as suitable for use as a therapeutic agent to treat excessive bleeding (e.g., for blood transfusions). In certain embodiments, outdated blood from one or multiple donor sources (used singly or as a mixture of blood from different sources) is used as a source of freeze-dried platelets to be used as a "normal" or "standard" control.

In addition, the platelets can be subjected to various treatments prior to use in treating a subject. In general, the platelets are concentrated from whole blood. They can be concentrated by any suitable method, including, but not limited to, centrifugation and filtration. In addition to concentration, they can be washed one or more times with saline or another suitable solution to remove some or all other blood components. Likewise, they can be maintained as a packed concentrate, having little or essentially no liquid medium surrounding them, or suspended in a suitable aqueous solution or buffer that may contain stabilizers or other substances that are compatible with platelets.

In embodiments, the concentrated platelets are freeze-dried or lyophilized. Numerous techniques for freeze-drying blood products and other biological substances are known, and any one can be used to prepare freeze-dried platelets according to the invention. Exemplary techniques are provided below and in the Examples. In yet other embodiments, the freeze-dried platelets are rehydrated with water or a biologically compatible aqueous solution, such as saline. The rehydrated platelet compositions may be used directly, or other substances, such as blood components or drugs, may be added before use in treatment of individuals in need of the platelets.

In embodiments, the invention consists of freeze-dried platelets. In other embodiments, the invention provides a composition that comprises freeze-dried platelets or platelets that are derived from freeze-dried platelets, such as, for example, platelets that were freeze-dried then reconstituted with water, saline, or plasma (also referred to herein as reconstituted or rehydrated platelets).

Accordingly, compositions according to the invention comprise platelets. The platelets can be freeze-dried platelets or rehydrated freeze-dried platelets. The compositions can comprise any number of substances in addition to platelets, including, but not limited to platelet microparticles. Thus, a composition of the invention can be a solid or a liquid. When in the form of a liquid, the composition can comprise water or another aqueous solvent, such as an aqueous buffer, blood or a blood component or fraction (such as plasma), saline, buffered saline (e.g., phosphate buffered saline), or the like. Accordingly, rehydrated freeze-dried platelets of the invention can be rehydrated with any such liquid, including without limitation water, aqueous buffer, and blood or plasma. The liquid can also comprise one or more organic solvents, such as one or more alcohols. The compositions can be suitable for in vivo treatment of bleeding or bleeding disorders, can be suitable for in vitro or in vivo diagnostics, or can be suitable for in vitro or in vivo research.

Compositions according to the invention can also comprise one or more substances that were present with the platelets before, during, or after the platelets were freeze-dried. Thus, the compositions comprising platelets can also comprise one or more salts, such as phosphate salts, sodium salts, potassium salts, calcium salts, magnesium salts, and any other salt that can be found in blood or blood products, or that is known to be useful in freeze-drying platelets or eukaryotic cells, or any combination of two or more of these. Other exemplary substances that may be present in the compositions include, but are not limited to, sugars, such as monosaccharides and disaccharides (e.g., maltose, dextrose, mannose, trehalose, sucrose, polymers of sucrose, glucose); polysugars, such as Ficoll-70 and Ficoll-400; glycerol; triglycerides; polysaccharides; lipids; dextran; polyvinyl pyrolidone (PVP); starch; hydroxyethyl starch (HES); and the like. Yet other exemplary substances include biological molecules derived from human or animal sources, such as polypeptides (e.g., albumins such as bovine serum albumin and human serum albumin), casein, laminin, fibrinogen, and the like. Of course, because the freeze-drying procedure can result in lysis of a certain number of platelets, compositions of the invention may comprise, external to intact platelets, some or all of the components present in the interior of a platelet.

One particular group of substances that may be present in a composition of the invention is chemical and biological compounds that function as drugs. Another group is substances that function as food. Yet another group is substances that function as herbal supplements. In embodiments, the substances are anti-coagulants. Compositions of the invention can, but do not necessarily, contain fibrin. Compositions according to the invention that do not contain fibrin can provide an advantage over compositions known in the art, for example when the compositions of the invention are used to treat non-compressible wounds.

As will be discussed below in more detail, the compositions and methods of the present invention are particularly well suited for detection and monitoring of drugs, food, and herbal supplements in blood samples, and detection and monitoring of the effects of these substances on the blood clotting system of the patient to whom the drugs, etc. are administered. Among the drugs are Warafin (Coumadin®), Heparin, Clopidogrel (Plavix®), Dipyridamole (Persantine®), Enoxaparin (Lovenox®), Ardeparin (Normiflo®), Dalteparin (Fragmin®), Ticlopidine (Ticlid®), Danaparoid (Orgaran®), Tinzaparin (Innohep®), Aspirin, Thrombin Inhibitors, and the like. Also among the substances are certain food and herbal supplements that contain coumarins with potential anticoagulant effects, such as Alfalfa, Angelica (Don Quai), Arnica, Bogbean, Capsicum, Celery, Dandelion, Horse chestnut, Horseradish, Meadowsweet, Nettle, Parsley, Passion, Flower, Red Clover, Sweet Clover, Wild Carrot, Wild Lettuce. In addition, the substances can be those that have anti-platelet properties, such as Agrimony, Aloe gel, Black cohosh, Bogbean, Clove, Dandelion, Garlic, Ginger, *Ginkgo biloba*, Ginseng (Panax), Licorice, Meadowsweet, Onion, Policosanol, Poplar, Senega, Tamarind, Willow Wintergreen, and the like.

The compositions thus can comprise other blood components, and in particular can comprise other blood clotting factors in their normal or activated states, such as Factor VII and Factor VIII. These other components may be present as a result of the concentrating of the platelets or they may be added as separately purified components to the platelets. These other blood components may be present singly (i.e., only one is present in the composition), or multiple other blood components may be included in the composition together with the platelets. Typically, the other blood components are included in amounts or concentrations that, when administered to an individual at the amount chosen for the platelets, provide a detectable change in at least one physiological process of the treated individual, or provides a known benefit.

For example, in the presence of 50,000 platelets or platelet derivatives per microliter, recombinant Factor VIIa may be included in the composition (or administered separately) at an amount to provide a dose to a patient of 10 ug/kg of body weight; this amount is much lower than the standard 90 ug/kg used to treat hemophiliacs with inhibitors. With regard to this embodiment of the invention, it has been found that the platelet-containing compositions of the present invention, when supplied in conjunction with purified recombinant Factor VIIa, reduce the amount of Factor VIIa that is required for activity by 5 to 10 times. That is, as described in the text below, it has been discovered that, when recombinant Factor VIIa is used in conjunction with concentrated lyophilized and rehydrated platelets of the invention, the amount of recombinant Factor VIIa needed to achieve clotting in a normal amount of time is 5 to 10 fold less than if recombinant Factor VIIa is used alone.

Likewise, the compositions can comprise other components that are not normal blood components. Such components can be salts, detergents, and other non-biological substances that provide any number of beneficial properties to solutions, such as stabilizing proteins in solution, making the solution biologically compatible, etc. Such components can also be substances that have a known biological activity, such as chemotherapeutic agents, antibiotics, vitamins, etc. As with the blood components, non-blood components that are present in the solution are preferably included in an amount that provides the intended function. For example, salts are preferably added in an amount that stabilizes proteins in the composition or provides compatibility with the recipient's blood. Further, antibiotics or chemotherapeutic agents (and the like) are added in an amount that will, when administered to an individual at the amount chosen for the platelets, provide a detectable change in at least one physiological process of the treated individual, or provide a known benefit (e.g., a known antibiotic is supplied to the treated individual in an amount known to be suitable for combating a bacterial infection).

In certain embodiments, compositions of the invention comprise platelets, microparticles, or both, but no other substance that is biologically active in forming a clot. Accordingly, the present invention provides compositions that promote clotting activity, either when they comprise platelets alone or when they comprise platelets and other blood clotting factors.

In embodiments where the compositions comprise microparticles, the platelets typically comprise about 10% to about 70% of the total number of particles, particularly platelet or platelet-derived particles, in the composition. For example, platelets can comprise about 10% to about 60%, about 10% to about 50% of the particles, about 20% to about 50% of the particles, about 20% to about 40% of the particles, or about 20% to 30% of the particles. In embodiments, about 70% of the particles in the composition are retained when the composition is filtered through a mesh size that retains particles of the size of a typical platelet. Thus, in embodiments up to about 70% of the particles in the composition are platelets. Accordingly, the compositions of the invention can comprise 70% platelets and 30% microparticles, 60% platelets and 40% microparticles, 50% platelets and 50% microparticles, 40% platelets and 60% microparticles, 20% platelets and 80% microparticles, or 10% platelets and 90% microparticles. In exemplary embodiments, the composition comprises platelets and microparticles as essentially the only particles that are part of the blood clotting system, and comprises platelets in an amount of about 10%, about 20%, about 30%, about 40%, about 50%, about 60%, or about 70% of the total particle count. Of course, a composition of the invention may comprise any specific percentage number, or fraction thereof, of platelets or microparticles within the ranges discussed above. Because one of skill in the art would immediately recognize each of the numerous possible combinations of amounts of platelets and microparticles, it is not necessary to specifically disclose each herein.

It is also to be noted that, as used herein with reference to the compositions of the invention, "platelets" and "platelet derivatives" are used interchangeably, and encompass a composition that comprises all or substantially all platelets, all or substantially all platelet derivatives (particles derived from platelets, such as platelet fragments, microparticles, and inside-out platelets), or a mixture of any amount of each.

The platelets can be present in any suitable composition or formulation, and in any concentration that is suitable for use in the methods of the invention. Thus, platelets obtained by centrifugation of normal blood can be used, as can portions or fractions of platelets obtained from blood (such as a portion of the platelets obtained from 0.5 liter, 1 liter, or 1 pint of human blood). Because the entire body of an individual will be treated with the compositions of the invention, the compositions do not include whole blood. That is, because it would be impractical and unnecessary to treat an individual with a whole blood transfusion, compositions according to the invention comprise platelets in a concentrated form, as compared to whole blood. While a large range of concentrations is acceptable, it is preferable to provide compositions in which the platelet derivatives are supplied in a form approximately 10-fold or more concentrated than in whole blood, and in which they provide an increase in the basal platelet count from about 50,000 to about 500,000 platelets/ul. Thus, they may be present in a concentration that is, or is about, 2-fold or less, 5-fold, 10-fold, 15-fold, 20-fold, 25-fold, or more concentrated than in normal whole blood. They also may be present in an amount that provides an increase in the basal platelet count in the blood of a patient from, or from about, 50,000 or less, 60,000, 70,000, 80,000, 90,000, 100,000, 125,000, 150,000, 200,000, 250,000, 300,000, 350,000, 400,000, 450,000, 500,00, or more. The platelet derivatives may also be dosed based upon their total phospholipid content rather than, or in addition to, that measured by enumerated counts. Amounts provided in the compositions and amounts administered may thus vary, depending on the intended recipient (infant, child, adult) and the basis upon which dosage is calculated. Such calculations are well within the skill of those of skill in the art, and thus can be performed without undue experimentation.

Thus, the freeze-dried platelets or rehydrated freeze-dried platelets can be present in the compositions in an amount of from $1\times10^5$ to $1\times10^{11}$. In embodiments where fresh platelets are present in the compositions as well, the fresh platelets are typically present in an amount of from $1\times10^5$ to $1\times10^{11}$. In exemplary embodiments, one or both type of platelets are present in a composition in amounts of about $1\times10^8$ to $1\times10^{10}$, such as about $1\times10^9$. In compositions comprising both fresh and freeze-dried platelets, the amounts of each may be the same or different.

As discussed in detail below, the methods of certain embodiments of the invention generally comprise mixing freeze-dried platelets with fresh blood or a fraction of fresh blood (e.g., plasma), which might or might not contain platelets, to make a mixture. Such a mixture is considered a composition according to the present invention. Thus, in embodiments, a composition of the invention comprises fresh platelets, which have been obtained from a donor and not subjected to any freeze-drying technique. Likewise, a composition of the invention can comprise a combination of both fresh platelets and freeze-dried platelets. Each of these types of platelets may be present in the composition in any amounts or concentrations, regardless of the amount or concentration of the other. Suitable amounts of each may be selected by the practitioner based, at least in part, on the considerations described herein with regard to practice of the methods of the invention.

The pH of the composition may be any pH that is suitable for stability and function of platelets. Accordingly, it can range from mildly acidic to mildly basic, such as from pH 4.0 to pH 8.5. In various embodiments, the pH of the composition is 4.0, 4.5, 5.0, 5.5, 6.0, 6.5, 7.0, 7.5, 8.0, or 8.5. In other embodiments, the pH is any other pH within the range of 4.0 to 8.5. In embodiments where the platelets are in a solid (dry) state, the compositions may comprise one or more substance that, when hydrated, causes the pH of the resulting liquid composition to be in a suitable range.

Trehalose and/or another sugar can be included in the composition, and the trehalose and/or other sugar can be present outside the platelets, inside the platelets, or both. Although any amount may be suitable, the amount of trehalose or sugar typically ranges from 50 mM to 150 mM. In various embodiments, the trehalose concentration is 50 mM, 75 mM, 100 mM, 125 mM, or 150 mM. In other embodiments, the trehalose concentration is any other concentration within the range of 50 mM to 150 mM. In embodiments where the platelets are in a solid (dry) state, the compositions may comprise one or more substance that, when hydrated, causes the concentration of trehalose of the resulting liquid composition to be in a suitable range.

A composition that is suitable for loading trehalose and/or another sugar into platelets can comprise ethanol. In such a composition, the ethanol can range from 0.1% to 5.0% (v/v). In various embodiments, the ethanol concentration is 0.1%, 0.5%, 1%, 2.5%, or 5%. In other embodiments, the ethanol concentration is any other concentration within the range of 0.1% to 5%.

In embodiments where the platelets are in a solid (dry) state, the platelets or composition in which they exist can be heated, such as at room temperature, 50° C., 55° C., 60° C., 65° C., 70° C., 75° C., 80° C., 85° C., or 90° C. In embodiments, the temperature is any temperature within the range of room temperature to about 90° C. The heating process can promote formation of platelets that are suitable for assays of platelet function.

In embodiments where the platelets are in a solid (dry) state, they can be heated from less than one minute up to 24 hours or more. Accordingly, the time of heating can be 0, 2, 4, 8, 12, or 24 hours. In other embodiments, the time of heating is any time within the range of less than 1 minute to 24 hours, including any minute or fraction thereof within that range.

As should be evident from the present disclosure, with the exception of certain drugs and anti-platelet compounds in compositions according to certain embodiments, any and all substances that are present in the compositions of the invention are preferably present in amounts that are compatible with at least one function of normal platelets. That is, the compositions of the invention may comprise numerous substances in addition to platelets, but each substance, and the total combination of substances, present is preferably present in an amount that permits the platelets to function normally, at least with respect to one platelet function. In embodiments where one or more substance is present in an amount that inhibits normal platelet function, it is preferred that the substance be removed or adjusted in concentration prior to use of the platelets in a method of the invention in order to permit the method to function well. Of course, these considerations are not relevant to drugs and other anti-platelet substances that are intentionally included in the compositions to determine the effect of such substances on platelet or clotting system function.

The freeze-dried platelets, rehydrated freeze-dried platelets, and compositions of the invention are suitable for many purposes, including, but not limited to use in both in vitro diagnostic and research purposes as well as in vivo therapeutic purposes. For example, the freeze-dried platelets can be rehydrated and used to treat subjects suffering from excessive bleeding or suffering from a bleeding disorder. Alternatively, they can be used to study platelet function in the laboratory setting, or to research the effect of platelets or platelet components on the blood clotting system. One of skill in the art can envision numerous specific diseases and disorders that can be treated with platelets, and all of those diseases and disorders can be treated with the freeze-dried platelets of the invention.

The platelets and compositions of the invention are highly stable, having a shelf-life of at least six months at room temperature or below. For example, the freeze-dried platelets can be stable up to one year at room temperature or below, up to 18 months at room temperature or below, or even longer. By "stable" it is meant that the platelets, when rehydrated, function within normal parameters for in-dated platelets, and provide adequate blood clotting functions when administered to a subject in need. This stability is of great advantage in providing platelet products to those in need, particularly those found at sites some distance from blood collection centers. Furthermore, because the freeze-dried platelets can be stored at room temperature, complicated, bulky, or expensive containers for storage (e.g., refrigerators) are not needed. In addition, because the platelets can be stored in the dehydrated state, significant savings in volume and weight can be achieved, as compared to fresh, concentrated platelets.

The freeze-dried platelets of the invention are highly stable, even when exposed to high gamma irradiation dose of 50 kGY or heat treated at 80° C. for 24 hrs. This property is advantageous in that it enables the platelets to be treated for pathogen reduction.

In addition, freeze-dried platelets made according to methods of the invention, upon rehydration, show properties of fresh or in-dated platelets. For example, upon rehydration, they show the swirling characteristic of fresh or in-dated, unactivated platelets. Furthermore, upon rehydration, they show a similar size and granularity as fresh or in-dated platelets. Other characteristics of the freeze-dried platelets, upon rehydration, are mentioned above.

In embodiments, the composition comprises concentrated platelets from blood, where the platelets have been freeze-dried or lyophilized and reconstituted with a water-based solution, such as saline. Numerous sources of blood are available, and any one can be used, including, but not limited to, the general public blood supply and autologous blood supplies. Likewise, numerous methods of freeze-drying of platelets are known to those of skill in the art, and any suitable technique may be used. Exemplary freeze-drying techniques are presented below.

The platelets of the invention can be used as an injectable or infusible substance for treatment of bleeding in a patient, or can be used as a direct treatment for bleeding that is accessible from outside the body. They likewise can be used for in vivo or in vitro diagnostic purposes or for in vivo or in vitro studies, such as for studies on the blood clotting process. The freeze-dried platelets, or rehydrated platelets made from them, can have properties of freshly obtained or in-dated platelets sufficient to provide clotting functions, and promote wound healing.

One advantage to embodiments of the freeze-dried platelets, rehydrated platelets, and compositions of the present invention is that platelet microparticles can accelerate clot formation, likely at least in part by way of their ability to promote tenase and prothrombinase activities, thereby enhancing thrombin-generating capacity and promoting rapid clot development at the injury site. In addition, due to the fact that the compositions can comprise a platelet-derived material and can contain a number of important growth factors, they can also contribute to the process of wound healing and tissue regeneration. Studies have found that mitogenic lipids and growth factors, such as platelet derived wound healing factors (PDWHF), platelet-derived growth factor (PDGF), transforming growth factor (TGF), and insulin growth factors (IGF), among others, are important in different stages of wound-healing cascade and greatly influence mitogenic and cellular differentiation activities. Thus, in embodiments, one or more of these factors are included in the compositions or provided in the methods of treating.

In another aspect, the invention provides a method for preparing freeze-dried platelets. In general, the method comprises providing platelets, exposing the platelets to at least one saccharide, forming a composition, incubating the composition at a temperature above freezing for at least a sufficient time for the at least one saccharide to come into contact with the platelets, adding a cryoprotectant to make a second composition, and lyophilizing the second composition. Exposing the platelets to at least one saccharide can be accomplished in a buffer, such as a salt buffer. The amount of time that the platelets and saccharide are in contact can be sufficient for the saccharide to be taken into the platelets. The freeze-dried platelets can be re-constituted or re-hydrated (used interchangeably herein) by exposure to an aqueous liquid, such as water or an aqueous buffer. Alternatively, the freeze-dried platelet preparations can be used directly in methods of treating, diagnostic methods, or research methods. Specific exemplary methods for preparing freeze-dried platelets are provided below.

The act of providing platelets can be any act that results in platelets being made available for use in the method in a form suitable for use in the method. Thus, providing can comprise removing blood from a subject and isolating or purifying (to any suitable extent) platelets from other blood components. Any known procedure for separating platelets from other blood components can be used. Accordingly, it can be through a process of obtaining platelets through plasmapheresis or sequential differential centrifugation of blood. For example, differential centrifugation can be used to isolate or purify platelets from other blood components through a two-step process in which blood is centrifuged at 3000×g for 45 minutes; platelet-poor liquid removed; the platelet-rich pellet resuspended in an aqueous buffer, and the mixture re-centrifuged at 200×g for 5 minutes to pellet the platelets. Alternatively, a single centrifugation step can be used, such as centrifugation at 100×g for 10 minutes. During the process of obtaining the platelets, one or more substances may be added to the compositions comprising the platelets, such as one or more anticoagulant or stabilizer. Other methods are known to those of skill in the art, and any such method can be used without undue or excessive experimentation.

The platelets may be from any source. Accordingly, they may be from an animal, such as a pig, horse, dog, cow, sheep, goat, rabbit, rat, mouse, monkey, or cat. They also may be from a human. In certain cases, the platelets may be provided as a mixture from two or more sources, such as a mixture of two or more units of blood obtained from random blood donors to a public blood bank. In other embodiments, such as embodiments where the platelets are intended to be used at a later date for infusion back into the donor, the platelets can be from a known source, and are thus considered autologous platelets for the purposes of the methods of treatment disclosed herein. More specifically, the platelets may be originally obtained from the ultimate recipient of the freeze-dried platelets or reconstituted platelets. In general, the platelets will be provided from a fresh source (i.e., in-dated platelets from blood obtained from a donor less than 6 days prior to freeze-drying), although out-dated platelets may be used in some situations, particularly for preparation of freeze-dried platelets intended for use in in vivo and in vitro for diagnostics or research, such as for use as a hemostat to aid in stopping bleeding at a particular site of injury.

The platelets that are provided are suspended in a salt buffer that comprises at least one saccharide, resulting in a platelet-containing composition. The salt buffer may be any buffer that maintains at least a majority of the platelets in an intact, functional state while in the buffer. Preferably, the buffer maintains the platelets at a pH of about 6.2 to about 7.8. Thus, the salt buffer may be an isotonic salt buffer comprising salts naturally encountered by platelets, such as those comprising sodium salts, potassium salts, calcium salts, and the like, and combinations of such salts. Alternatively, it may comprise one or more salts that platelets are not naturally in contact with. The identity of the salt(s) in the buffer are not critical so long as they are present in amounts that are not toxic to the platelets and maintain at least a majority of the platelets in an intact, functional state while in the buffer. Likewise, the buffering component may be any buffer that is non-toxic to the platelets and provides adequate buffering capacity to the composition at the temperatures at which the composition will be exposed during the method of the invention. Thus, the buffer may comprise any of the known biologically compatible buffers available commercially, such as HEPES, phosphate-buffered saline (PBS), and Tris-based buffers, such as TBS. Likewise, it may comprise one or more of the following buffers: propane-1,2,3-tricarboxylic (tricarballylic); benzenepentacarboxylic; maleic; 2,2-dimethylsuccinic; EDTA; 3,3-dimethylglutaric; bis(2-hydroxyethyl)imino-tris(hydroxymethyl)-methane (BIS-TRIS); benzenehexacarboxylic (mellitic); N-(2-acetamido)imino-diacetic acid (ADA); butane-1,2,3,4-tetracarboxylic; pyrophosphoric; 1,1-cyclopentanediacetic (3,3tetramethylene-glutaric acid); 1,40piperazinebis-(ethanesulfonic acid) (PIPES); N-(2-acetamido)-2-amnoethanesulfonic acid (ACES); 1,1-cyclohexanediacetic; 3,6-endomethylene-1,2,3,6-tetrahydrophthalic acid (EMTA; ENDCA); imidazole; 2-(aminoethyl)trimethylammonium chloride (CHOLAMINE); N,N-bis(2-hydroxyethyl)-2-aminoethanesulfonic acid (BES); 2-methylpropane-1,2,3-triscarboxylic (beta-methyltricarballylic); 2-(N-morpholino)propane-sulfonic acid (MOPS); phosphoric; N-tris(hydroxymethyl)methyl-2-aminoethane sulfonic acid (TES); and N-2-hydroxyethylpiperazine-N'-2-ethanesulfonic acid (HEPES). Furthermore, the buffer system can provide buffering capacity at the range of pH 4 to pH 8.

The salt buffer comprises at least one saccharide. The saccharide can be any suitable saccharide, including a monosaccharide or disaccharide or polysaccharide. The saccharide can be any saccharide that is compatible with maintenance of viability and function of platelets, and can be present in any amount that is not toxic to the platelets. In general, the saccharide can be any saccharide that is capable of passing through a cell membrane, such as the platelet membrane. Examples of suitable saccharides are sucrose, maltose, trehalose, glucose, mannose, xylose, Ficoll-70, and hydrogels having a molecular weight cut-off of less than about 100 kilodaltons. It is known that saccharides can be advantageously included in compositions for freeze-drying or lyophilizing platelets, and the present invention envisions use of at least one saccharide for stabilizing or otherwise promoting survival of platelets through the freeze-drying and reconstitution process. A preferred saccharide for use in the method of preparing freeze-dried platelets is trehalose. The saccharide may be present in the buffer in any suitable amount. For example, it may be present in an amount of 1 mM to 1 M. In embodiments, it is present in an amount of from 10 mM 10 to 500 mM. In some embodiments, it is present in an amount of from 20 mM to 200 mM. In embodiments, it is present in an amount from 40 mM to 100 mM. In certain particular embodiments, the saccharide is present in the buffer in an amount of at least or about any of the following concentrations: 40 mM, 50 mM, 60 mM, 70 mM, 80 mM, 90 mM, and 100 mM. Of course, in various embodiments, the saccharide is present in different specific concentrations within the ranges recited above, and one of skill in the art can immediately understand the various concentrations without the need to specifically recite each herein. Where more than one saccharide is present in the buffer, each saccharide may be present in an amount according to the ranges and particular concentrations recited above.

The salt buffer may comprise other components, as long as those components are non-toxic to the platelets at the concentration in which they are present in the buffer. Thus, polymers, such as proteins and polysaccharides, may be included in the buffer. Likewise, alcohols, such as ethanol, or polyalcohols, such as glycerols and sugar alcohols, may be included. Similarly, organic solvents, such as dimethyl sulfoxide (DMSO), can be included. Further, coagulation or platelet inhibitors, such as heparin, EGTA, citrate, and prostaglandin E (PGE).

In embodiments, the buffer comprises a cation-free HEPES-Tyrodes buffer (95 mM HEPES, 1 M NaCl, 48 mM KCl, 120 mM NaHCO$_3$) comprising 50 mM trehalose, pH 6.8. In other embodiments, the buffer comprises a cation-free HEPES-Tyrodes buffer comprising 100 mM trehalose and 1% (v/v) ethanol, pH 6.8.

The platelet-containing composition is incubated, at least in part to permit loading of the saccharide into the platelets. In general, the composition is incubated at a temperature above freezing for at least a sufficient time for the saccharide to come into contact with the platelets. Thus, incubation can be at 1° C., 4° C., 10° C., 20° C., 22° C., 25° C., 37° C., 42° C., 50° C., 55° C., or greater. In embodiments, incubation is conducted at 37° C. Furthermore, incubation can be performed for any suitable length of time, as long as the time, taken in conjunction with the temperature, is sufficient for the saccharide to come into contact with the platelets and, preferably, be incorporated, at least to some extent, into the platelets. In embodiments, incubation is carried out for at least or about 10 minutes, 20 minutes, 30 minutes, 40 minutes, 50 minutes, 60 minutes, 70 minutes, 80 minutes, 90 minutes, 100 minutes, 110 minutes, 120 minutes, 130 minutes, 140 minutes, 150 minutes, 160 minutes, 170 minutes, 180 minutes, or longer. In certain embodiments, incubation is performed at 20° C. to 42° C. for 100 minutes to 150 minutes. For example, in embodiments, incubation is performed at 35° C. to 40° C. (e.g., 37° C.) for 110 to 130 (e.g., 120) minutes. While incubation at higher temperatures than about 37° C. have been found to be suitable, it has been determined that such higher temperatures are unnecessary and, in embodiments, provide less than superior results. Furthermore, while incubation times greater than about 2 hours have been found to be suitable, it has been determined that such longer times are unnecessary and, in embodiments, provide less than superior results. Furthermore, reducing the time to 2 hours from, for example, 4 hours, reduces the time required to produce freeze-dried platelets, and provides an advantage for the practitioner over some other methods available in the art. In embodiments where activated platelets are desired, incubation times approaching or exceeding 4 hours in the presence of trehalose may be used. However, to reduce the amount of activation and minimize loss of structural integrity, incubation times of less than 4 hours, such as 2 hours, are more suitable.

The method of freeze-drying platelets comprises adding a cryoprotectant to the platelet composition to make a second composition, referred to from here out as the lyophilization buffer. The lyophilization buffer comprises, in addition to the components discussed above, a cryoprotectant (also referred to herein as an excipient). The cryoprotectant can be any suitable substance that protects, at least to some extent, the platelets during the subsequent freezing and thawing procedures. Various cryoprotectants are known in the art, and any of those may be used in an amount that is effective and non-toxic to the platelets. Examples of suitable cryoprotectants include, but are not limited to, bovine serum albumin, human serum albumin, dextran, polyvinyl pyrolidone (PVP), starch, hydroxyethyl starch (HES), and polysugars, such as Ficoll-70 and Ficoll-400. The cryoprotectant is included in the lyophilization buffer at an amount of from 1% to 50% (w/v), such as from 5% to 40%, 5% to 30%, 5% to 20%, and 5% to 10%. In embodiments, the cryoprotectant is present in the lyophilization buffer at a final concentration of 1%, 2%, 3%, 4%, 5%, 6%, 7%, 8%, 9%, or 10%. In certain embodiments, the cryoprotectant is present in the lyophilization buffer in a final concentration of 4%-8%. In embodiments, the excipient is serum albumin, such as bovine serum albumin or human serum albumin. In other embodiments, the excipient is not from an animal or human source. In these embodiments, the excipient is selected so as to reduce the likelihood that contaminants, such as infectious particles, are introduced into the platelet preparations. For example, when human serum albumin is used, there is the possibility that the albumin could be contaminated with one or more infectious particles (e.g., a virus). Likewise, if bovine serum albumin is used, there is a possibility that the albumin could contain immunogenic particles that could cause an adverse reaction if administered to a human patient. Thus, it is preferred in certain embodiments to use an excipient that is not from a biological source, such as Ficoll-400. Adding of the cryoprotectant to the loading buffer is accomplished without an intervening centrifugation or other separation step. That is, the cryoprotectant (and other optional components) is added directly to the loading buffer to make a second buffer suitable for direct lyophilization. This contrasts with currently available protocols in the art, which require a separation step between saccharide loading and lyophilization.

The method of making freeze-dried platelets comprises lyophilizing, or freeze-drying, the second composition. Numerous protocols for lyophilization of eukaryotic cells and cell-like particles, including platelets, are known in the art, and any suitable protocol may be used. As used herein, lyophilization or freeze-drying is a method of drying a substance using a combination of cold temperature and vacuum. Typically, the procedure uses freezing of the substance followed by dessication by sublimation and/or desorption of water and other liquids through the use of a vacuum. In general, lyophilization results in platelets having a water content of less than 10%. In embodiments, lyophilization results in platelets having a water content of less than 5%, such as 4%, 3%, 2%, 1%, or even less. It is known in the art that, in general, the lower the water content achieved, the more stable (e.g., longer shelf-life) of the resulting freeze-dried platelets. Thus, in embodiments, it is preferred to reduce the water content to as low of an amount as possible. Preferably, the water content is reduced to 2% or less, which is an amount that minimizes deleterious effects of a post-lyophilization heat step (where used), and promotes long-term stable storage of the freeze-dried platelets.

One example of a suitable lyophilization protocol includes freezing the lyophilization composition at −45° C. for 2 hours, maintaining the frozen composition at −40° C. for 150 minutes at a vacuum of about 100 mTorr, and slowly raising the temperature, in 10° C. increments, to 25° C. (at about 100 mTorr vacuum) over a six hour period. Another example of a suitable lyophilization protocol includes freezing the lyophilization composition at −45° C. for about 4.5 hours, maintaining the frozen composition at −45° C. to −40° C. for one hour under a vacuum of 100 mTorr, and slowly raising the temperature, in 10 degree steps, to 30° C. over a 24 hour period at 100 mTorr vacuum. Another particular protocol is given in Table 3, below.

In some embodiments, the method of preparing freeze-dried platelets further comprises heating the lyophilized platelets. It has surprisingly been found that a heat treatment step after lyophilization improves the stability of the freeze-dried platelets, and provides platelets that, upon rehydration, are highly active. Heating can be performed at any temperature above 25° C. Preferably, the heat treatment is performed at a temperature greater than 40° C., such as at a temperature greater than 50° C., a temperature greater than 60° C., a temperature greater than 70° C., or a temperature greater than 80° C. In particular embodiments, heating is conducted at 70° C.-85° C., such as at 75° C., 80° C., 85° C., or any other specific temperature within the range of 75° C. to 85° C., inclusive. The temperature for heating is selected in conjunction with the length of time that heating is to be performed. Although any suitable time can be used, typically, the lyophilized platelets are heated for at least 1 hour, but not more than 36 hours. Thus, in embodiments, heating is performed for at least 2 hours, at least 6 hours, at least 12 hours, at least 18 hours, at least 20 hours, at least 24 hours, or at least 30 hours. For example, the lyophilized platelets can be heated for 18 hours, 19 hours, 20 hours, 21 hours, 22 hours, 23 hours, 24 hours, 25 hours, 26 hours, 27 hours, 28 hours, 29 hours, or 30 hours. Non-limiting exemplary combinations include: heating the freeze-dried platelets for at least 30 minutes at a temperature higher than 30° C.; heating the freeze-dried platelets for at least 10 hours at a temperature higher than 50° C.; heating the freeze-dried platelets for at least 18 hours at a temperature higher than 75° C.; and heating the freeze-dried platelets for 24 hours at 80° C. While not necessary, it is preferred that heating be performed on lyophilized platelets that are in a sealed container, such as a capped vial. In addition, while not required, it is preferred that the sealed container be subjected to a vacuum prior to heating.

The heat treatment step, particularly in the presence of a cryoprotectant such as albumin or Ficoll-400, has been found to improve the stability and shelf-life of the freeze-dried platelets. Indeed, advantageous results have been obtained with the particular combination of serum albumin or Ficoll-400 and a post-lyophilization heat treatment step, as compared to those cryoprotectants without a heat treatment step. For example, advantageous results have been obtained by using a combination of Ficoll-400 at about 6% and a post-lyophilization heat treatment step at about 80° C. for about 24 hours.

In embodiments, the method of preparing freeze-dried platelets according to the invention does not require a centrifugation step between incubating the platelets in the salt buffer and lyophilizing. Rather, the lyophilization composition may be created directly from the salt buffer composition, and freeze-dried platelets produced from that lyophilization composition directly. This is in contrast to methods currently in use in which two distinct buffers are used to prepare lyophilized platelets (e.g., a "loading buffer" and a "lyophilization buffer"), and where the platelets are removed from the first buffer (and typically washed) prior to exposure to the second buffer.

In embodiments of the method of preparing freeze-dried platelets, the method comprises an HLA reduction step. This step is optional and can be used to produce low-HLA content platelets. Low-HLA content platelets have been reported to be beneficial for in vivo therapeutic use in subjects having a strong immunogenic reaction to platelet therapies. In embodiments where an HLA reduction step is included, the buffer for the reduction step can be any suitable buffer, such as a cation-free HEPES-Tyrodes buffer (95 mM HEPES, 1 M NaCl, 48 mM KCl, 120 mM NaHCO$_3$) and 10 mM EGTA, pH 4. To effect HLA reduction, the platelets can be incubated in the buffer for a suitable amount of time, such as two hours. Although the HLA reduction step can be performed at any point in the process, it is preferred that it be performed prior to the saccharide loading step. Thus, in embodiments, HLA-deficient platelets can be achieved by incubation in the appropriate buffer prior to saccharide loading, then washed and incubated in a loading buffer, such as one comprising a cation-free HEPES-Tyrodes buffer comprising 100 mM trehalose and 1% (v/v) ethanol, pH 6.8.

In addition, the method can optionally comprise rehydrating the freeze-dried platelets. When such a rehydration step is included, the method can be considered as part of the method of making platelets or as a separate and distinct method of making rehydrated freeze-dried platelets (or compositions comprising them). More specifically, because the freeze-dried platelets of the invention may be stored for extended periods of time in a stable form, the method of rehydration may be practiced months or years after the method of making the freeze-dried platelets, and thus can be considered a distinct method. Rehydration can be by any suitable technique, such as those commonly used in the art. Typically, rehydration comprises exposing the freeze-dried platelets to water or an aqueous solution in an amount sufficient to partially or fully rehydrate the platelets, such as to provide normal shape and fluid content, and/or normal function. Suitable rehydrating solutions are known in the art and include, without limitation, phosphate buffered aqueous compositions (e.g., PBS). Certain particular rehydration compositions are provided herein. In embodiments, the rehydration buffer can have a formulation similar to the lyophilization buffer so that any initial deleterious effect of water on the freeze-dried platelets can be minimized. Exemplary rehydration buffers can be, but are not limited to, whole blood, plasma, serum, and aqueous solutions containing bovine serum albumin, human serum albumin, dextran, polyvinyl pyrolidone (PVP), starch, hydroxyethyl starch (HES), and polysugars, such as Ficoll-70 and Ficoll-400. These can be included in the aqueous rehydration buffer at an amount of from 1% to 50% (w/v), such as from 5% to 40%, 5% to 30%, 5% to 20%, and 5% to 10%. In embodiments, these are present in the rehydration buffer at a final concentration of 1%, 2%, 3%, 4%, 5%, 6%, 7%, 8%, 9%, or 10%. In certain embodiments, these are present in the rehydration buffer in a final concentration of 4%-8%.

According to the method of rehydrating, the freeze-dried platelets are exposed to an aqueous liquid. The aqueous liquid may be water, or it can be a liquid comprising water and one or more other substances, such as salts or buffers. Typically, the liquid will be an aqueous buffer, such as PBS, an aqueous composition comprising another biologically compatible buffer (e.g., HEPES) or whole blood, plasma, serum, or any osmotically balanced biological buffers. In embodiments, the rehydration buffer comprises a high molecular weight polymer, such as a poly-sugar. Included among these polymers is Ficoll-400. In embodiments, the rehydration buffer can also comprise bovine serum albumin, human serum albumin, dextran, polyvinyl pyrolidone (PVP), starch, and hydroxyethyl starch (HES). Preferably, the rehydration buffer comprises components that promote retention of platelet integrity, such as those that provide the correct osmotic pressure.

The platelets are exposed to the liquid in a sufficient amount and for a sufficient amount of time to rehydrate the platelets, for example such that they regain a normal shape and fluid content. The amount of liquid and amount of time will vary depending on the final concentration of platelets desired, the buffer, and the temperature at which the platelets are rehydrated. In embodiments, the amount of aqueous liquid is two times the volume of the dried platelets. While any temperature may be used, in general it will be most convenient to rehydrate the platelets at ambient room temperature (e.g., 20° C.-25° C.). The rehydration time can be any appropriate time. Thus, it can range from 10 seconds to over one hour. For example, it can be about one minute or less, about five minutes or less, about ten minutes or less, about 30 minutes or less, and about 60 minutes or less. In embodiments, rehydration can be accomplished by physically resuspending the platelets (e.g., by swirling or pipetting) for 10-30 seconds, then letting the platelets stand undisturbed at room temperature for 5 minutes.

Furthermore, rehydration can be performed using any known general protocol. Thus, the platelets can be rehydrated directly with the rehydration liquid or can be rehydrated indirectly or passively. Direct methods can include directly applying a volume of liquid to the freeze-dried platelets, such as by adding the liquid to a pellet of platelets, and allowing the liquid sufficient time to contact the platelets and rehydrate them. Direct rehydration can also comprise physically dispersing the platelets at one or more times while in contact with the liquid, such as by swirling or pipetting gently. In embodiments of direct rehydration, the rehydration buffer is gently added to the freeze-dried platelets and allowed to stay in contact with them in an undisturbed state for 10-60 seconds, such as for 30 seconds, then the platelets are gently swirled for a few seconds to disburse them in the liquid, then allowed to sit undisturbed for 1-10 minutes at room temperature. Where desired, the platelets can be gently agitated one or more times by swirling or pipeting during the rehydration period. In other embodiments, the platelets are rehydrated by direct addition of the rehydration buffer, then immediate gentle pipetting until complete dispersion is observed. The platelets then can be permitted to remain undisturbed for 1-10 minutes or more, either with or without one or more brief gentle periods of agitation. In other embodiments, passive rehydration can be used. Examples of passive rehydration include rehydration by exposure to rehydration buffer vapor, then exposure to the rehydration buffer liquid. The practitioner is well aware of various methods for rehydrating freeze-dried platelets, and any suitable method may be used.

It is evident from the above disclosure that the invention encompasses rehydrated platelets and methods of making them. The rehydrated platelets of the invention can possess all of the characteristics of platelets that are needed for normal blood clotting, when introduced into a subject in need of blood clotting functions. Yet they may also be lacking in one or more characteristic, which may be advantageous in performing diagnostic assays. Thus, the rehydrated platelets can be of the same size as fresh platelets. They also can have the same generally disc shape as fresh platelets and the same volume. The complement of molecules on the surface of the rehydrated platelets can be the same as that of fresh platelets, as can be the functions provided by these molecules. Accordingly, the rehydrated platelets can participate normally in the clotting process, both under in vitro conditions and when re-introduced to an in vivo environment.

Depending on the process used to create them, the rehydrated platelet preparations of the invention can contain few or many microparticles. In general, freeze-drying techniques known in the art result in freeze-dried platelets that, when reconstituted, provide adequate platelet functions. However, they typically result in high numbers of microparticles being present, ostensibly due to lysis of a large number of platelets during the freeze-drying and/or rehydration procedures. Unlike the freeze-drying methods in the art, certain of the present methods provide reconstituted platelet preparations with a relatively low number of microparticles. The high ratio of intact, properly sized platelets to microparticles in these embodiments is advantageous for use of the platelet preparations in therapeutic regimens. Furthermore, because the present invention provides insights into how to control the relative amounts of platelets and microparticles, compositions having a desired amount of each can be produced.

In another aspect, the invention provides a method of making a composition. In general, the method of this aspect of the invention comprises obtaining platelets and freeze-drying them. The method can further comprise rehydrating the platelets and/or adding one or more additional components to the platelets, before or after freeze-drying or rehydrating.

In certain embodiments, the method of making the compositions comprises providing a material that contains platelets and/or microparticles, removing all or essentially all red and white blood cells that might be present in the material, adjusting the pH of the resulting cell-free material to an acidic pH, separating platelets, microparticles, or both from all or essentially all other components present in the material, resuspending the platelets, microparticles, or both in a liquid, and lyophilizing. In embodiments, one or more agents that are typically included in lyophilization procedures, such as sugars, are added to the resuspended platelets and/or microparticles before lyophilizing. Exemplary sugars include, but are not limited to, monosaccharides, disaccharides (e.g., sucrose, lactose, maltose, isomaltose, cellobiose, and trehalose), or polysaccharides. In embodiments, the method comprises sterilizing the lyophilized material using any known technique that is suitable for sterilizing lyophilized materials, including, but not limited to, irradiation.

In a basic procedure for making a composition of the invention, platelets are suspended in a buffer comprising trehalose to give a concentration of about $1 \times 10^9$/ml. The composition is incubated at ambient temperature (about 20° C.-25° C.) for two hours, at which time, 5% (final concentration) bovine serum albumin or any other bulking proteins (such as Casein) or other cryoprotectant is added, and the platelets are lyophilized using a standard lyophilization protocol. Alternatively, in another basic procedure, 6.0% carbohydrates that can replace proteins as the bulking reagent, such as Ficoll-400 or any other bulking carbohydrate (such as hydrogels), is added (final concentration) and the platelets are lyophilized using a standard lyophilization protocol.

In accordance with the discussion above, the platelets can be obtained from any suitable source, can be indated or outdated, and can be autologous or heterologous (with regard to the platelets with which they are to be mixed in a method of the invention). Accordingly, they can be from random donors units or aphereisis units. The amount of platelets can be any suitable amount, such as those described above. In embodiments, the platelets are obtained from one or more blood donors, and are present in whole blood. It is preferable, however, that the platelets be purified, at least to some extent, from one or more other blood components. This is particularly so for freeze-dried platelets. Methods of purifying or isolating platelets from other blood components are well known to those of skill in the art, and thus need not be detailed here. In exemplary embodiments, platelets are purified from other blood components through a process that comprises centrifugation.

The step of obtaining can comprise any activity that results in removal of platelets from a donor's body and transfer of the platelets into a receiving vessel. Numerous techniques for achieving this result are known in the art, and any method or combination of methods is encompassed by the present invention. In certain embodiments, obtaining comprises drawing blood from a donor's vein and placing the drawn blood in a tube, such as one made of plastic or glass. This step is equivalent to the "providing" step discussed above, and each is interchangeable with the other.

Freeze-drying can be accomplished by any technique that is suitable for freeze-drying eukaryotic cells. Exemplary techniques are detailed herein. In general, freeze drying comprises exposing the cells to temperatures below 0° C. while applying a vacuum, and allowing the process of sublimation to remove all or essentially all of the water originally present in the platelets and their surroundings. The resulting platelets are in a solid (dry) form, and can be used in the methods of the invention, below, directly, or after rehydration.

The methods of making a composition may further comprise rehydrating (or reconstituting) the freeze-dried platelets. Rehydrating can comprise adding water or an aqueous solution to the freeze-dried platelets in an amount sufficient to restore at least one physical or biological property to the platelets. Rehydrating can be through any suitable method known in the art, including, but not limited to, direct addition of liquid water to the platelets, and slow vapor reconstitution. Aqueous solutions may comprise any substances that are compatible with platelet function in the amounts in which they are present in the compositions.

The methods of making a composition of the invention can further comprise combining the freeze-dried platelets with other platelets, to form a mixture. The other platelets may be freeze-dried platelets, or may be platelets that are present in a liquid composition, such as blood or a blood fraction (e.g., blood plasma). The mixture is typically, but not always, made in a reaction vessel in which clotting can be detected. That is, although it is possible to make the mixture in vivo by injecting the freeze-dried platelets into a body, typically, the freeze-dried platelets are combined with the other platelets outside of a body, such as in a reaction vessel suitable for detection of blood clots.

The method may further comprise adding one or more substances that have biological activity. For example, the method may comprise adding to a composition comprising the freeze-dried platelets one or more drug or other substance, which may have anti-platelet activity. Exemplary drugs and substances with anti-platelet activities are discussed above. The method may thus further comprise adding one or more biological molecules that have enzymatic activity. For example, the method may comprise adding to a composition comprising the freeze-dried platelets one or more coagulation proteins or other substance, which may attenuate platelet activity.

The method may further comprise adding one or more fluorescence molecules to the freeze-dried platelets. For example, the method may comprise adding to a composition comprising the freeze-dried platelets one or more fluorescein or other fluorescence substance, which may enhance the signaling of platelet activity.

For preparation of freeze-dried and reconstituted platelets, and compositions comprising them, it is preferred that the original platelets be from an indated source. However, in the situation where the supply of indated platelets are limited, outdate platelets can be used because the platelets produced using the current invention can be subjected to pathogen reduction and HLA reduction steps without compromising platelet functions. To provide the most advantageous results, outdated platelets should be used within 3 days out dated (i.e., by day 9 after removal from the donor). That is, if platelets are expired on the $5^{th}$ date, outdated platelets can be used on the $6^{th}$, $7^{th}$ or $8^{th}$ date using the procedure from the current invention.

It is to be understood that the invention comprises practice of a single method for producing platelets, microparticles, or both, and a single method for producing compositions. Each method may be adjusted to obtain the desired ratio of platelets to microparticles. It is also to be understood that the invention comprises practicing two or more different methods of producing freeze-dried platelets, each resulting in different ratios of platelets to microparticles, then combining the two resulting compositions in desired ratios to achieve the desired platelet to microparticle ratio.

Various modifications of the basic procedure, based on the parameters disclosed herein, can be made to either increase the relative amount of platelets as compared to microparticles, or to increase the relative amount of microparticles as compared to platelets. It has been found that increasing amounts of intact platelets improves the suitability of the compositions for in vivo infusion or injection treatment uses because the activation level of the composition is relatively low, and the composition shows a higher number of characteristics of normal, fresh or in-dated platelets. In contrast, where in vivo site-specific administration of clot-enhancing substances is desired, compositions comprising increasing amounts of microparticles are increasingly more desirable. It is believed that the increasing relative number of microparticles in the composition promotes faster clot times because it delivers increasing amounts of clot-promoting substances immediately, as compared to providing those substances by way of intact platelets, which might take extended periods of time to release them. Depending on the purpose of the diagnostic assay or research assay, one of skill in the art may select the appropriate method of making freeze-dried platelets to increase or limit the relative amount of microparticles in the composition comprising the freeze-dried platelets, or in the composition comprising rehydrated freeze-dried platelets.

The methods of the present invention provide advantages of prior methods of making freeze-dried platelets and compositions comprising them. One advantage is the ability to omit platelet activation inhibitors. Because incubation can be performed for shorter periods of time than used in prior art methods, the platelets are not necessarily activated, or if activated, only activated to a relatively low level. Thus, in embodiments of the methods of the present invention, it is not necessary to add platelet activation inhibitors to inhibit activation of the platelets while loading them with saccharides. This not only lowers the cost and complexity of the procedure, but eliminates the need to remove the inhibitors at a later time before use, such as prior to lyophilization or after rehydration.

The method of preparing freeze-dried platelets according to embodiments of the present invention provides platelets with intact surface receptors, such as Glycoprotiens IIb-IIIa and Glycoproteins Ib, that are involved in various platelet functions, such as adhesion to the subendothelial matrix to initiate and participate in the clotting process. The method of preparing freeze-dried platelets according to embodiments of the present invention also provides platelets with intact intracellular organelles, such as dense and alpha granules that are involved in various platelet functions, such as intracellular signaling, promotion of vasoconstriction, and release of molecules that further promote platelet activation and aggregation at the site of injuries. Accordingly, the method can be practiced on other non-nucleated eukaryotic cells or cell fragments, including, but not limited to, red blood cells. As used herein, the term "platelet" refers to such other non-nucleated eukaryotic cells and cell fragments. Likewise, the method can be practiced to prepare stabilized macromolecules or complexes of macromolecules, such as, but not limited to, proteins, nucleic acids, viruses, and the like. Indeed, because the methods of the present invention provide stabilized products that can be stored for extended periods of time in stable form at room temperature and without the need for refrigeration or freezing, it can be practiced on any number of biological or chemical substances, including those specifically mentioned herein and other like substances.

For example, in an embodiment, the method can comprise making a composition comprising microparticles. The method can comprise: pre-activating platelets with platelet agonists such as TRAP, collagen, thrombin, or ionophores, then incubating the platelets for about 30 minutes at 37° C. Doing so activates the platelets prior to loading and lyophilization, which increases the relative percent of microparticles in the freeze-dried composition. A specific exemplary protocol for generating compositions with high relative proportions of microparticles (in this case, about 60-90% microparticles) comprises: collecting PRP into tubes; centrifuging at 1000×g for 15 minutes; decanting the supernatant; suspending the pellet in 10 ml PBS containing 10 mM EDTA, pH 6.5, washing in PBSE, pH 6.5; resuspending the pellet in PMP buffer (137 mM NaCl, 4 mM KCl, 0.5 mM $MgCl_2$, 0.5 mM $Na_2HPO_4$, 5.5 mM glucose, 10 mM HEPES, 2 mM $CaCl_2$) to achieve a platelet concentration of $2.5 \times 10^9$ platelets per ml; adding 15 uM SFLLRN and incubating at 37° C. for 10 minutes; centrifuging the remaining pellets at 750×g for 20 minutes; removing the supernatant and centrifuging it at 10,000×g at 4° C. for 30 minutes; removing the supernatant and resuspending the PMP in the same volume of 150 mM trehalose buffer (0.0095 M HEPES, 0.05 M NaCl, 0.0048 M KCl, 0.012 M $NaHCO_3$, 0.15 M trehalose, 0.005 M glucose, pH 6.8); adding ¼ volume of 30% ficoll, aliquotting liquid into 0.5 ml portions; and lyophilizing.

On the other hand, the method of preparing freeze-dried platelets according to embodiments of the present invention can provide platelet-containing compositions with high levels of intact platelets as compared to microparticles and other substances resulting from lysis of platelets. Thus, like current techniques that rely on use of DMSO or formaldehyde to produce lyophilized or otherwise dried platelet preparations, the present invention can provide compositions with high levels of intact platelets. Yet, unlike the DMSO or formaldehyde protocols, there is no need to wash the reconstituted platelets of the present invention before use.

In assays for aggregation function, assayed by percent aggregation by single cell count, it was found that reconstituted platelets made by an embodiment of the invention (see Examples 1 and 2, below) had advantageous properties, as depicted in Table 1.

TABLE 1

Aggregation Characteristics of Reconstituted Platelets

| Agonist | % Aggregation by Single Cell Count |
|---|---|
| Arachidonic Acid | 77 |
| Collagen | 83 |
| Epinephrine | 86 |
| TRAP Peptide | 93 |
| Ristocetin | 97 |
| None | 10 |

When freshly prepared freeze-dried platelets and freeze dried platelets that had been stored at room temperature for 6 months were reconstituted and assayed for certain characteristics, it was found that they both had the following characteristics: adhesion to subendothelium matrix proteins; aggregation in response to various agonists; maintenance of primary receptors; function in concert with autologous platelets; procoagulant activity; retention of overall size and granulation; promotion of clotting in vitro in whole blood and plasma models; retention of functional activities upon heating and gamma irradiation treatment; and stability of greater than 90% (instantaneous reconstitution). Thus, freeze dried platelets that have been stored for 6 months at room temperature are expected to function in the same manner as freshly prepared freeze-dried platelets.

As for surface markers, reconstituted freeze-dried platelets of the present invention have been found to possess the levels of surface markers indicated in Table 2. If an HLA reduction step is incorporated in the method of preparing the platelets, the levels of HLA can be reduced to 5% (100%). These values compare favorably with the values that can be obtained using reconstituted freeze-dried platelets made by other methods known in the art. The results presented in Table 2 are based on reconstituted freeze-dried platelets made by a method of the present invention (see Examples 1 and 2, below) and fresh platelets.

TABLE 2

Expression of Selected Surface Markers on Freeze-Dried Platelets Prepared from Multiple Random Donor Units

| Surface Marker | Fresh Platelets | Example 2 Protocol | Example 1 Protocol |
|---|---|---|---|
| GP Ib | 100% | 65-75% | 5-10% |
| GP IIb/IIIa | 100% | 100% | 100% |
| HLA | 100% | 5% (w/acid reduction) 100% w/o acid reduction) | 100% |
| P-Selectin Resting | 5-10% | 80% | 100% |
| P-Selecting Active | 100-140% | 100% | 100% |

In different embodiments, the reconstituted platelets can have different levels of activation. Depending on various factors, including among other things the temperature and length of time of saccharide loading, the moisture content of the platelets after freeze-drying, and whether or not a post-lyophilization heat step is included, the platelets of the present invention have proved to show a range from low levels of activation to higher levels. By practicing the steps of certain embodiments of the invention, one can obtain freeze-dried platelets that, upon reconstitution, are not fully activated. This is a property unlike other platelet preparations provided by freeze-drying techniques known in the art. Thus, in embodiments, the reconstituted platelets of the invention show, upon visual inspection, swirled platelets. The swirly characteristic disappears upon exposure to agonists, such as arachidonic acid, collagen, epinephrin, TRAP peptide, and ristocetin. Furthermore, reconstituted platelets have been found to aggregate into a clot that can be detected visually upon exposure to the agonists. Additionally, the levels of surface marker GP Ib remains high (~60-100%).

Activated platelets cease to swirl and bind to the protein Annexin V. The surface of activated platelets express other proteins (such as P-selectin), and the levels of the surface protein GP Ib decrease to about 10% of the original levels. Only the expression of P-selectin and binding to Annexin V were detected on freeze-dried platelets of the present invention. Thus, based on these brief summaries, the reconstituted freeze-dried platelets tested for Table 2 retained most of the unactivated characteristics and some of the activated characteristics commonly found in normal platelets.

Thus, it is important to recognize that the current invention provides a method for long term preservation and storage of platelets in a dry format, where the platelets are easy to store and transport, and are convenient to use. It is also important to recognize that the current invention provides a protocol that stabilizes platelets and upon reconstitution with suitable buffer, provides functional platelets. It is to be understood that the processes disclosed herein will also confer non-nucleated eukaryotic cells with biological capabilities similar to fresh platelets. It should be understood that the present methods constitute novel methods to maintain non-nucleated eukaryotic cells and cell fragments in the dry state while maintain their biological functions upon reconstitution. Likewise, the methods of the present invention can be used to freeze-dry less complicated biological material, such as lipids, lipid vesicles, viral particles, viral coats, proteins, and nucleic acids.

The freeze-dried platelets and rehydrated freeze-dried platelets of the invention are suitable for many uses. Indeed, because they can have characteristics of fresh or in-dated platelets, they can be used for any therapeutic purpose that fresh or in-dated platelets would be used for. For example, the rehydrated platelets of the invention can be used as a blood substitute or supplement for treatment of excessive bleeding, such as that seen in wounded subjects or subjects undergoing surgery. Furthermore, the freeze-dried platelets can be included as part of a wound-healing bandage (for example, about $1\times10^8$-$1\times10^9$ platelets per $cm^3$) to provide platelet functions to sites of wounds. They likewise can be used to treat disorders relating to reduced or missing platelet function. In addition, because the platelets can have characteristics of fresh or in-dated platelets, they can be used in diagnostic assays to determine various functions of the blood clotting system of subjects. Furthermore, they can be used in research settings to elucidate the characteristics of platelets, to study the clotting cascade, and to identify cellular components that are involved in blood hemostasis and other biological functions.

In a further aspect, the invention provides kits. In general, kits of the invention comprise freeze-dried and/or reconstituted platelets of the invention. In view of the shelf stability of freeze-dried platelets of the invention, preferred kits comprise freeze-dried platelets. Kits typically comprise sufficient amounts of platelets to perform at least one embodiment of a method according to the invention.

In its simplest form, a kit according to the invention is a container containing freeze-dried platelets, reconstituted freeze-dried platelets, or at least one composition according to the invention. Thus, in embodiments, the kit of the invention comprises a container containing freeze-dried platelets. In embodiments, the kit comprises a container containing reconstituted freeze-dried platelets. In embodiments, the kit comprises a container containing a composition of the invention that comprises freeze-dried platelets or reconstituted freeze-dried platelets. In embodiments, the kit comprises human freeze-dried platelets.

In certain configurations of the kit, the kit comprises multiple containers, each of which may contain freeze-dried platelets, reconstituted freeze-dried platelets, a composition comprising freeze-dried platelets or reconstituted freeze-dried platelets, or other substances that are useful for performing one or more embodiment of a method of the invention. In embodiments where the kit comprises additional components or substances, they may be contained in the same or one or more different containers as the platelets and/or compositions. Where the kit comprises multiple containers or one container and other components, the containers and components are said to be in packaged combination within the kit. Where multiple containers are present, each container may contain enough platelets for practice of a single method of the invention, such as containing a single dosage for treatment. Alternatively, each container may contain enough platelets for practice of a method two or more times, such as containing two or more dosages. The various containers may contain differing amounts of the platelets and/or compositions of the invention.

In embodiments, the kit comprises other components, such as purified components of the clotting cascade, etc. The kit can further comprise some or all of the supplies and materials needed to prepare and administer the compositions of the invention, such as large-bore needles and syringes, pumps, sterile cloths and solutions for sterilizing sites of injection, etc. In embodiments, the kits comprise one or more liquid to hydrate the compositions of the kits. The liquid may be any suitable liquid, but is typically a water-based liquid, such as water, saline, or a mixture of the two. Preferably, the liquid is sterile. Thus, the kits can be diagnostic kits, blood clotting monitoring kits for coagulation proteins or platelets, or drug treatment monitoring kits.

Accordingly, the kit can be configured to supply freeze-dried platelets or reconstituted freeze-dried platelets (or compositions comprising them) for use in in vivo treatments, for use in in vitro diagnostics, or for use in in vitro or in vivo research. Thus, regardless of the state of hydration of the platelets, in embodiments, the kit comprises multiple containers, each of which may contain the platelets or other substances that are useful for performing one or more diagnostic protocol, one or more treatment protocol, or one or more research experiment. In other embodiments, the kit comprises additional components, which may be contained in the same or one or more different containers. Often, the kits will comprise some or all of the supplies and reagents to perform one or more control reactions to ensure the kits are performing properly and to provide baseline results against which test samples can be compared.

Like the compositions it holds, in its various forms, the kit of the invention can comprise substances that are useful for study of platelets, such as in vitro studies to detect and/or study various platelet characteristics and functions; to calibrate instruments; to isolate and purify platelet cytoplasmic molecules or platelet granules (alpha and dense granules); to study platelet and microparticle interactions among themselves and with other components of the blood clotting system; to study anti-platelet medications and platelet or coagulation inhibitors; for calibrating platelet size; for calibrating differential gradient separation techniques; as research tools to examine the interaction of platelet receptors and their ligands; to study surface mediated enzymatic reactions, including but not limited to tenase complex, prothrombinase complex, and the like; to study platelet aggregation, whether mechanical or biochemically induced; to study platelet biology and storage; to isolate platelet-related surface molecules; to determine platelet inhibitors that can be tailored to individuals; to study neuropsychopharmacology; to study inflammation, coagulation, cellular repair, and regeneration; to study neo-antigenicity in platelet therapies; to characterize non-MHC antigens that promote immune responses against blood cells; to study the effect of blood-borne pathogens; to image normal and damaged blood vessels; and to study angiogenesis, atherosclerosis, thrombosis, and cardiovascular disease.

The container can be any material that is suitable for containing the platelets or compositions of the invention, such as a vial or ampule. It can be fabricated from any suitable material, such as glass, plastic, metal, or paper or a paper product. In embodiments, it is a glass or plastic ampule or vial that can be sealed, such as by a stopper, a stopper and crimp seal, or a plastic or metal cap such as a screw cap. In general, the container and seal are made of materials that can be sterilized by heat (dry or wet), radiation (UV, gamma, etc.), or exposure to chemicals. Preferably, the container is sterilized before the platelets or compositions of the invention are introduced into the container. Typically, the container will be of sufficient size to contain the platelets or a composition of the invention, yet have head space to permit addition of additional substances, such as sterile water or saline or a mixture of the two, which can be used to rehydrate the platelets or composition in the container. In embodiments, the container comprises a sufficient amount of platelets to perform at least one embodiment of a method according to the invention. Thus, in embodiments, the container contains a sufficient amount of platelets for one dosage, two dosages, or even more, for treatment of an individual suffering from bleeding or a bleeding disorder, or a sufficient amount of platelets for at least one diagnostic assay. The amount of platelets contained in the container can be selected by one of skill in the art without undue experimentation based on numerous parameters, including, but not limited to, the weight of the patient, the type of bleeding or bleeding disorder being treated, the number of dosages to be administered in a given amount of time (e.g., in the 24 hour period following hydration of the composition), and the sensitivity of diagnostic equipment.

In embodiments, the container is provided as a component of the kit, which includes suitable packaging and, optionally, instructions and/or other information relating to use of the contents of the kit. Typically, the kit is fabricated from a sturdy material, such as cardboard or plastic, and can contain the instructions or other information printed directly on it. In embodiments, the container or kit comprises other components, such as one or more purified components of the clotting cascade, drugs affecting the clotting cascade, one or more applicators, one or more coverings or coatings for the site of administration of the platelets, and the like. The kit can comprise multiple containers containing the platelets and/or compositions of the invention. In such kits, each container can be the same size, and contain the same amount of platelets or composition, as each other container. Alternatively, different containers may be different sizes and/or contain different amounts of platelets, composition(s), or compositions having different constituents. One of skill in the art will immediately appreciate that numerous different configurations of container sizes and contents are envisioned by this invention, and thus not all permutations need be specifically recited herein.

Although any suitable amount of platelets may be provided in each particular container in a kit, or in a kit in total, for in vivo therapeutic purposes in which platelets are administered directly to a site of bleeding, the kit will typically comprise at least one container containing at least or about $1\times10^8$ to $1\times10^{11}$ platelets. In embodiments, at least one container contains at least or about $1\times10^8$ platelets, $1\times10^9$ platelets, $1\times10^{10}$ platelets, or $1\times10^{11}$ platelets. For in vivo therapeutic purposes in which platelets are administered as an infusible or injectable hemostat, at least one container typically will contain at least about $1\times10^8$ to $1\times10^9$ platelets. Likewise, for in vitro diagnostic or research purposes, at least one container typically will contain at least about $1\times10^8$ to $1\times10^9$ platelets. It is to be noted that the amounts mentioned above are typical amounts for each container, and other amounts, higher or lower, are also contemplated. Thus, in embodiments, the kits provide platelets in a sufficient amount to treat a subject in need of platelets, such as a patient undergoing surgery or having a bleeding wound. For example, the kit can comprise one or more vials containing $1\times10^8$ to $1\times10^9$ platelets each for wound therapy. A treatment regime using such a kit could comprise administering the platelets (after rehydrating) in 10 doses. In other embodiments, platelets are provided in the kit in a sufficient amount to perform studies on platelets or the blood clotting system of the species of animal from which the platelets originate. In yet other embodiments, platelets are provided in the kit in a sufficient amount to perform at least one diagnostic assay for at least one function of the blood clotting system, such as a platelet function. For example, a kit for diagnostic purposes could comprise multiple vials, each containing from 200,000 to 1,000,000 platelets. In certain embodiments, the kit is simply a container containing an amount of freeze-dried platelets equivalent to the amount of platelets in one liter or one pint of blood.

In an additional aspect, the present invention provides a method of treating a subject in need of platelets or one or more platelet functions. In general, the method comprises obtaining platelets, platelet-derived microparticles, or both; and administering them to a subject in need of platelets or one or more platelet functions. An advantageous characteristic of this aspect of the invention is that it provides different embodiments that have different applications. Overall, the methods can be understood to comprise administering platelets or a composition of the invention to an individual in an amount sufficient to raise the hemostatic properties of that individual's blood to a level that is detectably higher than it was before administration. Thus, the methods of the invention generally comprise administering a composition of the invention to an individual such that an amount of platelets sufficient to overcome the deficiencies of the disease or disorder, or the wound or trauma, afflicting the individual is delivered to the individual. For example, in embodiments, it provides methods of using the platelets, microparticles, and/or compositions to treat injuries or wounds involving bleeding, where the platelets, microparticles, and compositions are capable of being administered to a patient in need by direct application (such as by topical administration) rather than as an infusion of fresh or indated platelets, as is typical in the alt. On the other hand, it provides methods of using the platelets, microparticles, and/or compositions to treat injuries or wounds involving bleeding, where the platelets, microparticles, and/or compositions are capable of being administered to a patient in need by infusion or injection of the freeze-dried platelets, microparticles, or compositions, rather than by infusion of fresh or in-dated platelets, as is typical in the art.

To the knowledge of the inventors, for the first time, this invention provides use of freeze-dried platelets for in vivo therapeutic purposes. It also provides for use of rehydrated freeze-dried platelets for in vivo therapeutic purposes. Likewise, it provides for use of freeze-dried microparticles and rehydrated freeze-dried microparticles for in vivo therapeutic purposes. It has unexpectedly been found that rehydrated freeze-dried platelets, when administered to individuals manifesting the clinical attributes of various forms of hemophilia or drug-induced coagulopathy, reverses the clinical effects and thus reduces the time required for clotting in these individuals. This is surprising because such individuals typically do not exhibit low platelet counts or abnormal platelet function.

According to the method of treating, administering can be by direct application of the platelets or one or more compositions to a site of bleeding. Likewise, it can be by direct application of the platelets or one or more compositions to a site immediately adjacent to the site of bleeding. Thus, it can be by providing platelets, microparticles, or compositions in a bandage or other carrier, which can be placed in contact with the site of bleeding. It can also be by infusion of platelets or one or more compositions into the blood system of the subject being treated. Alternatively, it can be by injection of platelets or one or more compositions into the blood system of the subject being treated.

The methods of the invention can be used to treat wounds or injuries that involve bleeding. They also can be used in various other treatments, as mentioned herein. The bleeding can be due to anything, but is typically due to injury or other trauma (including surgery) or a bleeding disease or disorder. The methods can be used to completely stop bleeding by, for example, forming a clot at the site of bleeding, or they can be used to promote wound healing by reducing the amount of bleeding at a site, in some instances acting as an adjunct or aid in the clot forming process provided by the patient's blood system.

The subject can be any subject in need of platelets or one or more platelet functions. For example, the subject can be one that is suffering from a bleeding wound or one who has a bleeding disease or disorder. The subject or patient can be an animal, such as a companion pet (e.g., dog, cat, rodent, bird) or a farm animal (e.g., cow, sheep, horse, goat, chicken). It can also be a laboratory animal, such as a rodent (e.g., rat, mouse), a rabbit, or a monkey. It can be a human. In general, it can be any animal, including, but not limited to, mammals.

The present invention includes the dual use of a mixture of freeze-dried, processed platelets and platelet microparticles, or rehydrated platelets and microparticles obtained or derived from them. Thus, in one facet, the platelets and compositions of the invention can be used as non-infusible hemostatic agents that can be used to rapidly stop bleeding in not only low pressure areas of the vasculature, but in high pressure areas as well, such as the abdominal aorta artery, femur artery, carotid artery, and other blood vessels that are not amenable to the current means of hemostatic controls, such as manual compression and/or tourniquet applications.

Various embodiments, the invention provides compositions and methods of treating that embody the concepts of: a composition comprising freeze-dried platelets, freeze-dried microparticles, or a combination of freeze-dried platelets and freeze-dried microparticles, and the use of such compositions, including derivatives and modifications thereof, in any form, including as freeze-dried powder, an aerosol system, vapor mists, bandages, and the like, for treatment of an injury or wound involving bleeding by applying the composition to the injury or wound; a composition and use thereof as a hemostat agent to arrest bleeding, including heavy bleeding, from low pressure and/or high pressure blood vessels such as, but not limited to, abdominal aorta arteries, coronary arteries, femur arteries, carotid arteries, hepatic arteries, celiac arteries, renal arteries, iliac arteries, and other blood major vessels, where the hemostat agent is administered directly at or near the site of bleeding, and not administered at a distant site, such as would be the case with infusion and systemic delivery of a composition; and a composition of the invention, derivatives and any modifications thereof, to be used as a non-infusible hemostat agent in a method of treatment to apply to surgical/trauma sites to decrease total blood loss and reduce the need for blood transfusions. The invention also provides compositions and methods of treating that embody the concepts of: a composition, derivatives and any modifications thereof, to be used as a non-infusible hemostat agent to apply to control bleeding in congenital or acquired coagulopathy; a composition, derivatives and any modifications thereof, to be used as a non-infusible hemostat agent to apply to control bleeding in patients on anti-thrombotic medications; a composition, derivatives and any modifications thereof, to be used as a sealant to be applied in invasive surgeries such as, but not limited to, splenic, hepatectomy, duodenopancreatectomy, and cholecystectomy, to control bleeding and accelerate tissue regeneration; a composition, derivatives and any modifications thereof, to be used as topical/wound healing application for pathological conditions, such as, but not limited to, diabetic ulcers, cutaneous ulcers, and other non-healing wounds. The invention further provides compositions and methods of treating that embody the concepts of: a composition, derivatives and any modifications thereof, to be used as an agent to accelerate topical wound healing; a composition, derivatives and any modifications thereof, to be used as an agent to reduce scar formation; a composition, derivatives and any modifications thereof, to be used as an agent for anastomosis indications; and a composition, derivatives and any modifications thereof, for the treatment of conditions that are associated with impaired or inappropriate angiogenesis, and diseases involving the vasculature or endothelial cells. These can be, but are not limited to, age-related macular degeneration, coronary artery disease, peripheral vascular disease, islet cell transplantation, fracture and tendon repair, reconstructive surgery, tissue engineering, restenonsis, cancer, diabetic retinopathy, rheumatoid arthritis, psoriasis, hemangiona/AIDS-related Kaposi's sarcoma, atherosclerotic plaque rupture, and the like. Thus, among many uses, the compositions of the invention can be used both as hemostatic agents and to accelerate the process of wound healing.

Accordingly, the present invention provides methods of using the platelets, microparticles, and compositions, such as methods of treating a subject in need of at least one blood clotting component, for the in vivo and in vitro purposes discussed herein.

In embodiments, the invention provides methods of treating subjects who are in need of, or are suspected of being in need of, one or more components of the clotting system of normal blood. Because the platelets of the invention provide at least one factor that is sufficient to overcome the deficiencies of forms of hemophilia and treatment-induced coagulopathy, the compositions of the invention can be used to treat individuals suffering from hemophilia or forms of coagulopathy. In general, the methods comprise administering the composition of the invention to an individual in an amount sufficient to raise the hemostatic properties of that individual's blood to a level that is detectably higher than it was before administration. Thus, the methods of the invention generally comprise administering a composition of the invention to an individual such that an amount of platelets sufficient to overcome the deficiencies of the disease or disorder afflicting the individual is delivered to the individual.

In embodiments, the methods treat individuals suffering from hemophilia. The hemophiliac can be suffering from Hemophilia A, Hemophilia B, Hemophilia C, or Acquired Hemophilia with Inhibitors. Likewise, any level of hemophilia (total, severe, or moderate) can be treated according to the methods of the invention.

In other embodiments, the methods treat patients who are undergoing treatment with anticoagulant agents or other agents or therapies that cause clotting systems to be compromised. Thus, in embodiments, the methods are methods of treating chemotherapy-induced blood clotting disorders, radiation-induced blood clotting disorders distinct from thrombocytopenia, or blood clotting coagulation disorders resulting from exposure to one or more detrimental environmental agents. It is preferred that the compositions of the invention are administered in amounts that result in platelet counts not exceeding the resting platelet count by two fold. In other words, if the recipient has a baseline count of 200,000 platelets/ul, then the product should be administered in doses of about $10^{11}$ platelets, this dose being designed to increase baseline counts by about 50,000 platelets/ul per dose. Two or more doses may be needed to achieve hemostasis, depending upon the nature, location, and severity of the bleed.

The present invention thus contemplates the use of the platelets of the invention for treatment of bleeding disorders, particularly those in which the patient's platelet counts are normal or not considered clinically abnormal. Thus, the invention contemplates the use of the platelets of the invention for treatment of all forms of Congenital Hemophilia, Hemophilia with Inhibitors, Acquired Hemophilia, and drug-induced coagulopathy. It further contemplates the use of the platelets for the neutralization of heparin, for example, during interventional cardiology procedures, and as an antidote for low molecular weight heparins and direct or indirect Factor Xa inhibitors. The invention is further applicable in the use of the platelets in an adjunctive therapy for enhancing the efficacy of recombinant Factor VIIa. It likewise finds use in the treatment of acquired Factor X deficiency, for example during light chain amyloidosis. It can also find use in treatment of coagulation factor deficiencies other than that of Factor II (prothrombin) or Factor I (fibrinogen). The invention and disclosed platelets may also find use in treatment of transient coagulopathy occurring as a result of hepatic dysfunction, such as that associated with liver failure or liver transplantation, and as a result of kidney failure, which can result in uremia. Additional applications of the platelets of the invention include use in treatments (e.g., as an antidote) for GPIIb/IIIa antagonist therapy and in treatment of vWD.

The methods of the invention can thus further comprise administering a composition of the invention a second or multiple times. Therefore, the methods of the invention encompass treatment regimens in which administration is repeated one or more times. Successive administrations may include the same amount of platelet derivatives or a different amount, and may include additional components or not. The choice of amounts and composition components can be selected by those of skill in the art based on various parameters, such as subject age, weight, medical history, clinical presentation, ancillary medical presentations, and the like. It is well within the skill of those in the art to make appropriate changes and adjustments to treatment regimens without undue experimentation. Thus, methods of the invention may comprise multiple administrations of compositions of the invention, each administration separated by a predetermined amount of time. For example, for prophylactic treatment of hemophilia, a composition of the invention may be administered once a week or once every two weeks. Other suitable regimens will be apparent based on the disease or disorder being treated.

The method can farther comprise administering other biologically active agents, such as clotting factors, and chemotherapeutic agents for treatment of cancer. It can also comprise treatment with physical modalities, such as with radiation. There are numerous and varied additional treatments that will be evident to those of skill in the art, and any such treatments can be included in the methods of the present invention.

The methods can comprise the optional step of rehydrating the freeze-dried platelets and/or microparticles prior to administering them to the subject.

One aspect of the invention is the use of non-autologous blood products as the source for the compositions of the invention. More specifically, platelet-based hemostat products currently available for use in treating bleeding use blood drawn from the patient in need of the treatment (i.e., autologous blood donations). The present invention does not require autologous donation of the source for the compositions of the invention. Indeed, the present invention need not even rely on fresh or in-dated platelets. That is, it has been surprisingly discovered that out-dated platelets, such as those between six and nine days post-donation, can provide suitable platelet functions when provided as freeze-dried platelets, freeze-dried platelet compositions (which can or might not comprise significant amounts of microparticles), or compositions comprising rehydrated freeze-dried platelets.

In view of the methods of the invention, the invention provides for the use of the compositions of the invention in the preparation of therapeutically effective compositions or formulations. These compositions or formulations can be used to treat bleeding as well as to treat hemophilia or other diseases or disorders that result in lack of normal clotting, or that involve low or absent levels of one or more clotting factors. Accordingly, the invention provides for the use of the compositions or formulations of the invention in the treatment of hemophilia or other diseases or disorders characterized by low or absent levels of one or more clotting factors. Other non-limiting exemplary embodiments include the use of platelet derivatives for the treatment of bleeding diathesis associated with liver damage, liver failure, or liver transplantation, as well as kidney failure (uremia).

An efficient and effective hemostatic agent used to treat inherited or acquired bleeding disorders must provide rapid control of bleeding to prevent unacceptable blood loss due to injury or surgery, and to minimize concomitant injury to other sites of the body, due to invasion of microbes or activation of blood proteins that negatively affect other body tissues, including joints. The present invention addresses the needs of the art in this regard by providing compositions and methods for treating individuals in need of one or more factors involved in the clotting process. Included among the diseases and disorders that can be treated according to the present invention are all forms of hemophilia, including Hemophilia A, Hemophilia B, Hemophilia C, and Acquired Hemophilia with Inhibitors; and insufficient clotting due to treatment with anticoagulant therapy. The invention is predicated, at least in part, on the discovery that platelet derivatives can be used to treat clotting disorders in persons having completely normal platelet counts and platelet function. The present invention uses various forms of platelets as an active agent to provide normal or pseudonormal hemostasis properties to hemophiliacs and others in need, and to provide hemostatic properties to hemophiliacs and others in need who are subject to traumas resulting in bleeding. Thus, in preferred embodiments, the invention provides freeze-dried (lyophilized) trehalose-stabilized platelets for the treatment of drug-induced coagulopathy, and for the accelerated efficacy of procoagulant drugs. According to the invention, clotting is promoted, at least in part, because the platelets contain a natural negatively charged phospholipid surface, which facilitates binding of endogenous factors, such as vitamin K-dependent clotting factors (i.e., Factors II, VII, IX, and X).

In preferred embodiments, the invention uses lyophilized procoagulant platelets and platelet derivatives to generate or accelerate clot formation, putatively by binding coagulation factors to the platelet derivative surface and thereby accelerating thrombin generation and clot formation. While not being limited to any particular theory, the currently available data is consistent with the theory that one or more coagulation proteins are either derived internally from platelet storage granules, i.e., platelet derived, or bound externally from plasma, i.e., plasma derived prior to lyophilization.

The invention further encompasses the use of platelets and rehydrated platelets for the reversal of drug-induced coagulopathy, especially those induced by Aprotinin (Trasylol®, Bayer) or heparin, both commonly used during cardiopulmonary bypass surgery. Accordingly, the invention encompasses treatment of patients who are undergoing or who have recently undergone anticoagulant therapy.

The system putatively functions by supplying a missing clotting factor or missing clotting factors directly on the platelet surface, where it can either overcome an absent clotting factor or directly bypass the effect of an antibody inhibitor or defective coagulation protein, thereby promoting hemostasis.

Among the many advantages provided by the present invention, one advantage is cost savings and availability. It is known that most therapies for hemophiliacs cost about $10,000 for each effective dose. Thus, hemophiliacs typically spend greater than $100,000 annually for treatment of this disorder.

In another aspect the present invention provides methods of using the freeze-dried platelets or reconstituted platelets derived therefrom for diagnostic or research purposes. The methods of diagnosis are typically performed in vitro, but may be performed in vivo on test animals if desired. The methods of diagnosis generally are performed to identify bleeding disorders and causes of those disorders. Research methods generally relate to discovery of causes of bleeding disorders, such as the molecular basis for a particular person's inability to normally control bleeding in response to wounds or other injuries. The research methods can also relate to study of the effects of drug treatments on the blood clotting system of individuals (e.g., side effects that negatively affect blood clotting) or on the process of blood clotting in general or specifically in regard to one or more particular steps in the process.

In methods of diagnosis, the methods can be methods of diagnosing a disease or disorder of the blood clotting system. These methods generally comprise obtaining freeze-dried platelets, combining the freeze-dried platelets with platelets and/or plasma removed from a patient having, or suspected of having, a disease or disorder of the blood clotting system to form a mixture, and determining whether the person has a defect in the blood clotting system by assaying one or more biological or biochemical functions of the mixture, where the defect decreases or abolishes the patient's blood clotting system's ability to function normally or to cause clot formation in a pre-defined period of time. Typically, determining whether the patient's blood clotting system is defective comprises assaying clotting time of the mixture. The freeze-dried platelets may be rehydrated prior to use.

The freeze-dried platelets may be obtained from one or more donors with a known status with respect to the clotting system (e.g., having a fully functional clotting system, or having a defect in one or more clotting factors). When the freeze-dried platelets are obtained from mixtures of platelets from a public blood bank, they can be assumed to be "normal" or "fully functional" with regard to platelet function. Alternatively, the freeze-dried platelets may be obtained from a patient undergoing or about to undergo a treatment regimen that might affect platelet function. Likewise, the freeze-dried platelets can be obtained from a patient who has completed a treatment regimen that has, or might have, affected platelet function (whether the patient had completed the full treatment regimen or was removed from the regimen early due to adverse side-effects).

Like the freeze-dried platelets, the fresh platelets or plasma may be obtained from one or more donors with a known status with respect to the clotting system (e.g., having a fully functional clotting system, or having a defect in one or more clotting factors). When the fresh platelets or plasma are obtained from mixtures from a public blood bank, they can be assumed to be "normal" or "fully functional" with regard to platelet function or plasma complement. Alternatively, the fresh platelets or plasma may be obtained from a patient undergoing or about to undergo a treatment regimen that might affect platelet function. Likewise, the fresh platelets or plasma can be obtained from a patient who has completed a treatment regimen that has, or might have, affected platelet function (whether the patient had completed the full treatment regimen or was removed from the regimen early due to adverse side-effects).

Regardless of the source of the freeze-dried platelets and the fresh platelets or plasma, the method comprises combining the two to make a mixture. The mixture is then assayed for one or more biological or biochemical functions of the mixture. Preferably, one or more functions of the clotting system, such as the ability to aggregate, are assayed. Comparison of the level of function or activity of the chosen functions or activities to "normal" levels permits one to determine if there is a difference in the levels. A difference in the levels indicates the presence of a disease or disorder of the blood clotting system.

In exemplary embodiments, the method comprises combining freeze-dried platelets that were obtained from a public blood bank with fresh platelets that were removed from a patient having, or suspected of having, a disease or disorder of the blood clotting system to form a mixture, and determining whether the person has a defect in the blood clotting system by assaying one or more biological or biochemical functions of the mixture. According to this aspect of the invention, the defect, if present, decreases or abolishes the patient's blood clotting system's ability to function normally or to cause clot formation in a pre-defined period of time.

In other exemplary embodiments, the method comprises combining freeze-dried platelets obtained from a patient prior to initiation of a treatment regimen with fresh platelets or plasma obtained from the patient at one or more times during or after completion of the treatment regimen to form a mixture. The method further comprises determining the clotting ability of the mixture(s), the ability indicating whether the treatment regimen induced a disease or disorder of the clotting system, or exacerbated an underlying, but never recognized, disease or disorder of the clotting system of the patient.

The freeze-dried platelets and platelets from the patient may be provided from any source, in accordance with the discussion above. Combining of the two can be by any suitable method, such as those well known in the art for combining two eukaryotic cells. Furthermore, determining whether the patient has one or more defect in the blood clotting system can be accomplished by any suitable technique, as discussed above.

In embodiments, determining comprises detecting the presence or amount of aggregation of platelets in the mixture. In general, low levels of aggregation indicate a defect or deficiency in blood clotting activity, whereas high levels of aggregation indicate normal or acceptable levels of activity.

Typically, determining whether the patient's blood clotting system is defective comprises assaying clotting time of the mixture.

The method can comprise other steps in addition to the basic steps disclosed above. For example, the method can comprise obtaining freeze-dried platelets prior to combining them with blood. In embodiments, the freeze-dried platelets are obtained from the patient for whom the assay is being performed, and are platelets that were obtained at an earlier time, such as prior to initiation of a drug regimen. The method can also comprise adding one or more drugs or other substances, which have a known effect on platelets or other participating cells or molecules of the clotting system, to the platelets, and determining the effect of the addition on clotting function. By selecting specific drugs with known activities, it is possible to determine the precise cause of the disease or disorder. With such knowledge, appropriate treatment regimens may be implemented.

In certain applications, the methods can be methods of monitoring the progression of a disease or disorder of the blood clotting system. These methods generally comprise obtaining freeze-dried platelets, combining the freeze-dried platelets with platelets and/or plasma removed from the patient suffering from the disease or disorder to make a mixture, and determining the blood clotting ability of the mixture. Typically, determining the blood clotting ability of the mixture indicates the blood clotting ability of the patient's blood, and comprises assaying clotting time of the mixture. Furthermore, typically, multiple assays are performed over time to give an indication of progression over time. By comparison of two time points, one can determine if a change in the status of the disease or disorder (if present) has occurred between the two time points. This information can, among other things, aid a doctor or patient in deciding whether to continue a particular treatment regimen. The freeze-dried platelets may be rehydrated prior to use.

The methods may also be methods of monitoring the effects of a treatment regimen for a patient on the blood clotting system of that patient. In general, these methods comprise obtaining freeze-dried platelets, combining the freeze-dried platelets with platelets and/or plasma removed from the patient undergoing the treatment regimen to make a mixture, and determining the blood clotting ability of the mixture. Typically, determining the blood clotting ability of the mixture indicates the blood clotting ability of the patient's blood, and comprises assaying clotting time of the mixture. Furthermore, typically, multiple assays are performed over time to give an indication of the effects of the treatment regimen over time. The freeze-dried platelets may be rehydrated prior to use.

Thus, in embodiments, the invention provides methods of monitoring the effects of a treatment regimen for a patient on the blood clotting system of that patient. In general, the methods comprise combining freeze-dried platelets and fresh platelets two or more times (for either or both of the freeze-dried platelets, the fresh platelets, and/or the plasma), and determining if a disease or disorder of the blood clotting system is present in the person from whom the freeze-dried platelets or fresh platelets or plasma are obtained. By comparison of two time points, one can monitor the effects of a treatment regimen on the blood clotting system of that person. In this method, either the freeze-dried platelets, the fresh platelets or plasma, or both, can be obtained from the same person (i.e., the patient). The information obtained by comparison of two or more time points can, among other things, aid a doctor or patient in deciding whether to continue a particular treatment regimen.

In another implementation, the invention provides a method of monitoring one or more functions of platelets. In general, the method comprises obtaining freeze-dried platelets, exposing them to one or more substance that can have an effect on platelet function, and determining whether the substance affected one or more function of the platelets. The method can further comprise reconstituting the freeze-dried platelets before, during, or after exposing them to the substance(s). Obtaining freeze-dried platelets and reconstituting them can be achieved by any of the methods discussed above or known in the art as suitable for such purposes.

Determining the effect of the substance(s) on platelet function can be by any of a wide range of techniques known to those of skill in the art. Such techniques are well known to those of skill in the art, and thus need not be detailed here. Exemplary techniques for determining the effect of the substance(s) on the platelets include, but are not limited to, techniques that assay the ability of the platelets to participate in clot formation (also referred to herein as aggregation when in an in vitro assay). Aggregation can be determined by the amount of light scattering by a composition, and can be determined using a simple photovoltaic cell or a dedicated aggregometer. Molecules that can be used to detect aggregation include, but are not limited to, epinephrine, ADP, thrombin, Thrombin Receptor Activating Peptide (TRAP), collagen, and thromboxane.

Determining the effect of the substance(s) on platelet function can comprise detecting the amount of aggregation of platelet-containing compositions that comprise both freeze-dried platelets and fresh platelets. As discussed in more detail below, the freeze-dried platelets of the present invention have many, if not all, of the functional characteristics of fresh platelets. However, many of the functions are present at levels that are insufficient to promote clotting. Interestingly, although such functions may be at levels insufficient to promote normal levels of clotting, the freeze-dried platelets can participate in normal or near normal clotting if other platelets are present that can provide the insufficient function. Thus, in embodiments, the fresh platelets provide one or more functions that are insufficient or lacking in the freeze-dried platelets, and detection of clotting is possible.

The fact that, in embodiments of the invention, the freeze-dried platelets of the invention have a reduced ability to clot without the aid of other platelets, such as fresh platelets, provides an advantage not provided by fresh platelets alone. In effect, this characteristic makes the freeze-dried platelets, and combinations of freeze-dried platelets and fresh platelets, more sensitive to inhibitors of the clotting system and sensitive to defects in the clotting system. Thus, by use of freeze-dried platelets, one may assay for defects in the clotting system. The assays of the system, and particularly the freeze-dried platelets, allow users to modulate the clotting system of a test sample and make a system that is highly sensitive to small changes in coagulation ability.

Furthermore, combining a pre-determined amount of freeze-dried platelets taken from a donor prior to therapy that affects platelet function with a pre-determined amount of fresh platelets taken from the donor taken after commencement of the therapy (e.g., during or after cessation of the therapy) will create a composition having clotting properties that are equal to or greater than the fresh platelets alone. In effect, this makes the combination of freeze-dried and fresh platelets more sensitive to inhibitors of the clotting system, and makes the combination sensitive to defects in the clotting system. Thus, by use of a composition comprising both freeze-dried platelets and fresh platelets, one may assay for defects in the clotting system with more sensitivity than with fresh platelets alone.

In embodiments of the invention, the freeze-dried platelets preserve the surface markers of fresh platelets. In effect, this makes the platelets sensitive to defects in Glycoprotein IIb/IIIa, Glycoprotein Ib, von Willebrand Factor, and fibrinogen, among other defects. It also makes the platelets more sensitive to Afibrinogenemia, Thromlasthenia, vWF disease, Bernard Souleir Syndrome, Receptor Defects Deisorders of Secretion/signal transduction, Storage Pool Deficiency, Diminished Thromboxane Synthesis, Signal Transduction/Primary Secretion Defects, and Deficiency of Platelet Coagulant Activities. Thus, by use of freeze-dried platelets, one may assay for platelets defects and defects in the clotting system.

The method of monitoring can comprise obtaining multiple samples from one donor and comparing the samples to each other and/or to a standard curve, to determine the presence and/or level of function of one or more platelet functions. The samples may be obtained over time, and the comparison made to determine the effect of one or more treatment regimens on platelet function or the clotting system in general. They also may be analyzed to confirm that there are adequate numbers of platelets in the donor's blood to support surgery or other procedures where blood might be lost. The samples that are obtained may be stored for short periods of time as fresh samples, or the samples may be processed to create freeze-dried platelet samples, which are later reconstituted and assayed.

Furthermore, the monitoring can comprise obtaining multiple samples from one donor and comparing the samples to each other and/or to a standard curve, to determine the presence and/or level of function of one or more platelet functions. For example, one can assay for Afibrinogenemia, Thromlasthenia, vWF disease, Bernard Souleir Syndrome, Receptor Defects Deisorders of Secretion/signal transduction, Storage Pool Deficiency, Diminished Thromboxane Synthesis, Signal Transduction/Primary Secretion Defects, or Deficiency of Platelet Coagulant Activities.

As with other methods of the invention, various drugs or other substances can be added to the assay mixture to determine the specific defect in the disease or disorder. Knowledge of the specific source of the defect may enable treatment regimens to be developed.

In embodiments, the method comprises obtaining freeze-dried platelets from a public source or from a patient prior to initiation of a treatment regimen, obtaining fresh platelets or plasma from a patient or a public source prior to initiation of a treatment regimen, and obtaining fresh platelets or plasma from the patient one or more times during a treatment regimen. The method further comprises determining the blood clotting ability of combinations of freeze-dried and fresh components. Typically, determining the blood clotting ability of the mixture indicates the blood clotting ability of the patient's blood, and comprises assaying clotting time of the mixture. Furthermore, typically, multiple assays are performed over time to give an indication of the effects of the treatment regimen over time.

Numerous treatments for a variety of diseases and disorders are available to the public. Some of these treatments, while effectively treating a particular disease or disorder, result in unintended effects (i.e., side-effects) that diminish or abolish one or more functions of the blood clotting system. Other treatments are specifically designed to promote or inhibit the activity of a patient's blood clotting system. In any event, it is often desirable to monitor the presence and/or concentration of drugs in the blood of a patient, and in particular monitor the effect of those drugs on the patient's blood clotting activity. The present methods permit one to monitor such effects simply and rapidly.

It is to be noted that all of the methods of monitoring and diagnosing can comprise one or more control reactions. The concept of control reactions is well known to those of skill in the art, and numerous types of control reactions can be included in the methods of the present invention to monitor the effectiveness and success of one or more steps in the methods. Among the more common control reactions that can be performed are reactions that involve freeze-dried platelets as the sole source of platelets, reactions that involve fresh platelets as the sole source of platelets, reactions in which one or more known substances (with known effects on platelet function or clotting system function) are exposed to fresh platelets (e.g., a positive control), and reactions in which no substance in addition to platelets is added (e.g., a negative control). Included among the control reactions are reactions that generate a standard curve. Because the methods of the present invention provide repeatable aggregation characteristics when performed with accurately measured amounts of normal freeze-dried platelets and normal serum or blood, standard curves can be generated, and these standard curves can be used as a basis for comparison of test samples for any number of characteristics, including, but not limited to, platelet number/concentration, ability of the platelets to participate in clotting, and presence or absence of functional surface proteins on platelets.

It is also to be noted that, although the methods were disclosed as being suitable for use with freeze-dried platelets and fresh platelets or plasma, freeze-dried platelets can be combined according to the methods of the invention with whole blood, platelets, plasma, purified coagulation proteins, and other components of the blood system. Use of the terms "fresh platelets" and/or "fresh plasma" is to be understood to encompass all other types of fresh blood products. Furthermore, the term "fresh" does not necessarily require a strict time-dependency. Rather, it is used solely to differentiate between freeze-dried platelets and non-freeze-dried substances.

The methods of the invention may also comprise performing the method more than one time on the same sample, under the same conditions. As is known in the art, performing a method on multiple identical samples provides an indication of the reliability and reproducibility of the method. According to the present invention, each step in a method, or only certain steps within the method, can be repeated according to this embodiment of the invention.

As is evident from the above description, all the methods of detection and monitoring can encompass the general concept of determining platelet counts or function levels by assaying clot time. Thus, the methods of the invention can be considered, in embodiments, as methods of determining platelet counts of a sample comprising platelets. Likewise, the methods of the invention can be considered, in embodiments, as methods of determining platelet function of a sample comprising platelets. Typically, platelet function is assayed by the ability to participate in the clotting process.

The freeze-dried platelets of the invention can show many characteristics of fresh platelets. Among those characteristics is size—the freeze-dried platelets of embodiments of the invention are of about the same size as fresh platelets. Thus, the freeze-dried platelets can be used to calibrate instruments for detection and study of platelets. Being freeze-dried, the platelets of the invention are advantageously used for calibrating machinery because calibration can be accomplished at any convenient time, rather than in a small window of opportunity provided by fresh platelets.

The present invention recognizes, for the first time, the usefulness of freeze-dried platelets in detecting and monitoring diseases and disorders affecting the blood clotting system. It also recognizes, for the first time, the usefulness of freeze-dried platelets in monitoring the effects of drugs and drug treatment regimens on the blood clotting system of individuals to whom the drugs are administered. In essence, it recognizes that freeze-dried platelets are suitable for all diagnostic capabilities provided by fresh platelets, including monitoring any and all functions of platelets. It thus recognizes the usefulness of freeze-dried platelets in monitoring the blood clotting ability of an individual's blood. The discovery that freeze-dried platelets can be used as a substitute for fresh platelets in various assays enables methods of monitoring the blood clotting ability of blood samples, and provides information that can be important or critical to the health and life of individuals.

EXAMPLES

The invention will be further explained by the following Examples, which are intended to be purely exemplary of the invention, and should not be considered as limiting the invention in any way.

Unless otherwise noted, the following experiments utilized platelets that: were purchased from BRT Labs (Baltimore, Md.) and used either within 4-24 hours of draw or at 6-7 days post draw; were fresh platelets that were collected into acid citrate dextrose (ACD) anticoagulant buffer (1.5 volumes platelets+8.5 volumes blood); or were outdated platelets (George Washington University Blood Banks, Washington D.C.) no longer than 5 days outdated.

Example 1

Preparation of Freeze-Dried Platelets

A method of preparing freeze-dried platelets was developed to provide platelets having a long shelf-life and suitable characteristics upon rehydration. The method was found to provide freeze-dried platelets, and platelets reconstituted from those freeze-dried platelets, with advantageous properties for in vitro studies and in vivo therapeutic applications.

The method of preparing freeze-dried platelets comprised the following:

An initial saccharide-loading process included:

all solutions, buffers, equipment, etc. were checked to ensure that each was at or near room temperature to minimize adverse effects of cold temperatures on the platelets;

platelet-rich plasma (PRP) was obtained;

the suitability of the platelets was checked by checking swirling—if no swirling was noticed, the platelets were rejected;

the pH of the platelet composition was checked and samples having a pH lower than 6.2 were rejected;

where applicable, different samples of platelets (e.g., PRP) were pooled in a plastic beaker;

the platelet composition was stirred and the pH measured—if necessary, the pH was adjusted to 6.6-6.8 with ACD buffer (85 mM Sodium Citrate; 65 mM Citric Acid; 111 mM glucose; in deionized ultrafiltered water; filtered);

the platelet count was determined on an ACT-10 instrument, and dilutions were made to get the platelets within the linear range of the ACT-10 (about 10 to 1000);

platelets were divided equally into different centrifuge bottles;

where necessary, red blood cells (RBC) were removed by centrifugation in a fixed angle centrifuge at 500×g for 5 minutes—platelet rich plasma fraction was then removed to a new clean bottle and a new platelet count taken;

where desired, a sample of the PRP was taken for later analysis (5-10 ml);

platelets were pelleted by centrifugation at 1500×g for 15 minutes;

platelet poor plasma was removed by aspiration and saved for later use, if desired;

the pelleted platelets were resuspended in a minimal volume (equal to about 5% of the volume of the platelet poor plasma removed in the previous step) of Loading Buffer (9.5 mM HEPES; 100 mM NaCl; 4.8 mM KCl; 5.0 mM glucose; 12 mM $NaHCO_3$; 50 mM trehalose; pH 6.8);

the resuspended platelets were measured for platelet counts, and the concentration adjusted to approximately 1250 ($1.25 \times 10^9$/ml, as measured by the ACT-10 machine);

the volume was recorded;

the platelets were incubated at 37° C. in a waterbath for two hours;

during the incubation period, a clot retraction assay was performed to compare the PRP with platelet-poor plasma—if platelets failed to contract the clot as compared to the platelet-poor plasma, the platelet preparation was rejected;

after incubation, human serum albumin was added to a final concentration of 5% (w/v);

the final platelet concentration was measured on the ACT-10 machine; and the platelet composition was lyophilized as follows:

TABLE 3

Lyophilization Protocol

| Period | Time (h) | Shelf Temp (° C.) Start | Shelf Temp (° C.) End | Vacuum (mTorr) |
| --- | --- | --- | --- | --- |
| 1 | 0.63 | 30 | −45 | ambient |
| 2 | 4 | −45 | −45 | ambient |
| 3 | 1 | −45 | −40 | 100 |
| 4 | 12 | −40 | −30 | 100 |
| 5 | 12 | 30 | 30 | 100 |

Example 2

Preparation of Freeze-Dried Platelets

A second method of preparing freeze-dried platelets was developed to provide platelets having a long shelf-life and suitable characteristics upon rehydration. The method was found to provide freeze-dried platelets, and platelets reconstituted from those freeze-dried platelets, with highly advantageous properties for in vitro studies and in vivo therapeutic applications.

The method of preparing freeze-dried platelets comprised the following:

An initial saccharide-loading process included:

all solutions, buffers, equipment, etc. were checked to ensure that each was at or more room temperature to minimize adverse effects of cold temperatures on the platelets;

platelet-rich plasma (PRP) was obtained;

the suitability of the platelets was checked by checking swirling—if no swirling was noticed, the platelets were rejected;

the pH of the platelet composition was checked and samples having a pH lower than 6.2 were rejected;

where applicable, different samples of platelets (e.g., PRP) were pooled in a plastic beaker;

the platelet composition was stirred and the pH measured—if necessary, the pH was adjusted to 6.6-6.8 with ACD buffer (85 mM Sodium Citrate; 65 mM Citric Acid; 111 mM glucose; in deionized ultrafiltered water; filtered);

the platelet count was determined on an ACT-10 instrument, and dilutions were made to get the platelets within the linear range of the ACT-10 (about 10 to 1000);

where necessary, red blood cells (RBC) were removed by centrifugation in a fixed angle centrifuge at 500×g for 5 minutes-platelet rich plasma fraction was then removed to a new clean bottle and a new platelet count taken;

where desired, a sample of the PRP was taken for later analysis (5-10 ml);

platelets were pelleted by centrifugation at 1500×g for 15 minutes;

platelet poor plasma was removed by aspiration and saved for later use, if desired;

the pelleted platelets were resuspended in a minimal volume (equal to about 10% of the volume of the platelet poor plasma removed in the previous step) of Loading Buffer (9.5 mM HEPES; 100 mM NaCl; 4.8 mM KCl; 5.0 mM glucose; 12 mM $NaHCO_3$; 50 mM trehalose; pH 6.8);

the resuspended platelets were measured for platelet counts, and the concentration adjusted to approximately 1250 ($1.25 \times 10^9$/ml, as measured by the ACT-10 machine);

the volume was recorded;

the platelets were incubated at 37° C. in a waterbath for two hours;

during the incubation period, a clot retraction assay was performed to compare the PRP with platelet-poor plasma—if platelets failed to contract the clot as compared to the platelet-poor plasma, the platelet preparation was rejected;

after incubation, Ficoll 400 was added to the platelets to give a final concentration of 6% (w/v);

the final platelet count was measured on an ACT-10 machine (the count typically was approximately 1000 ($1 \times 10^9$/ml);

the platelets were aliquotted and lyophilized using the same lyophilization protocol described in Table 3;

After lyophilization, the vials in which the platelets were lyophilized were stoppered under vacuum, capped immediately, and baked in an oven at various temperatures and times.

Where desired, the platelets were rehydrated with the same volume as the pre-lyophilization volume of the rehydration buffer added to the dried platelets. For example, if 1 ml of composition was lyophilized, then 1 ml of reconstitution buffer was added for rehydration.

The rehydration process usually involved the addition of distilled water; 6% Ficoll-400 in distilled water; 6% Ficoll-400, 2 mM Calcium Chloride in distilled water; or 6% Ficoll-400, 2 mM Calcium Chloride, 1 mM Magnesium Chloride in distilled water.

The rehydrated platelets were allowed to equilibrate at room temperature for 30 seconds to 300 seconds before use.

Example 3

Preparation of a Composition of the Invention

Non-autologous platelets were purchased from BRT Labs (Baltimore, Md.) and used within 4-24 hours of draw. Platelet Rich Plasma (PRP) was obtained by low speed centrifugation (135×g) for 15 minutes to remove red blood cells. The centrifuged PRP (without red blood cells) was acidified to pH 6.5 by adding $\frac{1}{14}$ volumes of ACD (acid citrate dextrose) and then pelleted by centrifuge at 1000×g for 10 minutes. The platelet-poor plasma was decanted, and the packed cells were drained over a paper towel to remove plasma proteins. Alternatively, residual liquid was removed by aspiration with a plastic transfer pipette. The platelets were resuspended in 1 ml of Cation-Free Tyrodes Buffer containing 50 mM of trehalose at pH 6.8, and the platelet concentration was adjusted to ~$1.0 \times 10^9$/ml. The mixture was incubated for 2 hours at 37° C., mixing once each half hour. Finally, the albumin (BSA) concentration was adjusted to 5% (w/v) of the platelet preparation for lyophilization. The lyophilization was performed according to Table 3.

The resulting lyophilized composition was irradiated at 0, 5, 30, and 50 kGy, packed, and sealed for various applications.

Example 4

Alternative Method for Making Freeze-Dried Platelets

A method of preparing freeze-dried platelets was developed to provide platelets having a long shelf-life and suitable characteristics upon rehydration. The method was found to provide freeze-dried platelets, and platelets reconstituted from those freeze-dried platelets, with advantageous properties for in vitro studies and in vivo therapeutic applications.

The method of preparing freeze-dried platelets comprised the following:

An initial saccharide-loading process included:

all solutions, buffers, equipment, etc. were checked to ensure that each was at or near room temperature to minimize adverse effects of cold temperatures on the platelets;

platelet-rich plasma (PRP) was obtained;

the suitability of the platelets was checked by checking swirling—if no swirling was noticed, the platelets were rejected;

the pH of the platelet composition was checked and samples having a pH lower than 6.2 were rejected;

where applicable, different samples of platelets (e.g., PRP) were pooled in a plastic beaker;

the platelet composition was stirred and the pH measured—if necessary, the pH was adjusted to 6.6-6.8 with ACD buffer (85 mM Sodium Citrate; 65 mM Citric Acid; 111 mM glucose; in deionized ultrafiltered water; filtered);

the platelet count was determined on an ACT-10 instrument, and dilutions were made to get the platelets within the linear range of the ACT-10 (about 10 to 1000);

platelets were divided equally into different centrifuge bottles;

where necessary, red blood cells (RBC) were removed by centrifugation in a fixed angle centrifuge at 500×g for 5 minutes-platelet rich plasma fraction was then removed to a new clean bottle and a new platelet count taken;

where desired, a sample of the PRP was taken for later analysis (5-10 ml);

platelets were pelleted by centrifugation at 1500×g for 15 minutes;

platelet poor plasma was removed by aspiration and saved for later use, if desired;

the pelleted platelets were resuspended in a minimal volume (equal to about 5% of the volume of the platelet poor plasma removed in the previous step) of Loading Buffer (9.5 mM HEPES; 100 mM NaCl; 4.8 mM KCl; 5.0 mM glucose; 12 mM NaHCO$_3$; 50 mM trehalose; pH 6.8);

the resuspended platelets were measured for platelet counts, and the concentration adjusted to approximately 1250 ($1.25\times10^9$/ml, as measured by the ACT-10 machine);

the volume was recorded;

the platelets were incubated at 37° C. in a waterbath for two hours;

during the incubation period, a clot retraction assay was performed to compare the PRP with platelet-poor plasma—if platelets failed to contract the clot as compared to the platelet-poor plasma, the platelet preparation was rejected;

after incubation, human serum albumin was added to a final concentration of 5% (w/v);

the final platelet concentration was measured on the ACT-10 machine; and the platelet composition was lyophilized as indicated in Table 3, above;

Example 5

Alternative Method for Making Freeze-Dried Platelets With An Increased Percent of Microparticles A method of preparing freeze-dried platelets was developed to provide platelets having a long shelf-life and suitable characteristics upon rehydration. The method was found to provide freeze-dried platelets, and platelets reconstituted from those freeze-dried platelets, with advantageous properties for in vitro studies and in vivo therapeutic applications and having a high percentage of microparticles.

The method of preparing freeze-dried platelets comprised the following:

An initial saccharide-loading process included:

all solutions, buffers, equipment, etc. were checked to ensure that each was at or near room temperature to minimize adverse effects of cold temperatures on the platelets;

platelet-rich plasma (PRP) was obtained;

the suitability of the platelets was checked by checking swirling—if no swirling was noticed, the platelets were rejected;

the pH of the platelet composition was checked and samples having a pH lower than 6.2 were rejected;

where applicable, different samples of platelets (e.g., PRP) were pooled in a plastic beaker;

the platelet composition was stirred and the pH measured—if necessary, the pH was adjusted to 6.6-6.8 with ACD buffer (85 mM Sodium Citrate; 65 mM Citric Acid; 111 mM glucose; in deionized ultrafiltered water; filtered);

the platelet count was determined on an ACT-10 instrument, and dilutions were made to get the platelets within the linear range of the ACT-10 (about 10 to 1000);

platelets were divided equally into different centrifuge bottles;

where necessary, red blood cells (RBC) were removed by centrifugation in a fixed angle centrifuge at 500×g for 5 minutes-platelet rich plasma fraction was then removed to a new clean bottle and a new platelet count taken;

where desired, a sample of the PRP was taken for later analysis (5-10 ml);

platelets were pelleted by centrifugation at 1500×g for 15 minutes;

platelet poor plasma was removed by aspiration and saved for later use, if desired;

the pelleted platelets were resuspended in a minimal volume (equal to about 5% of the volume of the platelet poor plasma removed in the previous step) of Loading Buffer (9.5 mM HEPES; 100 mM NaCl; 4.8 mM KCl; 5.0 mM glucose; 12 mM NaHCO$_3$; 50 mM trehalose; pH 6.8);

the resuspended platelets were measured for platelet counts, and the concentration adjusted to approximately 1250 ($1.25\times10^9$/ml, as measured by the ACT-10 machine);

the volume was recorded;

the platelets were incubated at 37° C. in a waterbath for two hours;

during the incubation period, a clot retraction assay was performed to compare the PRP with platelet-poor plasma—if platelets failed to contract the clot as compared to the platelet-poor plasma, the platelet preparation was rejected;

after incubation, human serum albumin was added to a final concentration of 5% (w/v);

the final platelet concentration was measured on the ACT-10 machine;

the platelet concentration was subjected to a quick freeze by immersing into liquid nitrogen (−190° C.) for 60 seconds; and the platelet composition was lyophilized as indicated in Table 3, above.

Example 6

Comparative Example of Method Used in the Art To Produce Freeze-Dried Platelets

To produce freeze-dried platelets for comparison to those made according to embodiments of the present invention, a protocol known in the art was used to make freeze-dried platelets. The method included:

PRP were obtained by centrifugation of blood (in CPD or CPDA anticoagulant solution) at 320×g for 14 minutes using a swinging bucket rotor and no centrifugation breaking;

PRP were removed and transferred to fresh tubes, taking care to avoid contamination with RBC;

PGE$_1$ in ethanol was added to 10 ug/ml from a 100× stock, and platelets were counted;

platelets were centrifuged at 480×g for 25 minutes;

the platelet-poor supernatant was removed by aspiration;

platelets were resuspended in $1\times10^9$/ml in Tyrodes Phosphate Buffer, pH 6.8 containing 5 mM glucose and 40 mM trehalose, with 2 mM Mg$^{2+}$ plus 10 ug/mL PGE1 (added at 1:100 from 1 mg/ml stock) (i.e., 4.63 mM Na$_2$HPO$_4$, 5.37 mM NaH$_2$ PO$_4$, 120 mM NaCl, 2.67 mM KCl, 2 mM NaHCO$_3$, 5 mM glucose, 2 mM MgCl$_2$, 40 mM trehalose, pH 6.8 (+10 ug/ml PGE1 from 1 mg/ml stock in EtOH);

a small amount was saved for further assay, if desired;

the sample was incubated 4 hours at 37° C., mixing by gentle inversion every half hour;

a sample was removed, where desired, for functional testing (e.g., aggregometry and FACS);

the composition was centrifuged at 480×g for 15 minutes;

the supernatant was removed by aspiration;

the pellet was resuspended to $1-2\times10^9$/ml in isotonic HEPES saline containing 5% Human Serum Albumin, 100 mM Trehalose, and 1 mM MgCl$_2$, pH 6.8 (i.e., 9.5 mM HEPES, 75 mM NaCl, 4.8 mM KCl, 1.00 mM MgCl$_2$, 100 mM trehalose, 5% Human Serum Albumin, pH 6.8);

platelets were counted on an ACT-10 machine, and the platelet count and volume recorded;

where desired, a sample was removed and saved for later testing (e.g., functional testing);

platelets were transferred to lyophilization vials with stopper caps and the contents of each vial weighed;

platelets were lyophilized using the same lyophilize cycle from Example 1;

lyophilized platelets were sealed in the lyophilization vials under vacuum;

lyophilized platelets were stored at ambient temperature or at 2-8° C. in the absence of dessicant; and where desired, the freeze-dried platelets were rehydrated with sterile water as follows: volume of water to add=weight of vial prior to lyophilization minus the weight of the vial after lyophilization, assuming 1 ml of water=1.0 g.

To determine the characteristics of freeze-dried platelets made according to an embodiment of the present invention, freeze-dried platelets made according to Example 2 above were rehydrated in distilled water and tested for various physical and functional properties.

A graphical flow-chart comparison of the protocols presented in Examples 1 and 2, along with an optional HLA reduction step (detailed below) and the comparative protocol of Example 6 is presented in FIG. 1.

Example 7

Characterization of Freeze-Dried Platelets Prepared According to Example 2

To determine the characteristics of freeze-dried platelets made according to an embodiment of the present invention, freeze-dried platelets made according to Example 2 above were rehydrated as described above and tested for various physical and functional properties.

In one set of experiments, the reconstituted platelets' ability to promote plasma clot times in a dose-dependent manner was assayed. For these experiments, 100 ul of APCT (activated plasma clot time, Analytical Control Systems, Inc., Fishers, Ind.) reagent was mixed with 25 ul of various concentrations of water-reconstituted freeze-dried platelets and 25 ul of plasma obtained from commercial suppliers. The mixture was incubated at 37° C. in a water bath for 3 minutes, then 100 ul of 0.02 M $CaCl_2$ (37° C.) was added, and clot time determined.

Figure 2:
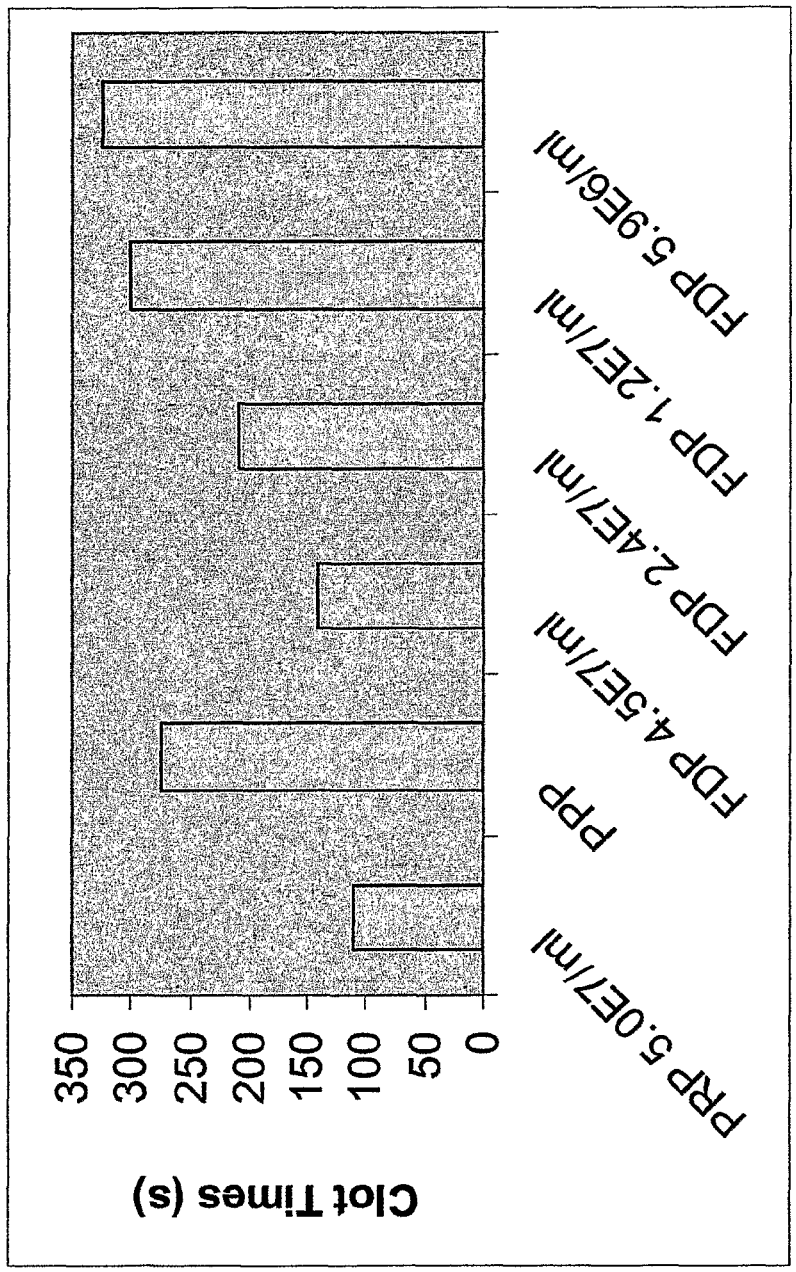
FIG. 2 is a graph showing the effectiveness of freeze-dried platelets of an embodiment of the invention to promote plasma clotting in a dose-dependent manner.

As can be seen from FIG. 2, the reconstituted freeze-dried platelets made according to Example 2 promote plasma clotting dimes in a dose-dependent manner, in a similar fashion as fresh platelets. More specifically, FIG. 2 shows the clotting times for various preparations, including platelet-rich plasma (PRP; lane 1), platelet-poor plasma (PPP), and freeze-dried platelets (FDP) of the invention at various concentrations. It can be seen that the FDP show at least as good of clotting ability as PRP, but a drop in clotting effectiveness as the number of platelets is reduced.

In another set of experiments, the ability of reconstituted FDP made by the protocol of Example 2 to promote clot retraction was tested. Briefly, the procedure involved: addition of about $4.5 \times 10^7$ reconstituted platelets per ml to 1 ml of platelet-poor plasma. To this, 0.02 M $CaCl_2$ was added and incubated at 37° C. Initial formation of clots was measured and at 30 minutes, the length of the clot was measured again. The amount of clot retraction was calculated based on the length of clot at time zero and at time 30 minutes.

Figure 3:
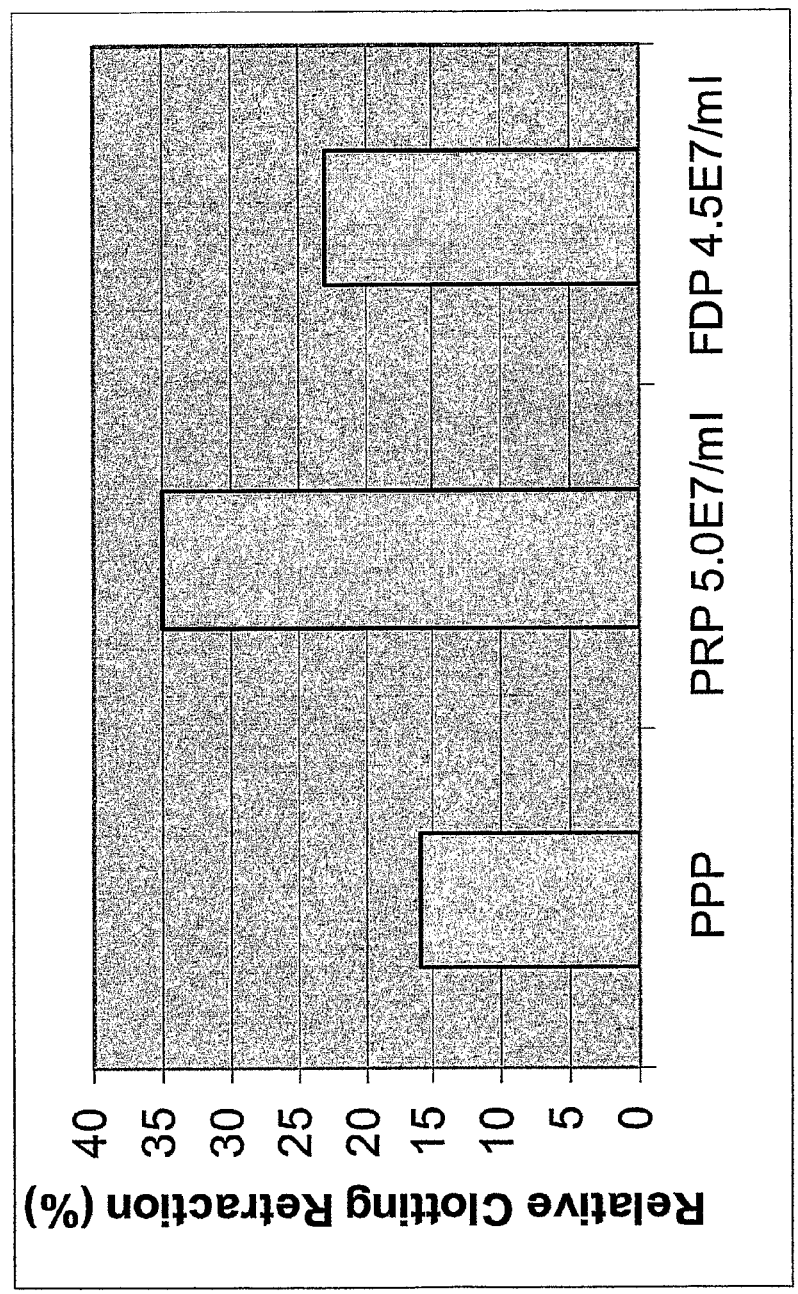
FIG. 3 is a graph showing the effectiveness of freeze-dried platelets of an embodiment of the invention in promoting clot retraction.

As can be seen from FIG. 3, reconstituted freeze-dried platelets of the invention can promote clot retraction in the same manner as fresh platelets. More specifically, the relative clot retraction amount is higher in reconstituted FDP than in PPP, and somewhat lower than a similar amount of PRP.

Example 8

Effect of Post-Lyophilization Heat Step on Size and Granularity of Freeze-Dried Platelets To determine the effect of the post-lyophilization treatment step of the protocol described in Example 2, the size and granularity of reconstituted platelets made by that protocol were examined and compared to the size and granularity of fresh platelets treated in the same manner. Experiments were performed on a Becton Dickenson FACS caliber instrument using log-log settings. Platelets were characterized by their representative forward and side scatter light profiles (performed using gel filtered platelets) and by the binding of the FITC anti-human CD 41. Platelets were diluted to ~50,000 per ul in HBMT in separate tubes and Fluorescence-labeled antibodies were added at saturation for 30 minutes at ambient temperature. Samples were diluted with 2 ml HMBT and 10,000 individual events collected. The fluorescence histogram and percentage of positive cells were recorded, and this represented the platelet population that bound to the fluorescence labeled antibody. The results are presented in FIGS. 4-6.

Figure 4:
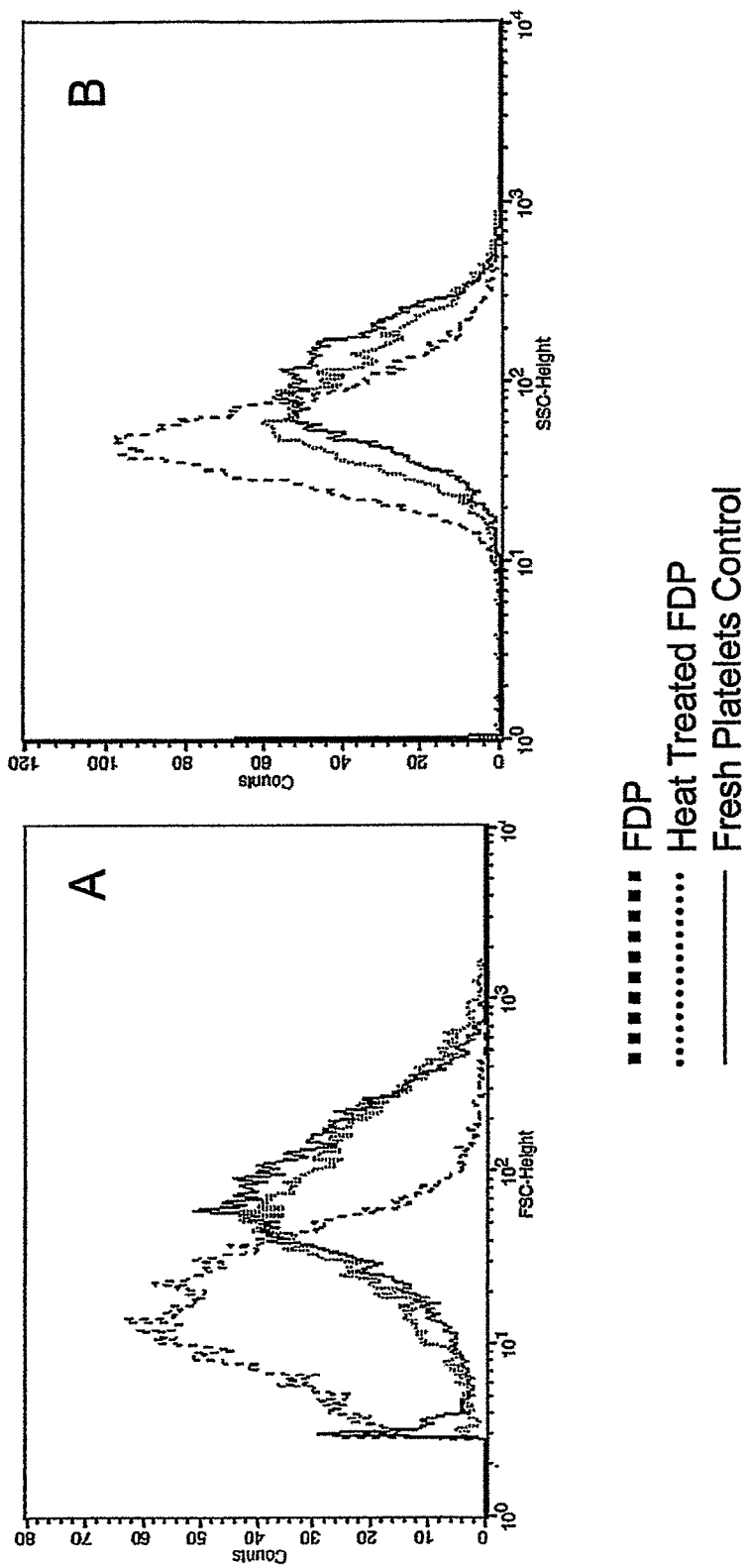
FIG. 4 shows fluorescence activated cell sorting (FACS) analyses representing the results of assays of the size and granularity of reconstituted heat-treated freeze-dried platelets made according to an embodiment of the invention. Panel A, shows the size of reconstituted freeze-dried platelets and fresh platelets after various heat treatments. Panel B, shows the granularity of reconstituted freeze-dried platelets and fresh platelets after various heat treatments.
Figure 5:
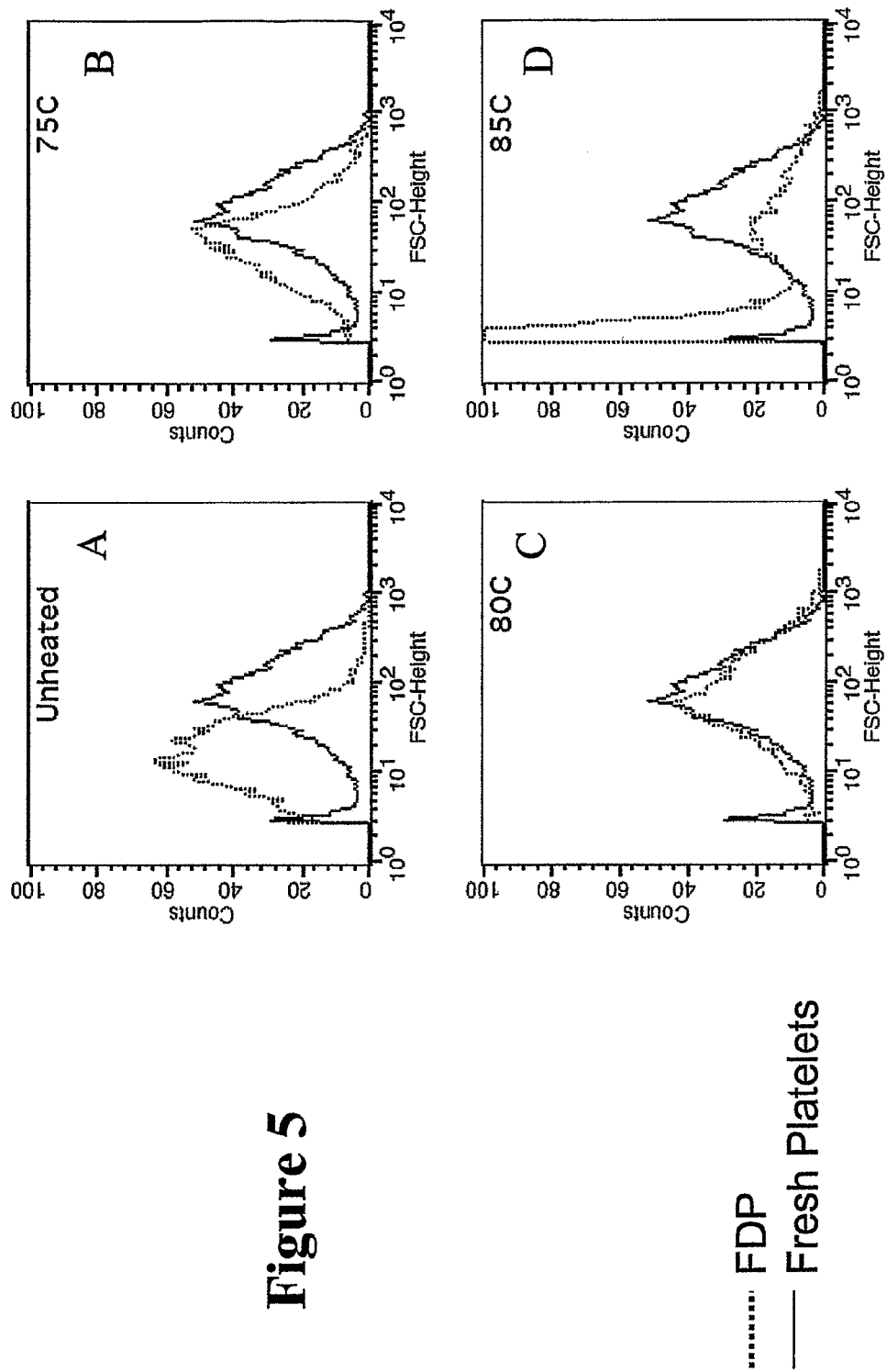
FIG. 5 shows FACS analyses showing the effect on platelet size of a post-lyophilization heat treatment step for 24 hours at various temperatures ranging from 75° C. (Panel B) to 80° C. (Panel C) to 85° C. (Panel D), with an unheated sample (Panel A) as control.

FIG. 4 shows graphs representing the results of experiments to assay the size and granularity of reconstituted freeze-dried platelets made according to Example 2, made with and without the post-lyophilization heat treatment step. Size distribution (FIG. 4A) and granularity (FIG. 4B) of heat treat reconstituted FDP (heated at 80° C. for 24 hours) are virtually identical to fresh platelets whereas the non-heat treated reconstituted FDP are smaller in size and de-granulated FIG. 5 shows the effect of a post-lyophilization heat treatment step on platelet size at various temperatures ranging from 75° C. to 80° C. to 85° C., with an unheated sample as control. More specifically, freeze-dried platelets made according to the procedure described in Example 2 were produced identically to each other, up to the point of heat treatment. At the heat treatment step, samples were heated at 75° C., 80° C., or 85° C. for 24 hours, or maintained at room temperature for 24 hours. Fresh platelets in plasma were prepared right before the comparative analysis. The samples from each time point for each temperature were combined, and the size of the platelets assayed using FACS analysis. The results, which are shown in FIG. 5, show that heating of freeze-dried platelets at temperatures up to 80° C. for 18-24 hours improves the size of the platelets (i.e., promotes size retention, as compared to fresh platelets), but that the beneficial effects drop off at 85° C. or higher. Similar results were obtained for treatment for 18 hours (data not shown).

Figure 6:
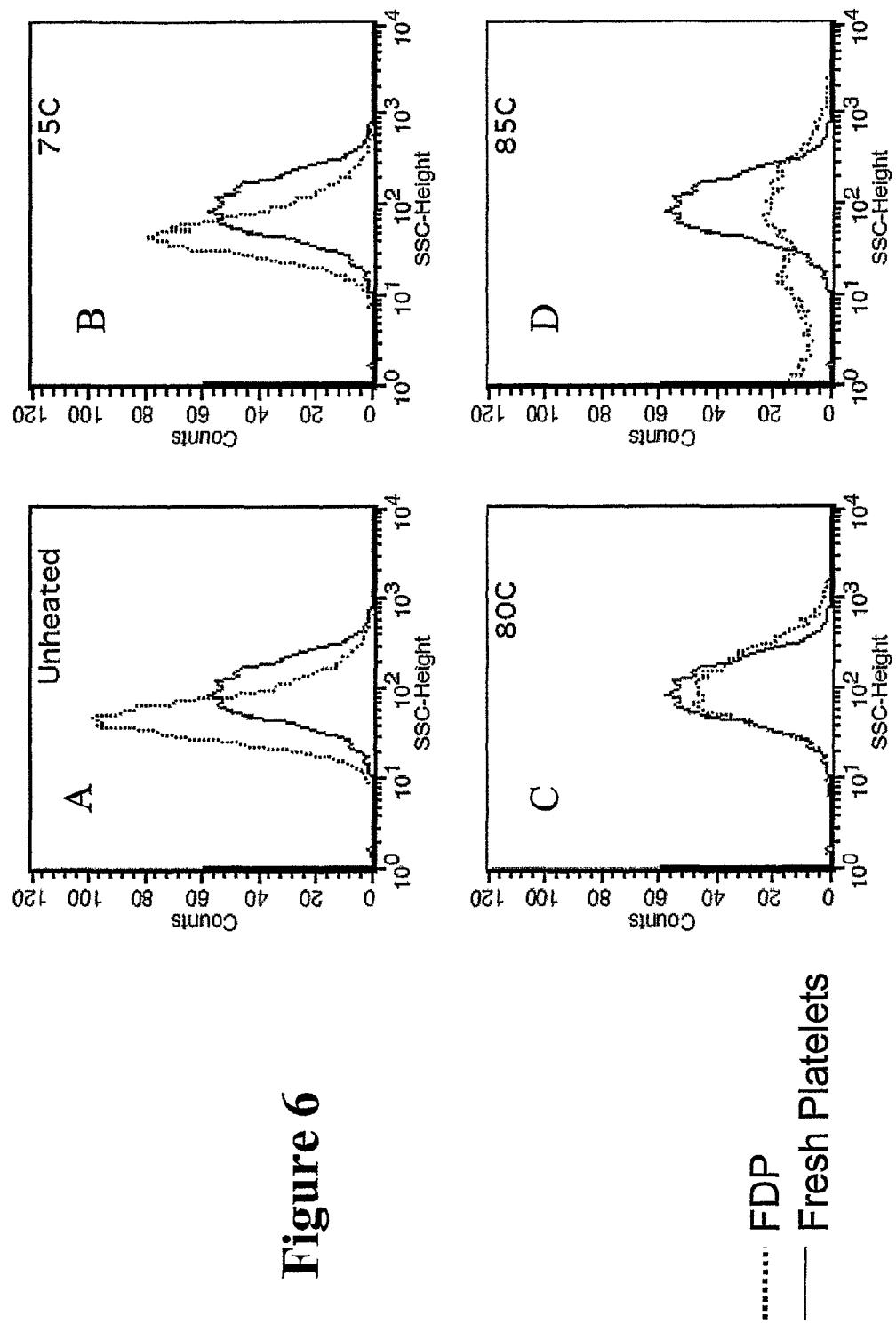
FIG. 6 shows FACS analyses showing the effect on platelet granulation of a post-lyophilization heat treatment step for 24 hours at various temperatures ranging from 75° C. (Panel B) to 80° C. (Panel C) to 85° C. (Panel D), with an unheated sample (Panel A) as control.

FIG. 6 is a graph showing the effect on platelet granulation of a post-lyophilization heat treatment step for 24 hours at various temperatures ranging from 75° C. to 80° C. to 85° C., with an unheated sample as control. More specifically, freeze-dried platelets made according to the procedure described in Example 2 were produced identically to each other, up to the point of heat treatment. At the heat treatment step, samples were heated at 75° C., 80° C., or 85° C. for 24 hours, or maintained at room temperature for 24 hours. Fresh platelets in plasma were prepared before the analysis. The samples from each time point for each temperature were combined, and the granularity of the platelet preparations was assayed using FACS analysis. The results, which are shown in FIG. 6, show that heating of freeze-dried platelets at temperatures up to 80° C., and particularly at about 80° C., for 24 hours improves the granularity of the platelets (i.e., mimics the granularity of fresh platelets), but that the beneficial effects drop off at 85° C. or higher. Similar results were obtained for incubations for 18 hours (data not shown).

Example 9

Effect of Post-Lyophilization Heat Treatment on Size of Freeze-Dried Platelets as Compared to Other Methods To determine the suitability of the freeze-dried platelets of the invention, and particularly those produced using the heat-treatment step disclosed in Example 2, three samples were assayed for size. The first sample comprised fresh platelets in plasma. The second sample comprised reconstituted platelets prepared according to the comparative method of Example 6, where the freeze-dried platelets were reconstituted with distilled water. The third sample comprised reconstituted freeze-dried platelets made according to Example 2, using a post-lyophilization heat treatment of 24 hours at 80° C. and were reconstituted with distilled water. Each sample was subjected to FACS analysis as described above, and the results are presented in FIG. 7.

Figure 7:
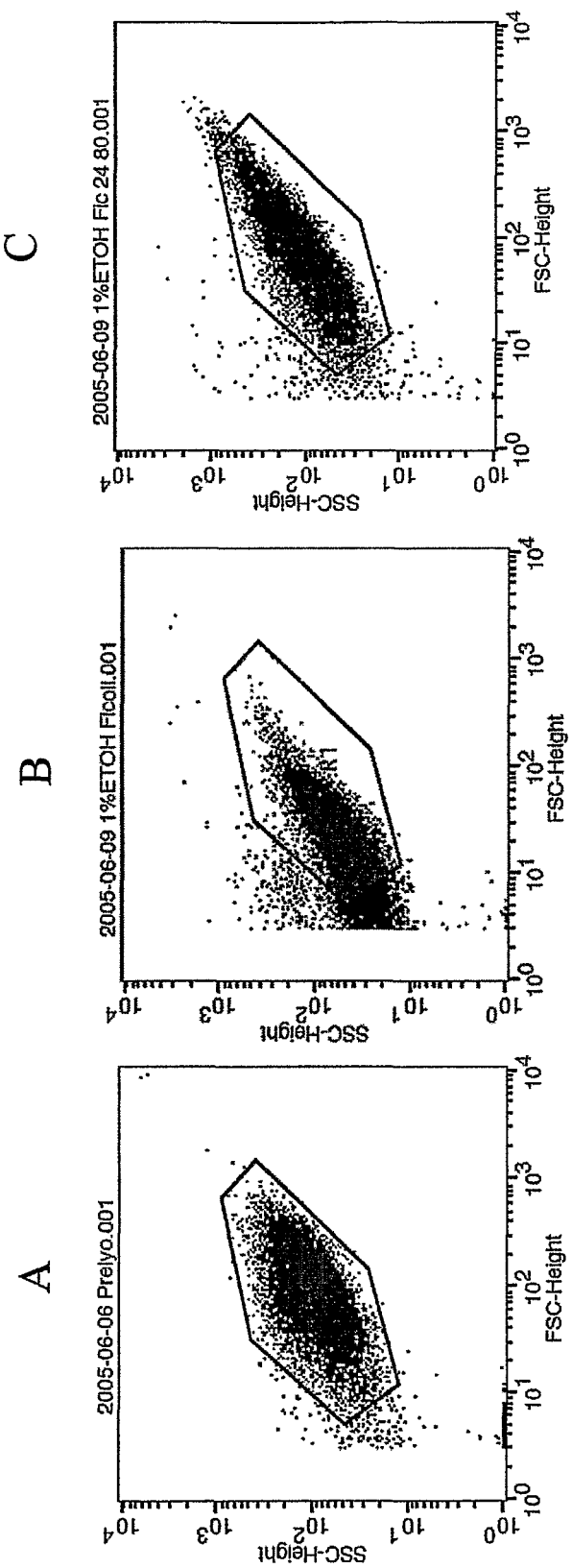
FIG. 7 depicts FACS analyses of fresh platelets (Panel A), freeze-dried platelets made according to a leading protocol known in the art (Panel B), and a protocol of the present invention (Panel C).

The results in FIG. 7 depict the average size and granularity of each sample. The sample containing fresh platelets was analyzed (FIG. 7A), and a gate or window placed on the FACS graph to indicate the area where essentially all of the platelets were positioned. The sample containing reconstituted freeze-dried platelets made according to the comparative example of Example 6 was similarly analyzed, and a gate or window placed on the FACS graph at the same position as in FIG. 7A. Finally, the sample containing reconstituted freeze-dried platelets made according to the protocol disclosed in Example 2 was similarly analyzed, and a gate or window placed on the FACS graph at the same position as in FIG. 7A. As can be seen from a comparison of FIGS. 7A, 7B, and 7C, the sample comprising reconstituted freeze-dried platelets according to the present invention showed an almost identical size and granularity distribution, as compared to fresh platelets, whereas the reconstituted platelets made by the comparative example were significantly shifted outside the area where fresh platelets were located. This example shows that reconstituted freeze-dried platelets made according to a method of the present invention are more similar to fresh platelets than reconstituted freeze-dried platelets made by a protocol known in the art.

Example 10

Characterization of Biological Activities of Freeze-Dried Platelets Prepared According to Example 2

To demonstrate the reconstituted freeze-dried platelets can aggregate in response to the addition of agonists, various agonists (Arachidonic Acid at 0.5 mg/ml, Collagen at 10 ug/ml, Epinephrine at 300 uM, Thrombin Receptor Activating Peptide (TRAP: SFLLRN) at 10 mM, and Ristocetin at 1 mg/ml plus 20% Citrated Plasma and saline were added to 400 ul of reconstituted freeze-dried platelets at 250,000 platelets per ul in HEPES-Tyrodes Buffer containing 0.3% bovine serum albumin (BSA) to final volume of 500 ul. Aggregation of the platelets was determined after 5 minutes at room temperature. Platelets were counted using a standard Complete Blood Count machine (ACT 10 from Beckman coulter). The results showed that freeze-dried platelets aggregated in response to Arachidonic Acid, Collagen, Epinephrine, thrombin receptor activing peptide (TRAP), and Ristocetin with aggregation percentages determined to be 77, 83, 86, 93, 97, and 10, respectively (see Table 1, above).

Example 11

Characterization of Platelet Surface Markers Upon Reconstitution

In another series of experiments, reconstituted freeze-dried platelets made according to Example 2, with a heat-treatment step of 80° C. for 24 hours, were assayed for common surface markers of platelets. Experiments were performed using FACS analysis as indicated above using the following fluorescence antibodies:

| | |
|---|---|
| Isotype | BD Pharminagen Mouse IgG kappa |
| HLA | BD Pharminagen anti-human HLA-A-B-C |
| GPIb | DakoCytomation mouse anti-human CD42b clone AN51 |
| IIbIIIa | DakoCytomation mouse anti-human CD41 clone 5b12 |
| P-selectin | BD Pharminagen anti-human CD62P (cat #555523). |

To determine the ability of freeze-dried platelets of the invention to retain surface receptors that are relevant for platelet function, FACS analyses were performed on fresh platelets prepared right before the experiment; those produced using the heat-treatment step disclosed in Example 2, and those produced according to the comparative method of Example 6. All freeze-dried platelets were reconstituted with distilled water.

As noted, for base line computation to fresh platelets, the following values are readjusted and normalized into percentages. The percent of the constitutively expressed receptors GP1b, GPIIb/IIIa and HLA were set at 100% for fresh platelets. For P-selectin, the protein does not express when platelets are resting (5-10% expression on the average) and fully expresses when platelets are active (100%).

The freeze-dried platelets produced using the heat-treatment step disclosed in Example 2 showed a percent of constitutively expressed receptors GP1b and GPIIb/IIIa ranging from 65-75% and 100%, respectively, with respect to fresh platelets. For HLA, when acid treated, the levels of HLA expression reduced to 5%, whereas they remained at 100% when not acid treated, with respect to fresh platelets. For P-selectin, the protein constitutively expressed whether or not the freeze-dried platelets were active or resting. The results are shown in tabular form in Table 2, above.

Thus, the heat treatment step indicated in Example 2 can help to preserve the expression of GPIb, an important protein for hemostasis.

Example 12

Effect of Ethanol in the Saccharide-Loading Buffer and the Lyophilization Buffer The protocol according to one embodiment of the present invention includes ethanol in the saccharide-loading buffer and the lyophilization buffer. To determine the effect of the presence of ethanol in these buffers, freeze-dried platelets were made according to the method of Example 2, heat treated at various temperatures for 24 hours, reconstituted, and assayed for size and granularity. More specifically, FACS analyses of fresh platelets (control), reconstituted freeze-dried platelets loaded with trehalose, but without ethanol in the loading buffer or lyophilization buffer, and reconstituted freeze-dried platelets loaded with trehalose in the presence of 1% ethanol and lyophilized in the presence of 0.8% ethanol, were performed. The results are presented in FIG. 8.

Figure 8:
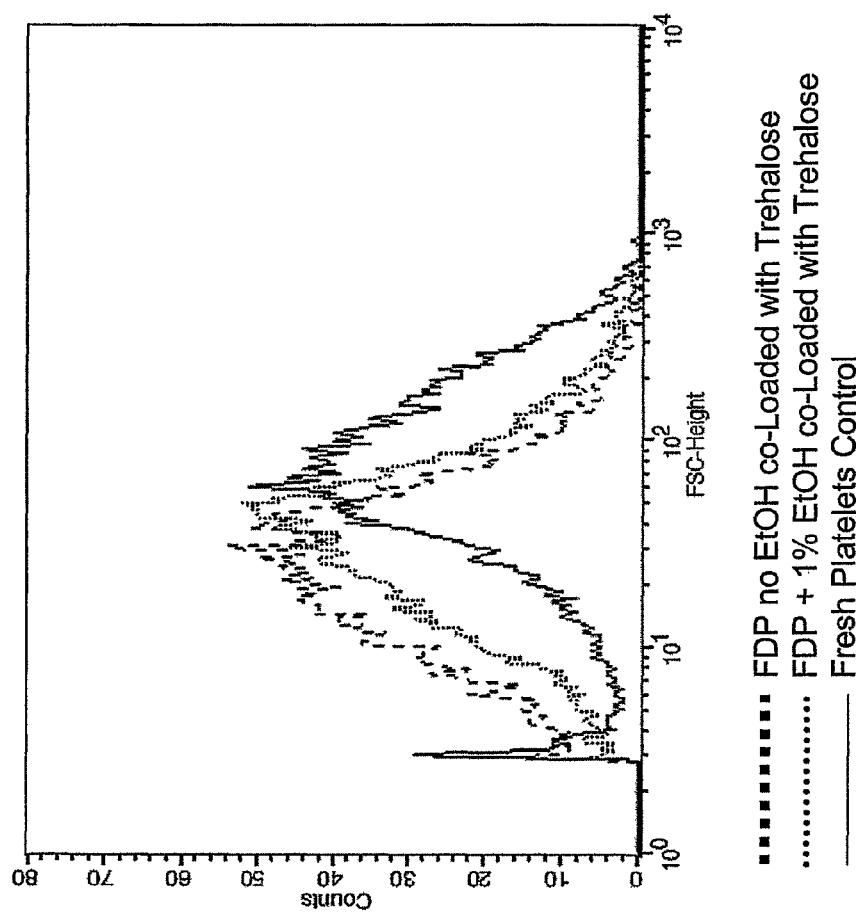
FIG. 8 depicts FACS analyses of reconstituted freeze-dried platelets and the effect of the presence of ethanol in the saccharide-loading buffer and lyophilization buffer.

As can be seen in FIG. 8, the presence of ethanol in both the loading buffer and the lyophilization buffer improved the size distribution of reconstituted freeze-dried platelets as compared to a similar protocol performed in the absence of ethanol. In contrast, it had no significant effect on the granularity of the reconstituted platelets. For the first time, the current invention provides evidence to show that the inclusion of ethanol in the loading and, in particular, lyophilization buffers helps to stabilize the platelets and promote platelet saccharide uptake in the loading step.

Example 13

HLA Reduction

One embodiment of the process of preparing freeze-dried platelets of the invention includes an optional HLA reduction step. To determine the usefulness of this optional step in conjunction with the processes described in Examples 1 and 2, the optional step was performed just after the initial pelleting of platelets in each of those Examples. The details of the HLA reduction for each Example is provided below.

The pelleted platelets from Examples 1 and 2 were resuspended in a minimal volume of Reduction Buffer (9.5 mM HEPES; 100 mM NaCl; 4.8 mM KCl; 5.0 mM glucose; 12 mM $NaHCO_3$; 100 mM EGTA pH 4.0), where the minimal volume of reduction buffer defined in this step was equal to about 10% of the volume of the platelet poor plasma removed in the previous step. After 2 hours of incubation at room temperature, the platelets were washed 3 times with wash buffer (9.5 mM HEPES; 100 mM NaCl; 4.8 mM KCl; 5.0 mM glucose; 12 mM $NaHCO_3$ pH 6.8), same volume as reduction buffer, and pelleted as before.

The option step can be build into the protocol to provide the flexibility of reducing the immunogenicity of the composition. Freeze-dried platelets made according to Example 2 above were rehydrated in distilled water and tested for the amount of HLA on the surface of the platelets. To analyze for HLA content on the surface of the freeze-dried platelets, these experiments were performed on a Becton Dickenson FACS caliber instrument using log-log settings. Platelets were characterized by their representative forward and side scatter light profiles (performed using gel filtered platelets) and by the binding of the FITC anti-human HLA-A-B-C. Platelets were diluted to ~50,000 per ul in HBMT in separate tubes and Fluorescence-labeled antibodies were added at saturation for 30 minutes at ambient temperature. Samples were diluted with 2 ml HMBT and 10,000 individual events collected. The fluorescence histogram and percentage of positive cells were recorded, and this represented the platelet population that bound to the fluorescence labeled antibody.

Figure 9:
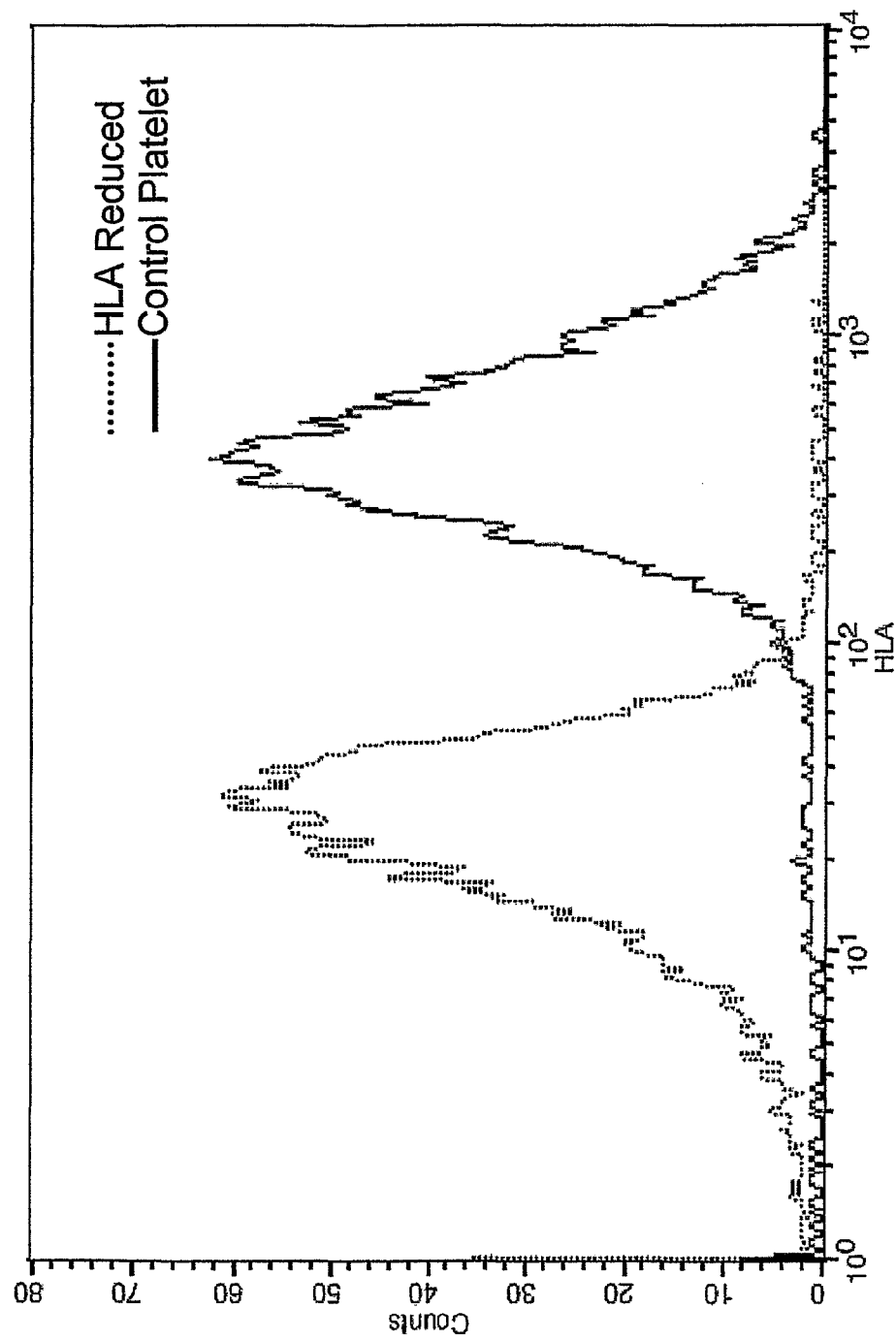
FIG. 9 depicts a FACS analysis of relative amounts of HLA marker on the surface of freeze-dried platelets when produced according to an embodiment of the invention in which acid treatment is included.

As can be seen from FIG. 9, without acid treatment, the controlled platelets expressed strong fluorescence signal, whereas, for the platelets that were treated acidic buffer as outlined in Example 2, the fluorescence signal decrease by almost 95%.

Example 14

Cell-Based Proliferation Assay

Fibroblast and endothelial cell proliferation assays were performed using a composition prepared according to Example 4. Briefly, freeze-dried platelets were made as follows: platelets were collected into acid citrate dextrose (ACD) anticoagulant buffer (1.5 volumes+8.5 volumes blood). Platelet Rich Plasma (PRP) was obtained by low speed centrifugation (135×g for 15 minutes) to remove red blood cells. The PRP was acidified to pH 6.5 by adding 1/14 volume of ACD and then pelleted by centrifugation at 1000×g for 10 minutes. The platelet pellet was resuspended in 1 ml of Cation-Free Tyrodes Buffer containing 50 mM trehalose, pH 6.8, and adjusted to ~$1.0 \times 10^9$ platelets/ml. The mixture was incubated for 2 hours at 37° C., mixing once each half hour. Finally, albumin was added to a final concentration of 5% of the total platelet preparation volume, and the platelet preparation was lyophilize.

Fibroblasts and Human Umbilical Vein Endothelial Cells (HUVECs) at passage 3 and 7, respectively, were starved for 24 hours using medium without Fetal Bovine Serum supplement. After 24 hours, the cells were passaged and seeded at 10,000 cells/well in a 96 well flat bottom dish, and allowed to attach for 2-3 hours. Once the cells were attached, the samples were added and incubated in a 37° C., 5% $CO_2$ humidified incubator for 48 hours. At 48 hours, the proliferation of the cells was measured by the MTT assay (ATCC), in which the cells reduced MTT dye that could be measured by the absorbance at 590-650 µm. Briefly, MTT dye was added to the well at a 1:10 ratio, and the plate was incubated at 37° C., 5% $CO_2$ humidified incubator for 2-3 hrs. After incubation, 100 ul of detergent was added and the optical density was determined at 590-650 nm. The numerical values obtained from A590-650 readings were used as a reference proliferation index.

Figure 10:
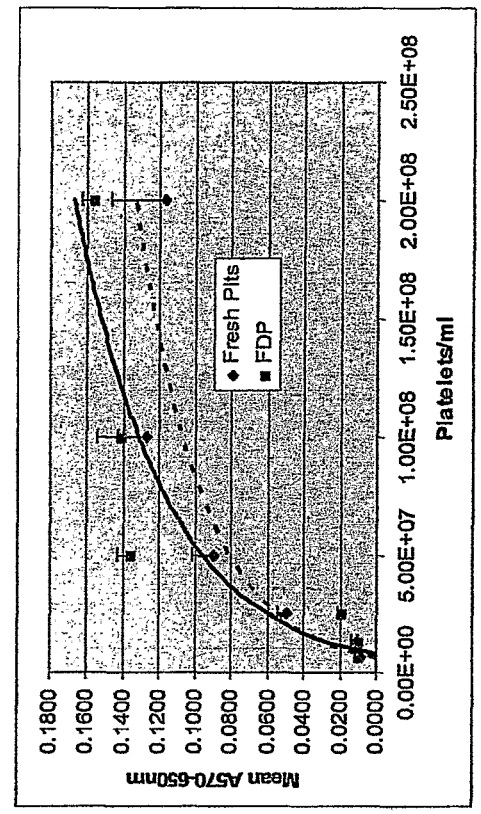
FIG. 10 depicts graphs showing the effects of freeze-dried platelets on the proliferation of fibroblasts (Panel A) and human umbilical vein endothelial cells (Panel B).
Figure 10:
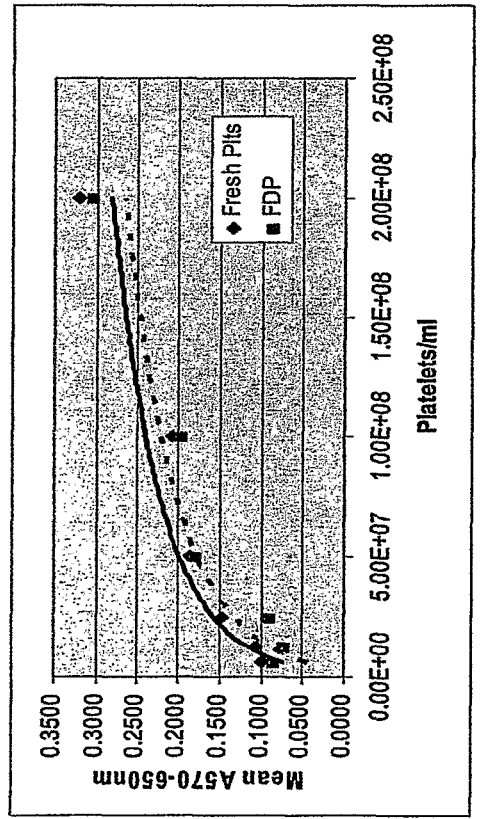

The results of the proliferation assay are presented in FIG. 10, which shows that the freeze-dried platelets of the invention had essentially the same effect on proliferation of fibroblasts and endothelial cells as fresh platelets.

Example 15

Collagen-Fibroblast Contraction Assay

To even further characterize the platelets produced in Example 3, a collagen contraction assay was performed using those platelets. For the collagen contraction assay, fibroblast cultures at 80% confluence were harvested by treatment with 0.05% trypsin/0.02% EDTA. Trypsin was inactivated by addition of soybean trypsin inhibitor in PBS containing 0.2% BSA. The cells were washed twice with DMEM+10% FBS and resuspended at a concentration of $1 \times 10^6$ cells/ml. The fibroblasts were mixed with 10% FBS, neutralized collagen and concentrated DMEM so that the final concentration of DMEM and sodium bicarbonate was 1×. In some experiments, FBS was replaced by 30 ng/ml PDGF-BB and 2% BSA or dilutions of a reconstituted composition of the invention and 2% BSA. Samples (0.6 ml) of the cell mixture were added to the wells of a 24-well tissue culture plate, which was pre-coated with 2% BSA, and the collagen was allowed to polymerize at 37° C. The final concentration of collagen was about 1.8 mg/ml and each gel contained $6 \times 10^4$ cells. After two hours incubation, the gels were gently detached from the plastic surface to allow contraction, 0.5 ml DMEM+10% FBS per each well was added, and the gels were incubated overnight at 37° C. in 5% $CO_2$. If the collagen gels were contracted by the addition of PDGF-BB, the added medium was supplemented with 30 ng/ml PDGF-BB+2% BSA instead of FBS.

Figure 11:
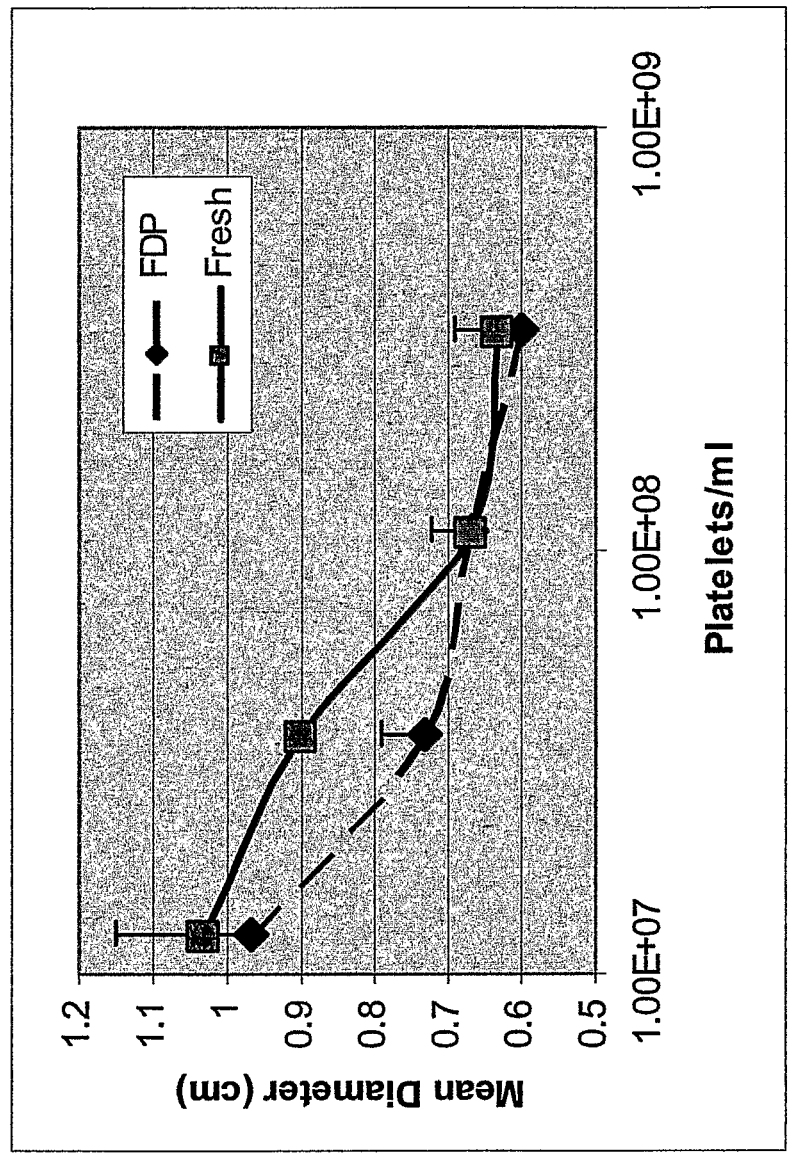
FIG. 11 depicts a graph of results of collagen contraction assays of collagen-fibroblasts matrix remodeling using freeze-dried platelets of the invention.

The results of the collagen contraction assay are depicted in FIG. 11. More specifically, FIG. 11 shows a graph of collagen-fibroblasts matrix remodeling using freeze-dried platelets of the invention. When a mixture of rat tail type I collagen and fibroblasts were incubated in media alone (control), platelet rich plasma (fresh platelets), or a composition (FDP) according to the invention made using Example 4, samples containing the composition of the invention, FDP, and fresh platelets demonstrated collagen re-modelling and contraction, whereas, the control samples showed no contraction.

The experiments depicted in FIG. 11 were conducted to assess the effect of a composition of the invention on wound healing and remodeling. Although it is hard to show tissue remodeling in vitro, culturing of fibroblasts in three-dimensional native type I collagen gels have been used to demonstrate scar formation and tissue remodeling in wound healing. A number of studies previously showed that PDGF and fresh platelet could promote contraction of collagen gels in vitro. As shown in FIG. 11, the composition of the invention, promoted collagen contraction within 24 hours incubation. Thus, a composition of the invention promotes collagen matrix reorganization and fibroblast proliferation, and can achieve, facilitate, or assist in wound healing.

Example 16

Evaluation of the Physical Characteristics of a Composition

The structural composition of a composition prepared according to Example 3 was examined using the Beckman Multisizer 3 COLULTER COUNTER (Fullerton, Calif.), particularly to analyze particle size. The multisizer provides size and volume distributions with a range up to 10 um. As used herein, the volume of a platelet is 2-4 um where as anything less than 1 um is considered to be platelet microparticles.

Figure 12:
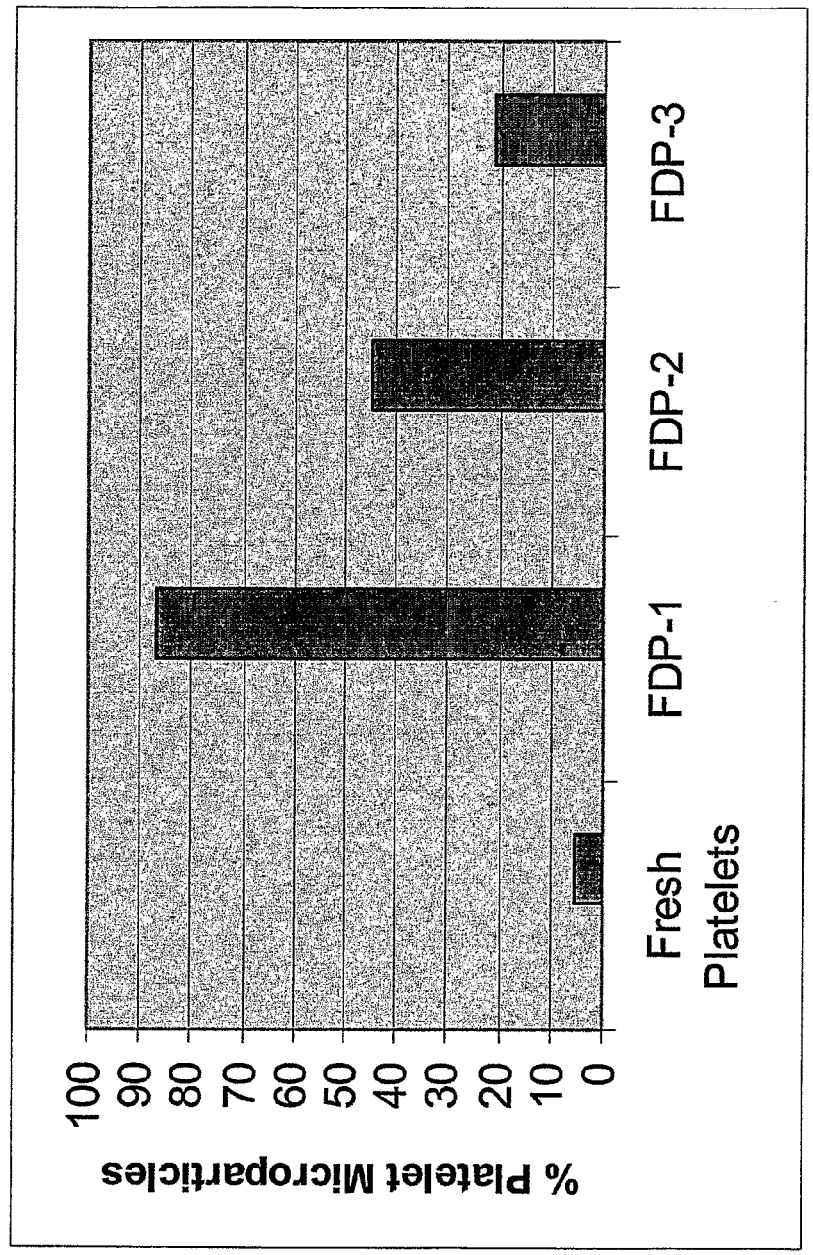
FIG. 12 depicts a graph showing the effect on microparticle concentration of three different protocols for preparing freeze-dried platelets.

FIG. 12 shows a graph of multisizer analysis of the platelet preparation. It shows that the composition is composed of percentage of platelet microparticles within the platelet preparation using Examples 4 and 5. As can be seen from FIG. 12, approximately 10-50% of the total number of particles produced by the method outline in Example 4 are microparticles (samples labeled FDP-2 and FDP-3), whereas, greater than 70% of the total number of particles produced by the method outline in Example 5 are microparticles (FDP-1). Thus, this Example shows that a composition according to the invention, either expose to extreme cold before lyophilization and upon reconstitution with water, showed a mixture of platelet microparticles and intact platelets.

Additionally, the expression of GPIIb/IIIa and other platelet surface markers can be detected on the surface of the platelets and microparticles (data not shown), in the samples made according to Examples 4 and 5, which mediated the binding of components of the composition to solid surfaces coated with fibrinogen in a reversible and specific manner (data not shown).

Example 17

Clotting Function of Freeze-Dried Platelets

To further characterize a composition of the invention, the freeze-dried platelets made by Examples 4 and 5 were tested for their ability to provide clotting functions.

Figure 13A:
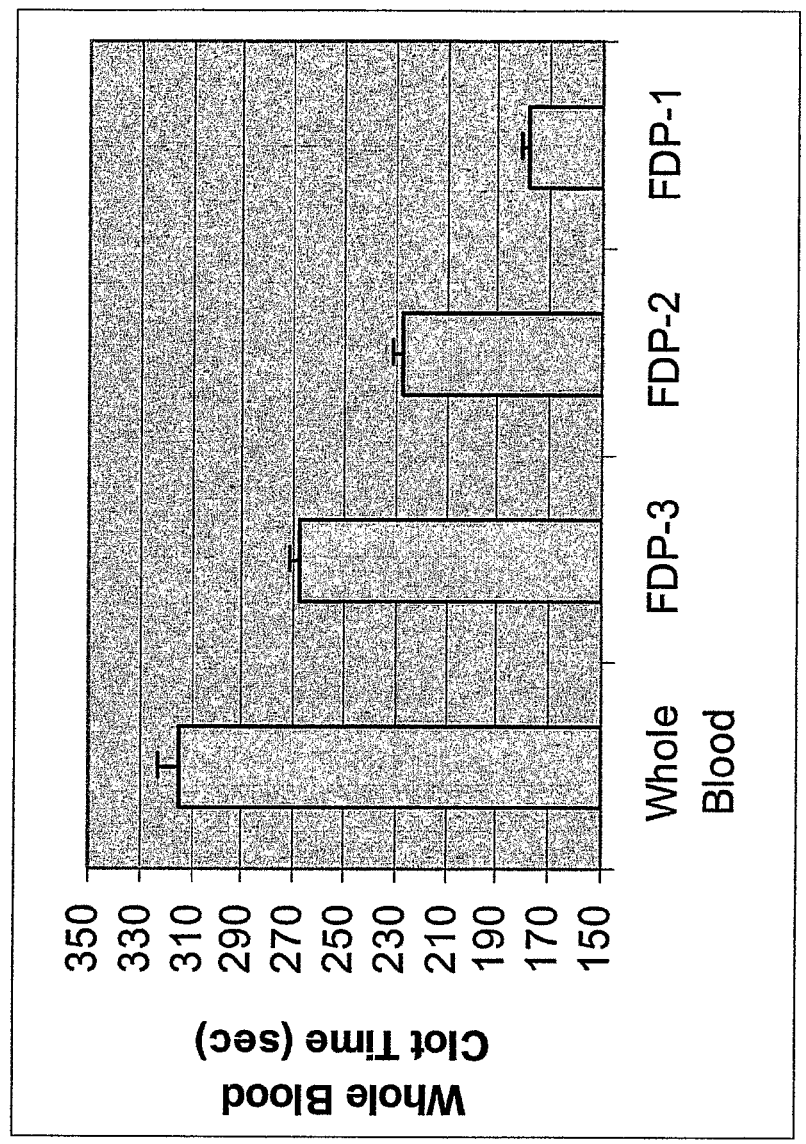
FIG. 13 depicts graphs showing the beneficial effect of higher microparticle concentrations on topical wound healing. Panel A shows the effect of microparticle concentration on clot time of whole blood. Panel B shows the effect of microparticle concentration on plasma.

FIG. 13A depicts the effect of freeze-dried platelets that contained different amounts of microparticles, as depicted in FIG. 12, on the clotting ability of whole blood samples. The data shown in FIG. 13A was obtained as follows: clot time was determined for a mixture containing 400 ul of ACD whole blood, 25 ul of 0.2 M CaCl$_2$, 25 ul saline, and 50 ul for various concentrations of reconstituted (rehydrated) freeze-dried platelets using samples FDP-1, FDP-2, and FDP-3.

As can be seen from FIG. 13A, the results of the whole blood assays showed that the FDP-3 sample, which contained the highest amount of microparticles, provided the shortest clot times, as compared to samples FDP-2 and FDP-3, which contained lower percentages of microparticles.

Figure 13B:
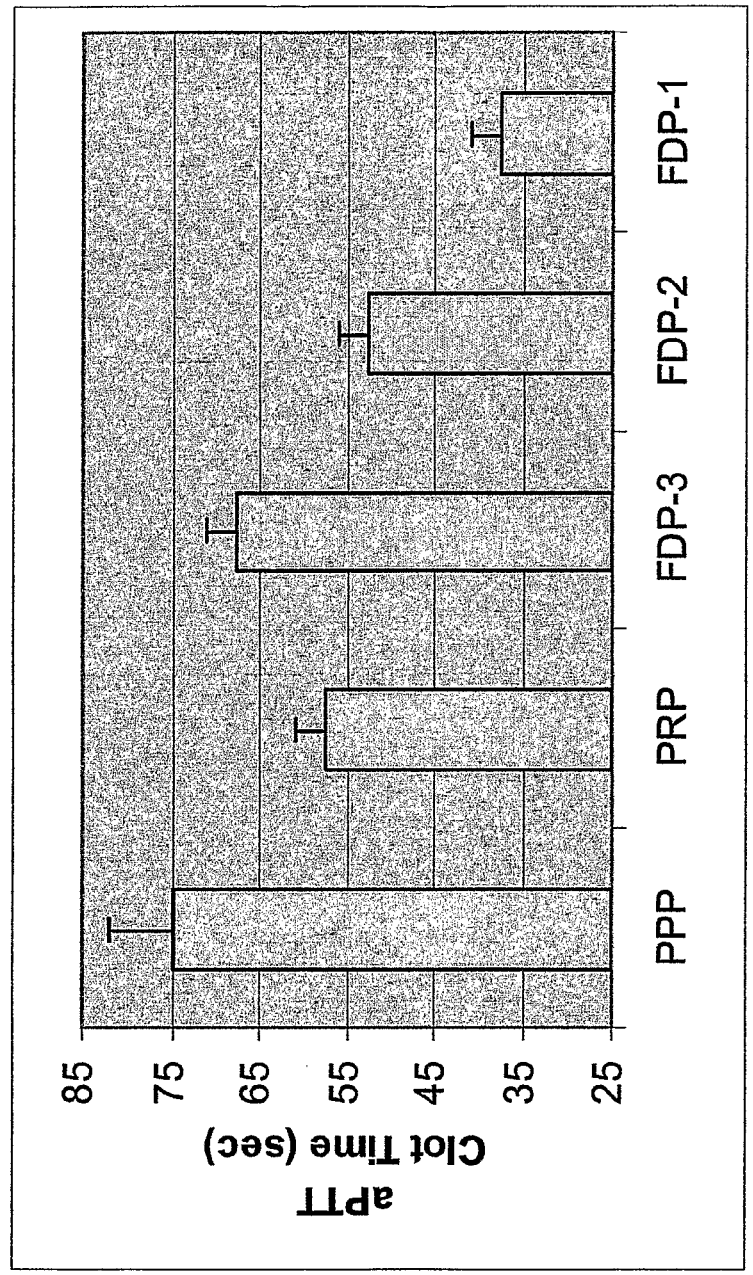

FIG. 13B depicts the effect of freeze-dried platelets that contained different amount of microparticles, as depicted in FIG. 12, on the clotting ability of normal pooled plasma samples. To assay clotting time, 100 ul of APCT (activated plasma clot time, Analytical Control Systems, Inc., Fishers, Ind.) reagent was mixed with 25 ul of various concentrations of water-reconstituted freeze-dried platelets from different preparations, FDP-1, FDP-2, or FDP-3, and 25 ul of factor-deficient plasma obtained from commercial suppliers. The mixture was incubated at 37° C. in a water bath for 3 minutes, then 100 ul of 0.02 M CaCl$_2$ (37° C.) was added, and clot time determined.

As can be seen from FIG. 13B, the results of the plasma based assays showed that the FDP-3 sample, which contained the highest amount of microparticles, provided the shortest clot times, as compared to samples FDP-2 and FDP-3, which contained lower percentages of microparticles.

Example 18

In vivo Studies Using a Composition of the Invention

An experiment was conducted to investigate the hemostatic ability of a composition of the invention, and compare this to the widely use Quikclot™ and Surgicel™ products. The experiment was conducted at Qual Tech Labs, NJ. Sprague Dawley rats were obtained from Hilltop Lab Animals for the study. The test animals were male, adults, same age, and around 350 g in weight. Upon arrival, the animals were placed in quarantine for 48 hours, after which, the animals were housed in pairs in polypropylene cages with wire lids meeting NIH requirements. Animal room temperatures were recorded daily. A 12 hour light/dark cycle was maintained. Purina Rodent Chow and tap water were provided ad lib, except the food was withheld overnight prior to the study. Studies were performed in rats subjected to anesthesia with a 7:1 mixture of Ketamine/Xylazine, which was administered intramuscularly at 0.05 ml/100 grams body weight. Each test animal was placed on a surgery board and secured. The hair on the neck and abdomen were removed and the surgical sites swabbed with betadine. Then, the carotid artery was exposed and isolated. Using suture silk, the artery was tied off arterioly and clamped as far as it is practicable from the tie-off. The artery was catheterized between the tie-off and clamp with a 20 gauge catheter placement unit. The catheter was secured and connected to a WECO blood pressure monitor. The clamp was removed and the blood pressure allowed to stabilize. A midline incision approximately 20 mm long was made in the abdominal wall. The abdominal artery was isolated and suture silk was passed beneath the artery to facilitate location during the study. After that, puncture of the abdominal aorta was made using a 23 gauge needle. Various hemostatic agents, including a composition of the present invention, were applied onto the bleed site. This was compared to the control group. Survival was assessed and vital signs, such as systolic blood pressure, heart-rate, and oxygen saturation, were monitored over a 30-minute period. The rodents were euthanized at the end of the study.

Figure 14:
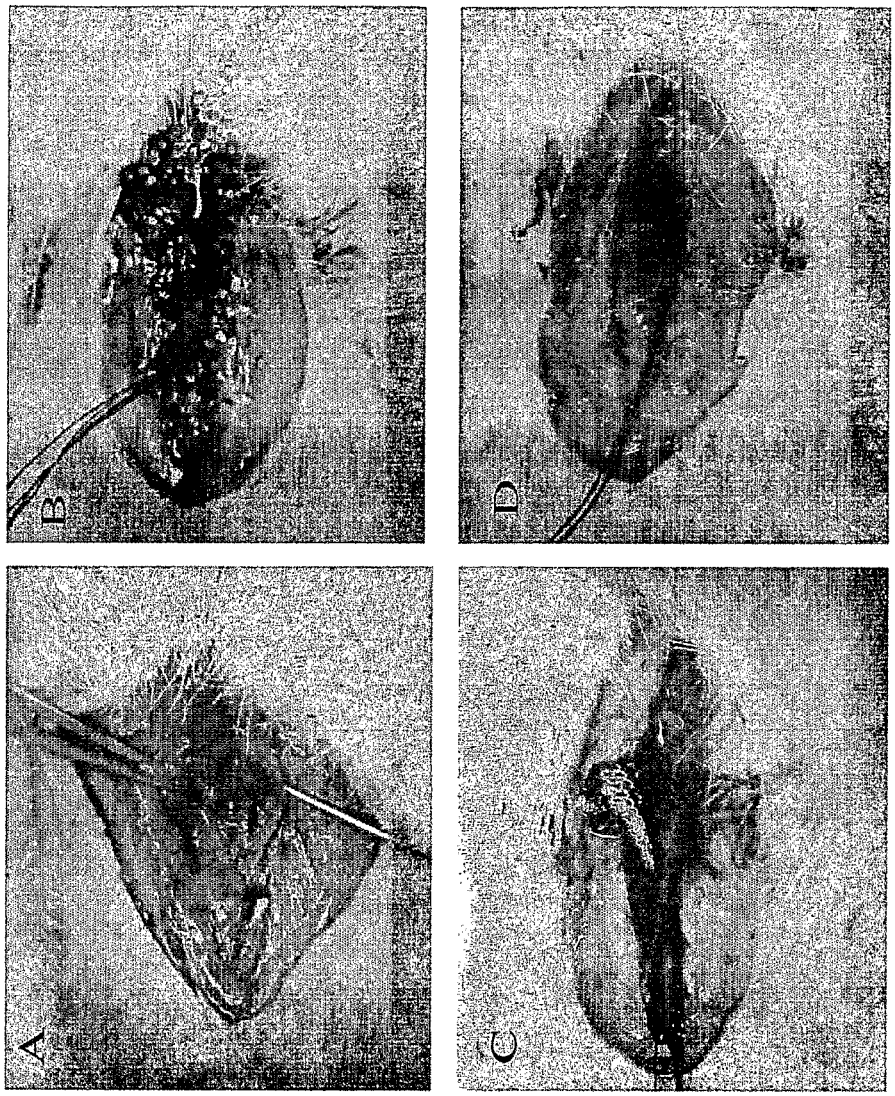
FIG. 14 shows pictures that compare bleeding control between Surgicel™, QuikClot™, and a composition of the present invention. Panel A shows abdominal aortic artery puncture site; Panel B shows the effect of QuikClot™ on bleeding of the aortic artery; Panel C shows the effect of Surgicel™ on bleeding; and Panel D shows the effect of a composition of the present invention on bleeding.

FIG. 14 shows pictures that compare bleeding control between Surgicel™, QuikClot™, and a composition of the present invention. FIG. 14A provides a reference photograph showing the site of artery wounding. As shown in FIG. 14B, when the artery was punctured with a needle and then Quik-Clot™ (2 grams) immediately applied to the injury site, the hemostatic agent failed to arrest bleeding, even after 2 minutes into the procedure, as is evidenced by blood still oozing out of the wound at that time. As shown in FIG. 14C, application of Surgicel™ as the hemostatic agent showed the same pattern, with bleeding continuing more than two minutes after application of the hemostatic agent. In contrast, when a composition of the present invention, produced according to the procedure in Example 5, was used, bleeding was diminished rapidly, and bleeding stopped well within two minutes of application to the wound site (FIG. 14D). Based on this data, it was concluded that the hemostatic agent of the present invention is superior to other agents available in the art, and is capable of arresting bleeding, even heavy arterial bleeds, whereas other hemostatic agents are not capable of doing so.

Figure 15:
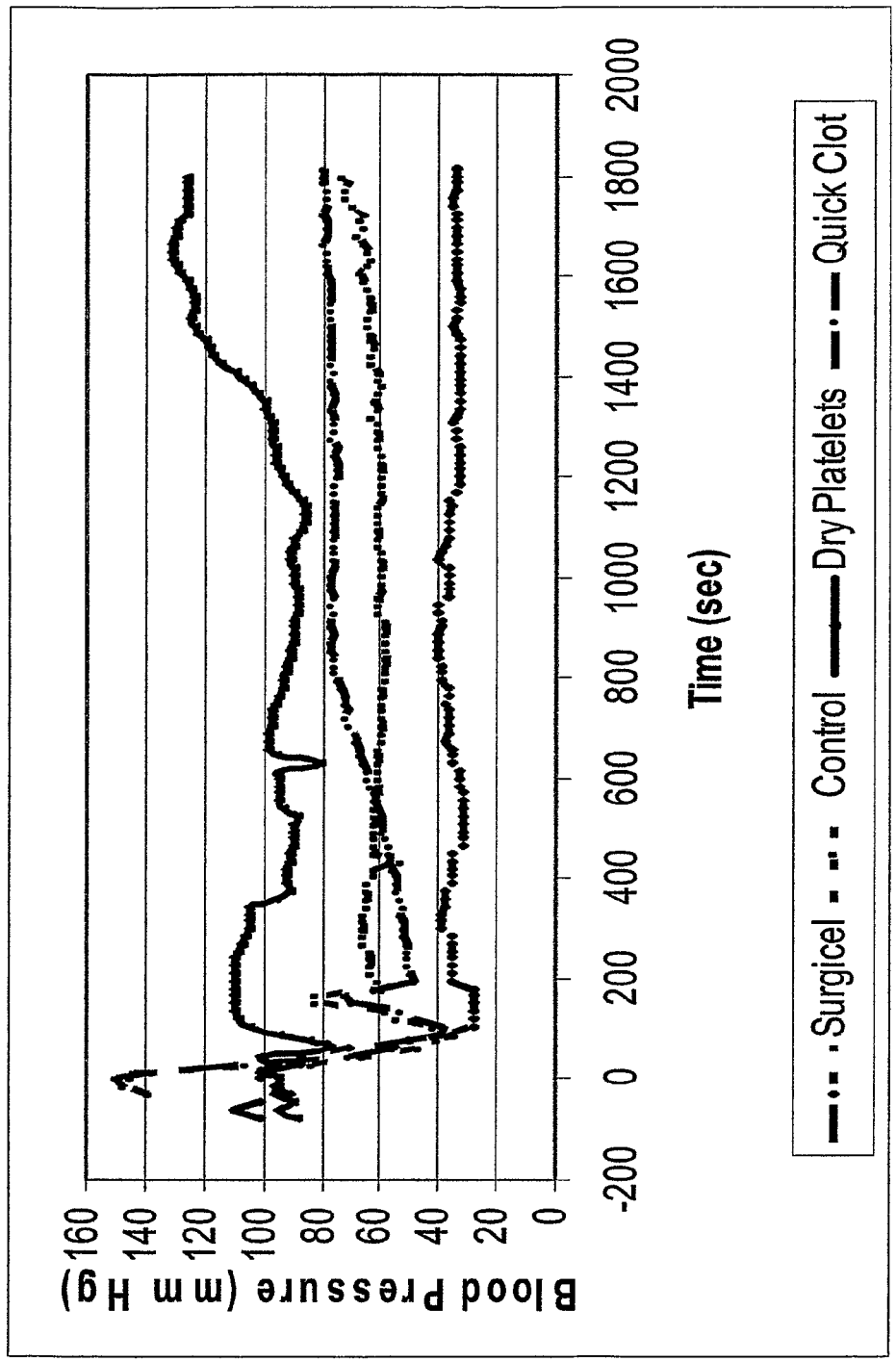
FIG. 15 shows graphs of the blood pressure of rodents having had their abdominal aorta punctured, then treated with freeze-dried platelets of the invention, Surgicel™, QuikClot™, of no hemostat or pressure applied to the bleeding site (control).

To further assay the effects of a composition of the invention in vivo, the vital signs of the rats used in the above experiment were monitored by monitoring the systolic blood pressure, mean blood pressure, and heart-rate over a 30-minute period. FIG. 15 shows a graph of the mean blood pressure of rodents having had their abdominal aorta punctured, then treated with freeze-dried platelets of the invention, Surgicel™, and QuikClot™, with a control (no pressured applied to the bleeding site). Blood pressures were measured using a WECO monitor for 30 minutes. Animals were sacrificed after the procedure.

As shown in FIG. 15, the mean blood pressure of animals in group Surgicel™ and Control (no pressured applied to the bleeding site) never recovered after the puncture procedure. Animals in the QuikClot™ group did regain some pressure, but were not able to return to normal. On the contrary, when treated with a composition of the present invention, normal pressure returned within 1200-1400 seconds after the puncture procedure, and it was stabilized for the duration of the study.

The heart rates of the rodents were monitored and it was found that only in the group treated with the composition of the present invention were heart rates quickly returned to normal (the Control, Surgicel™, and QuikClot™ failed to do so).

The animals were continually visually monitored throughout the procedure. Despite the fact that all animals survived past 30 minutes, the animals in groups Surgicel™, Quik-Clot™, and Control struggled to breath, and had very faint heart rates. In contrast, animals treated with the composition of the present invention were breathing normally with almost normal heart rates. Based on this data, it was concluded that compositions of the invention can be potent in vivo hemostatic agents.

It is clear from the data, that a composition of the invention retained a majority of its physical surface structure and integrity. Furthermore, the composition could participate in collagen remodeling and fibroblast proliferation (see earlier Examples). Without being constrained to any particular theory, it is possible that a natural pool of growth factors could have been contained within the composition, and could aid in wound treatments as well as cell and tissue regeneration.

All of these indications might suggest that the compositions of the invention comprise a unique mixture of platelets and platelet microparticles at a defined ratio. Furthermore, the data also showed that the compositions of the invention were able to quickly seal the high pressure hemorrhaging aortic artery quickly and effectively when applied to it. In addition, this hemostatic activity is superior to QuikClot™ or Surgicel™ and proven to be useful and effective as a hemostatic agent that is capable of stopping bleeding at a high pressure, non-compressible bleeding site.

Example 19

Further Analysis of In Vivo Characteristics

To further assay the properties of a composition made in accordance with Example 4, further in vivo wound healing studies were performed, and analyses of cells from these studies were carried out. For in vivo wound healing studies, diabetic mice (male Lepr db+/+), were used. Thirty animals were ordered and kept five per cage until the wound site was excised. Anesthesia (Nembutal/Pentobarbital) was administered intraperitoneally at a dose of 60 mg/kg. Depth of anesthesia was assessed by pinching the animals' toes and assessing for flexor withdrawal. The back of the anesthetized mouse was shaved using an electric razor. Any remaining traces of hair were removed with hair removal lotion (calcium hydroxide based) applied briefly to the skin and then rinsed with warm saline. Prior to surgery, the shaved skin was cleaned with betadine and then wiped with 70% EtOH. A 1×1 cm$^2$ full-thickness wound was excised from the hairless dorsum of the mouse, as follows. The skin was lifted using forceps and incised using scissors. Lifting the skin ensured that the incision moved through the panniculus carnosus. Following the first cut, the partially removed skin area was held using forceps and the excision was completed with two or three additional cuts. After completion of excisional wounding, the animals were divided into test groups (ten animals per group), and corresponding test materials were applied on the wound bed. Ten animals received an occlusive dressing only; ten received a single application of 5×10$^8$ FDP given on the day of surgery; ten received applications of 5×10$^8$ FDP given on the day of surgery and on days 2, 5, 9, and 12 following surgery. Benzoin Tincture Compound was placed around the edges of the wound and Tegaderm was placed to cover the wound. Following the surgery, mice were given Buprenorphine 0.05 mg/Kg$^2$ every 12 hours for 24 hours for postoperative analgesia, and then daily as needed. After complete recovery from anesthesia, mice were transferred to the Animal Core Facility, where they were singularly caged, and then monitored twice a day. Mice were monitored for inactivity, appetite loss, and the wounds were inspected. Wound measurements were taken every other day for the duration of the study. One animal from each group was sacrificed on these days using gas $CO_2$ inhalation. Blood, kidney, and liver samples were harvested from the animals for immunogenic studies and the wound site was removed for immunohistological analysis. Any animals that developed wound infection were excluded from the study.

Figure 16:
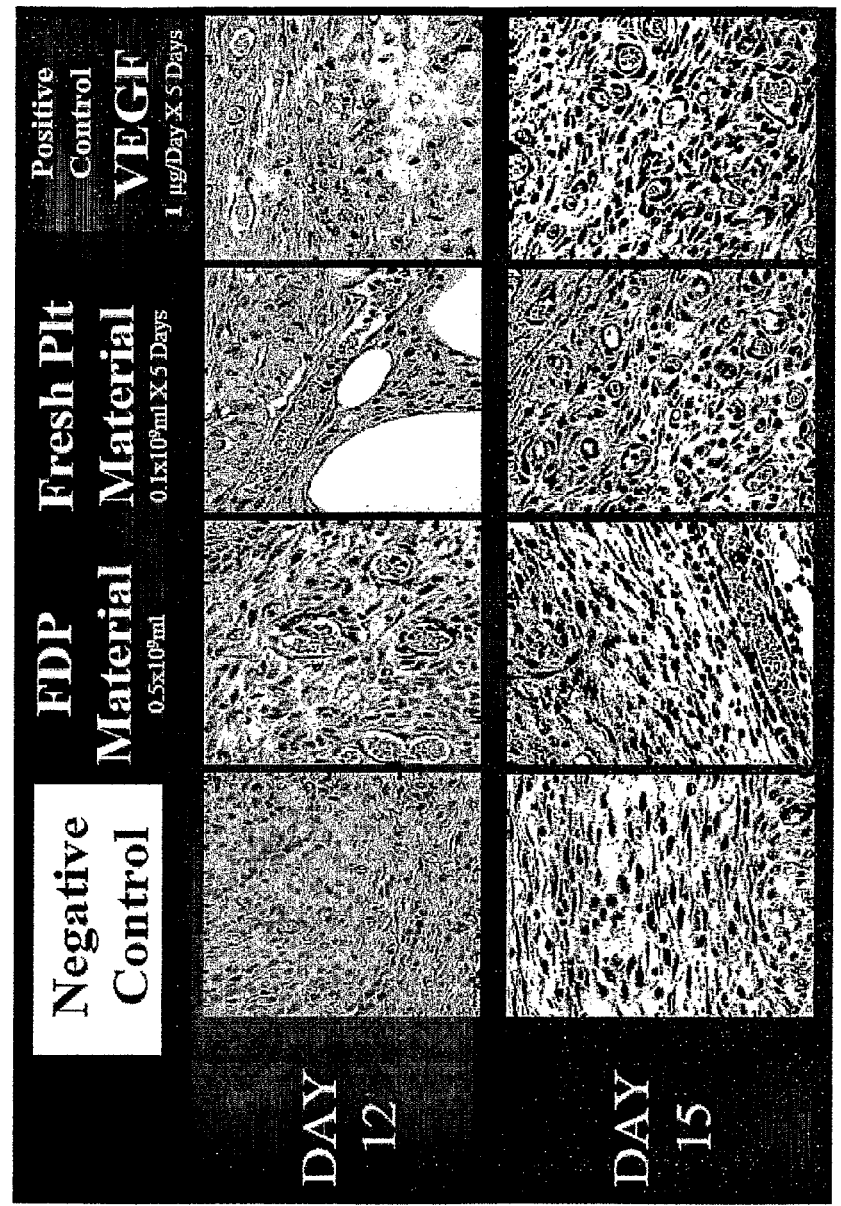
FIG. 16 depicts pictures of microscopic views of the wound beds of wound sites treated with an occlusive dressing, freeze-dried platelets of the invention, or VEGF.

The immunohistological analysis of the wound bed is presented in FIG. 16. The data was developed as follows: The tissue at the wound bed was removed from one animal of each group every third day for staining. Stained sections were scanned at low power to identify areas with the most intense neovascularization. To evaluate neovascularization, 3 fields per slide at 40× magnification were systematically taken, one in the middle of the lesion and two at wound edges.

Careful examination of the wound bed tissue under a microscope revealed that groups that received FDP, fresh platelets, and VEGF underwent intense neovascularization. The newly formed blood vessels can be found at the wound edges as well as in the middle section. When the absolute numbers of blood vessels were counted, the number of blood vessels in the samples that received FDP, fresh platelets, and VEGF were virtually identical. As can be seen in FIG. 16, a microscopic view of the wound bed of the Occlusive Dressing, Single Dose, and Multiple Dose treatment groups at days 1, 9 and 15, shows increased vascularization.

Figure 17:
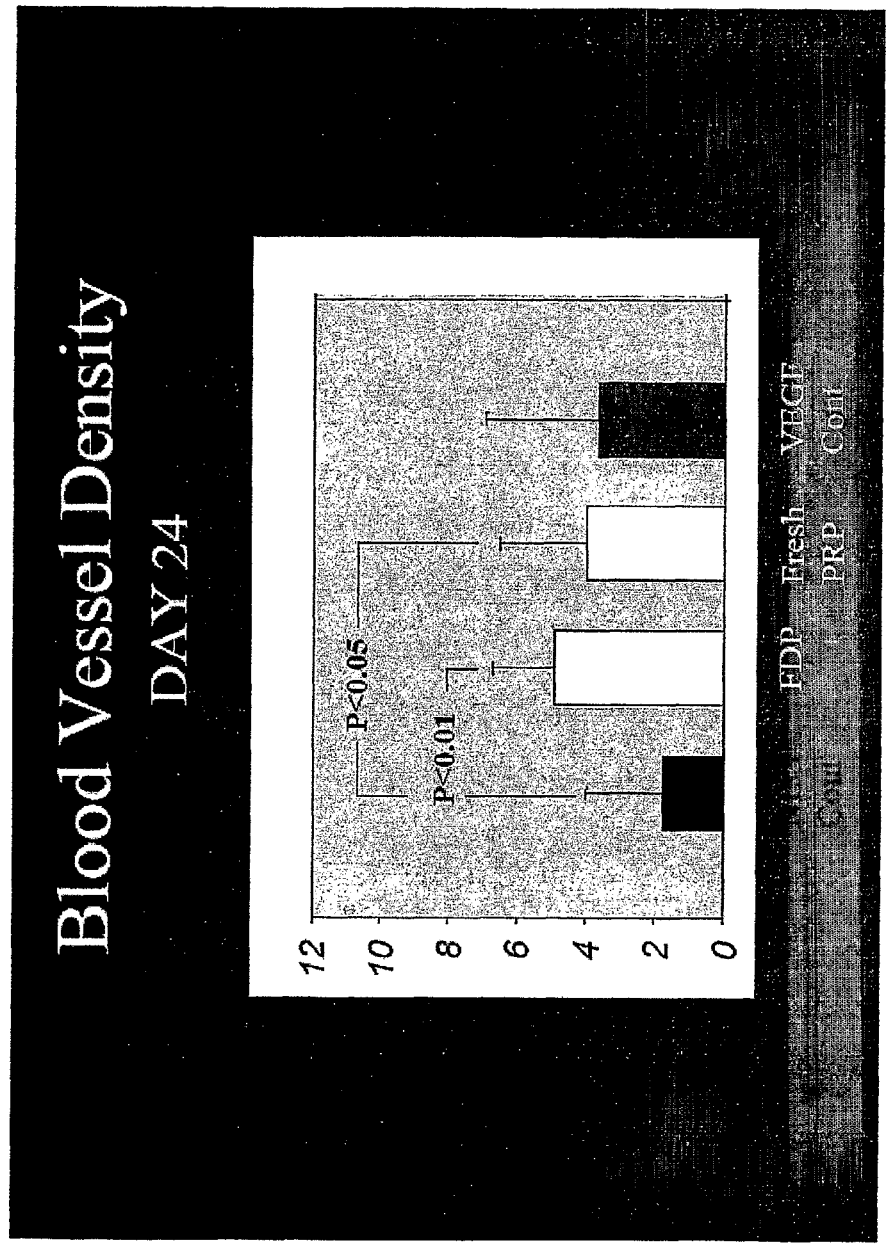
FIG. 17 depicts a graph of quantification of the results of vascularization shown in FIG. 16.

FIG. 17 depicts the data of FIG. 16 graphically. More specifically, FIG. 17 depicts a bar graph quantifying the number of vessels in the wound bed tissue. Because the wound tissues required blood vessels to heal, the application of freeze-dried platelets to the wound bed not only supplied the needed growth factors for tissue regeneration but also stimulated the growth of new blood vessels. This data indicated that the number of blood vessels generated by the composition is similar to that of fresh platelets and VEGF control. Thus, freeze-dried platelets are an effective wound healing agent.

Example 20

Evaluation of Wound Closing Rate and Multiple Dosing

For this Example, a study was conducted to determine the effect of multiple applications of freeze-dried platelets on wound healing compared to animals that received only a 1-time dose on the day of surgery and animals that received an occlusive dressing only. For the Multiple Dose FDP group, animals received 5 applications of $5 \times 10^8$ platelets given on the day of surgery and days 2, 5, 9, and 12 following surgery. For the Single Dose FDP group, animals received a 1-time application of $5 \times 10^8$ platelets given on the day of surgery. Animals in the Occlusive Dressing group did not receive any platelets.

Figure 18:
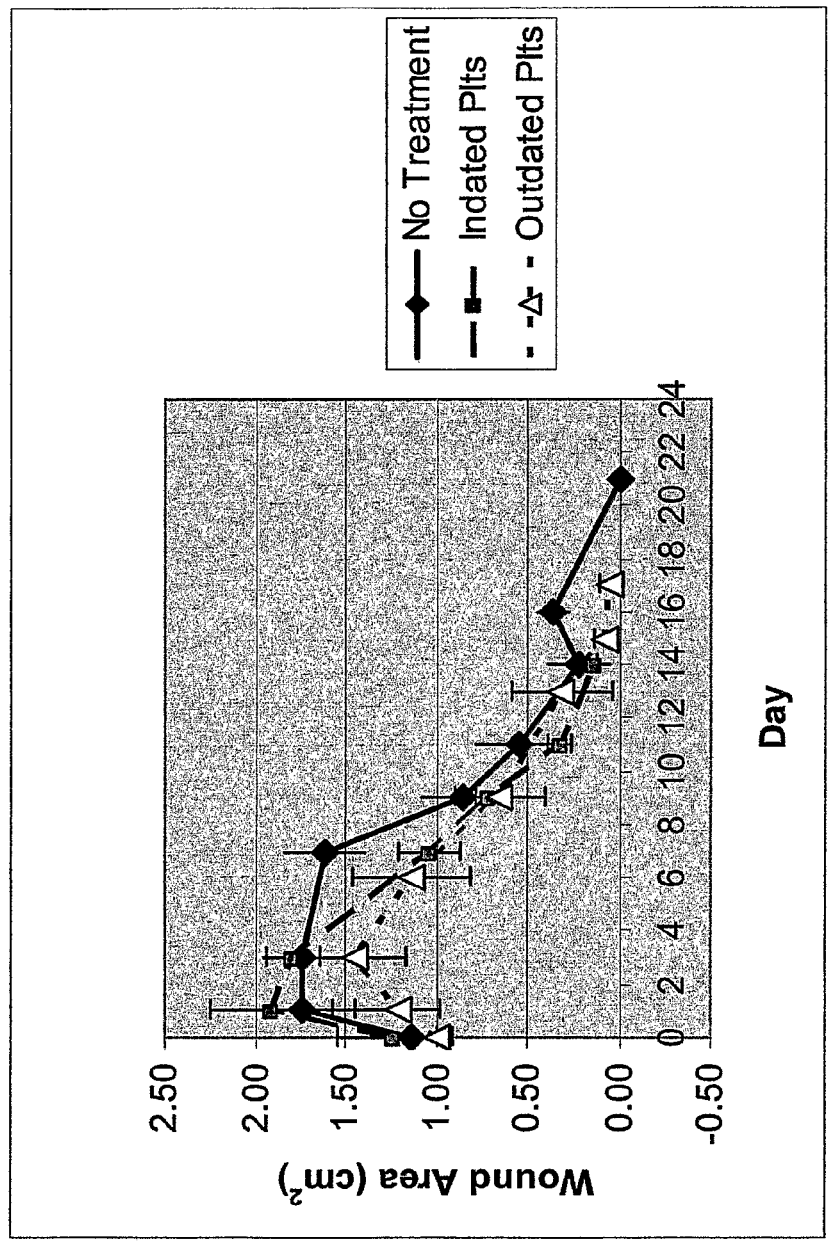
FIG. 18 depicts a graph comparing different treatment regimens in wound healing.

The results of the study are shown in FIG. 18. The Figure shows that animals in the Multiple Dose FDP group demonstrated a much faster rate of wound closure, requiring only 16 days for complete closure. The Single Dose and Occlusive Dressing groups had a much slower rate of wound closure, requiring 17 and 21 days for complete closure. More specifically, wound measurements were taken every other day (or every three days). By day 16, the Multiple Dose group had nearly achieved complete wound closure, while the Single Dose and Occlusive Dressing groups required at least 17 and 21 days, respectively. It is also significant that the Multiple Dose group demonstrated a smaller average wound area than the Single Dose and Occlusive Dressing groups throughout the duration of the study.

Example 21

Evaluation of Wound Closure Rate and Single Dosing Using In-Dated and Out-Dated Platelets To determine the suitability of various types of platelets and platelet preparations for in vivo therapeutic uses, platelets were assayed for their ability to close wounds in single doses. Initially, platelets one day outdated were prepared according to Example 4. Briefly, platelets were collected into acid citrate dextrose (ACD) anticoagulant buffer (1.5 volumes+8.5 volumes blood). Platelet Rich Plasma (PRP) was obtained by low speed centrifugation 135×g for 15 minutes to remove red blood cells. The PRP was acidified to pH 6.5 by adding 1/14 volumes of ACD and then pelleted by centrifuge at 1000×g for 10 minutes. The platelet pellet was resuspended in 1 ml of Cation-Free Tyrodes Buffer containing 50 mM Trehalose, pH 6.8 and adjusted to $1 \times 10^9$ platelets/ml. The mixture was incubated for 2 hours at 37° C., mixing once each half hour. Finally, the albumin concentration was adjusted to 5% of platelet preparation for lyophilization.

Figure 19:
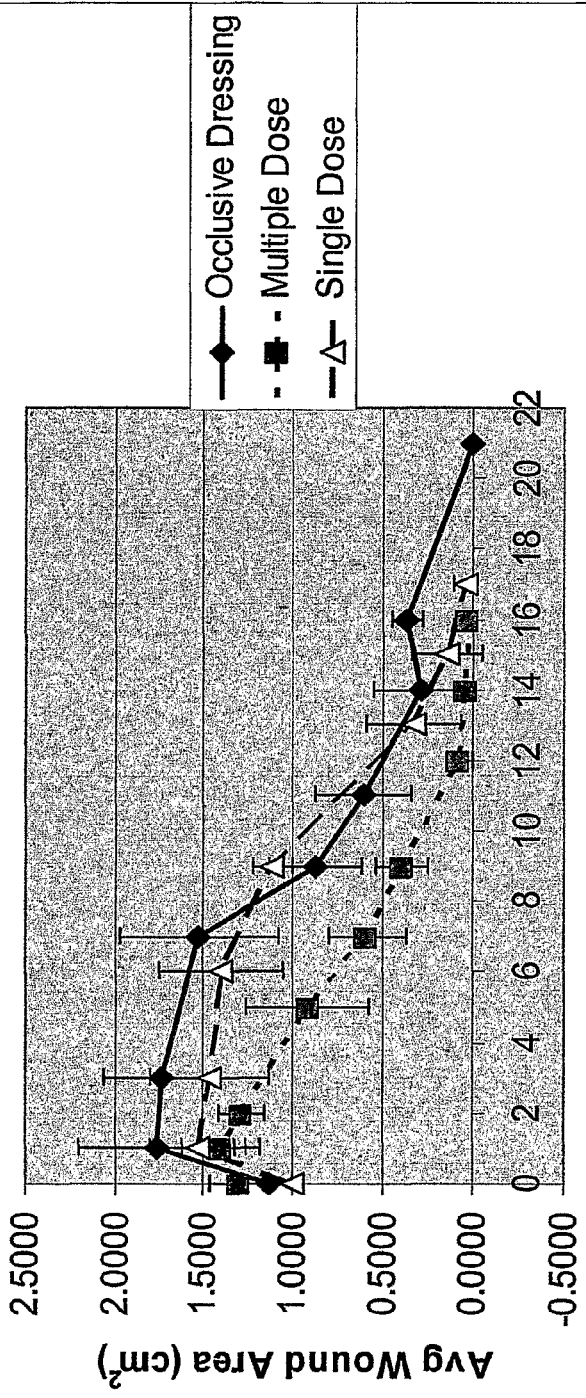
FIG. 19 depicts a graph comparing the effectiveness in treating wounds of in-dated and out-dated platelets as sources for freeze-dried platelets.

For the study, the effect of a single dose application to animals of either in-dated or out-dated FDP on wound healing was compared to the effect of an occlusive dressing only. For the FDP group, animals received one application of $5 \times 10^8$ platelets given on the day of surgery. Animals in the Occlusive Dressing group did not receive any platelets. Wound measurements were taken every other day (or every three days). As can be seen from FIG. 19, single doses of either in-dated or out-dated freeze dried platelets of the invention required 17 days to completely heal the wound. In contrast, and in agreement with the results presented above, Occlusive Dressing groups required 21 days to completely heal the wounds. Thus, there is no difference in wound healing capability between in-dated and out-dated platelets, and both are superior to occlusive dressing techniques.

Example 22

A Delivery System for Compositions of the Invention

A composition according to the invention was formulated to be suspended in compressed air for use in an aerosol system. In this system, the compressed air acted as a propellant to force the platelet composition onto a site of bleeding. In the system, the air pushed down on the composition, forcing the composition through the dip tube of the aerosol system and through a valve when opened. The spray device contained a nozzle that inserted into the abdominal cavity through the wound site. The resulting spray, which contained a composition of the invention, acted on the bleed site to stop bleeding.

Example 23

Evaluation of the Physical Characteristics of a Composition

The structural composition of a composition prepared according to Example 2 was examined further using the Beckman Multisizer 3 COULTER COUNTER (Fullerton, Calif.), particularly to analyze particle size. The multisizer provides size and volume distributions with a range up to 10 um. As used herein, the volume of a platelet is 2-4 um where as anything less than 1 um is considered to be a platelet microparticle.

Figure 20:
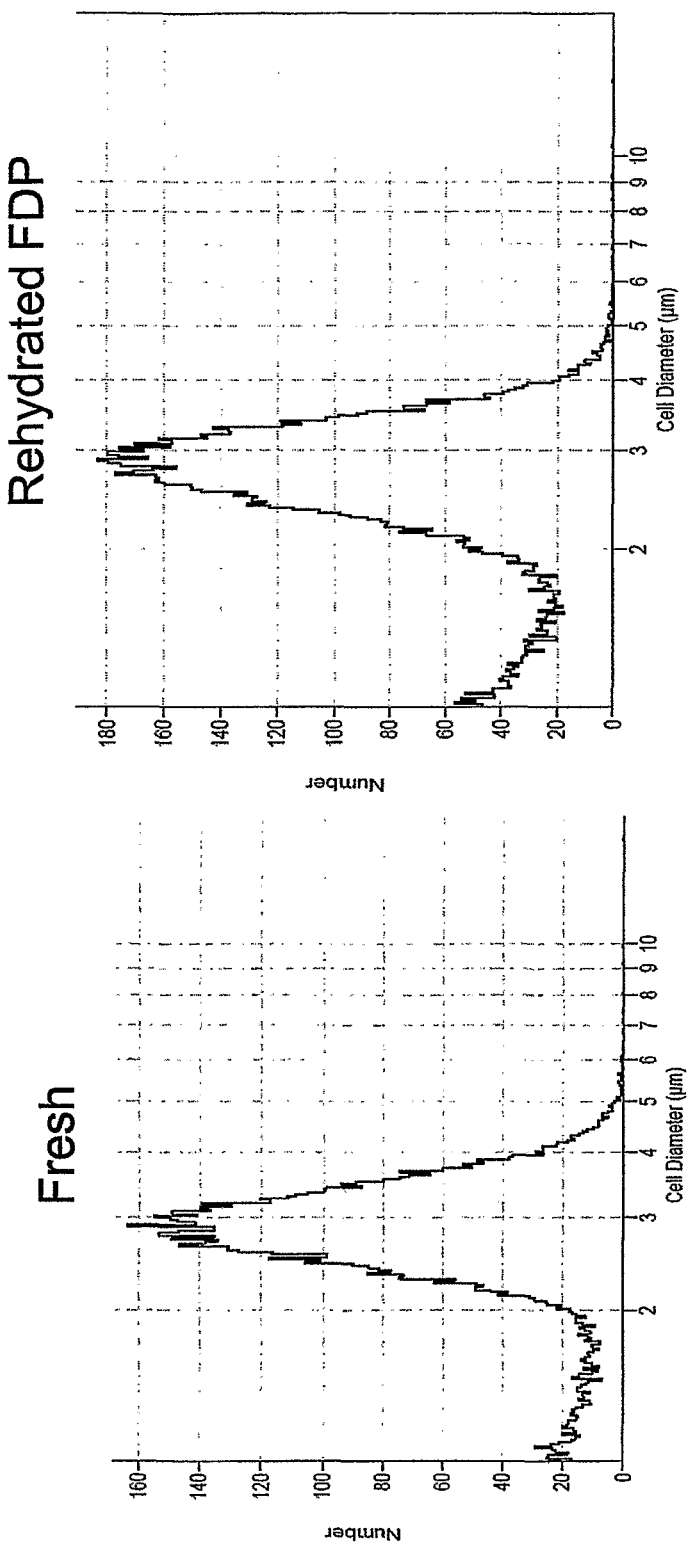
FIG. 20 depicts the size distribution of rehydrated freeze-dried platelets, a composition of the invention, and freshly isolated platelets.

It is clear from the data presented in FIG. 20, which corroborates the data in FIG. 4, that a composition of the invention, upon reconstitution with water, retained a size similar to fresh platelets. Furthermore, as can be seen from FIG. 20, the protocol for preparing freeze-dried platelets can result in a composition comprising mostly platelets and, to a small extent, some microparticles. More specifically, FIG. 20 depicts the results of analyses of size ranges of compositions prepared according to the method disclosed in Example 2. Upon rehydration, the rehydrated particles showed a mixture of platelets and platelets microparticles, as evidenced by the sizing data (FIG. 20). It is estimated that the percentage of microparticles is somewhere between about 1-20% of the total number of particles in the composition.

Example 24

Use of Freeze-Dried Platelets as Calibrating Reagents for Normal Pooled Plasma

As discussed above, it has been found that freeze-dried platelets can be used to monitor functions of platelets. In this vein, the ability of freeze-dried platelets to participate in blood clotting was determined. To do so, various amounts of freeze-dried platelets were mixed with plasma pooled from numerous normal donors, and the time required to generate a clot was determined.

To assay clotting time, 100 ul of APCT (activated plasma clot time, Analytical Control Systems, Inc., Fishers, Ind.) reagent was mixed with 25 ul of various concentrations of water-reconstituted freeze-dried platelets and 25 ul of normal pooled plasma obtained from commercial suppliers. The mixture was incubated at 37° C. in a water bath for 3 minutes, then 100 ul of 0.02 M $CaCl_2$ (37° C.) was added, and clot time determined.

Figure 21:
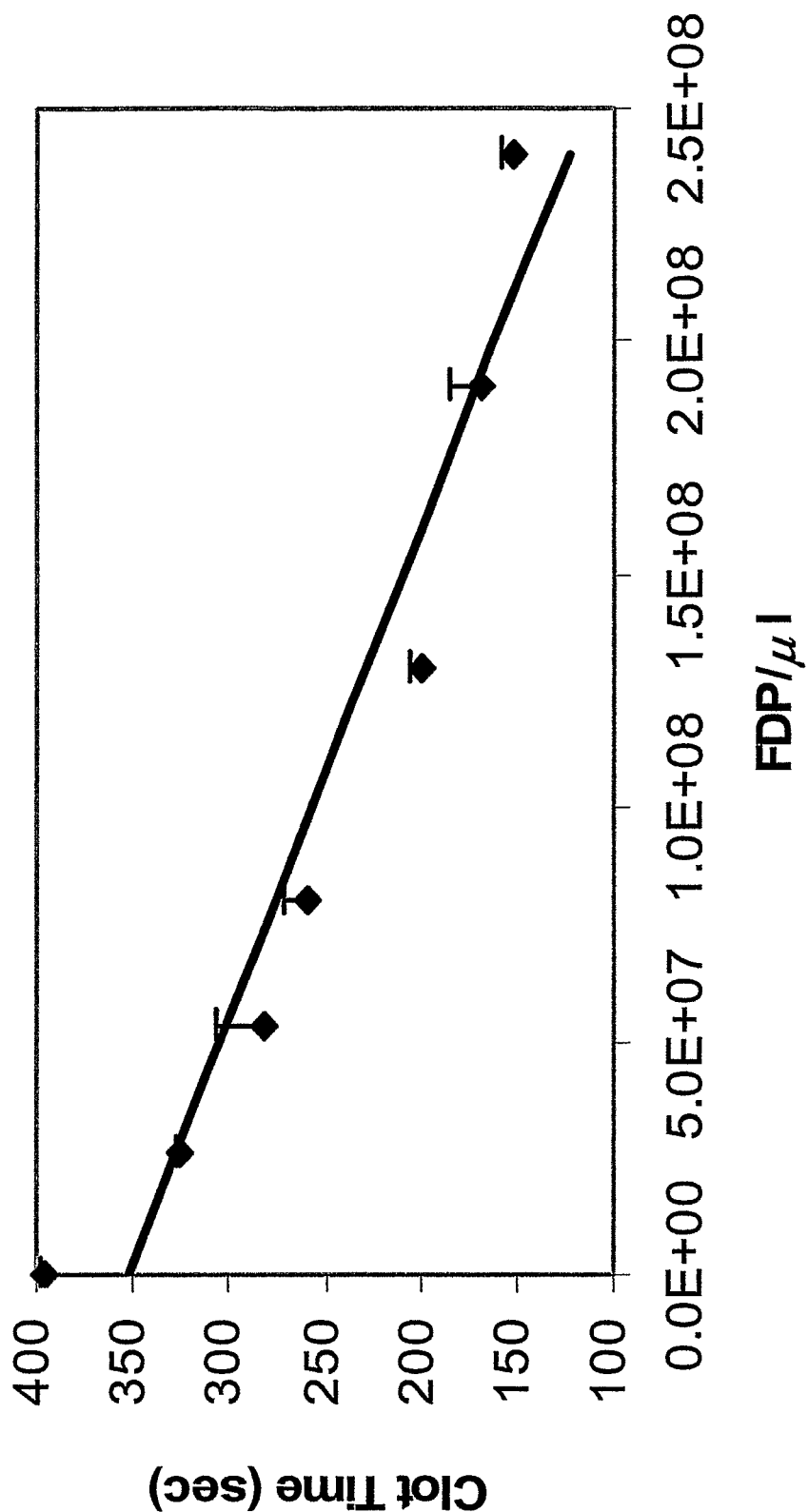
FIG. 21 depicts a standard curve of freeze-dried platelets vs. clotting time using normal pooled plasma.

As can be seen from FIG. 21, the amount of freeze-dried platelets added to a given amount of normal plasma yields a standard curve in which clot time is proportional to the amount of freeze-dried platelets. Thus, the freeze-dried platelets can not only participate in clot formation, but can be used to identify normal clotting times for plasma. By comparison to the normal time for clotting for a given amount of freeze-dried platelets and plasma, one can identify anomalies in the blood clotting abilities of individual samples, such as those obtained from patients having or suspected of having a disease or disorder of the blood clotting system.

A standard clotting assay relies on platelet factor 3 (phospholipid) to activate the intrinsic coagulation mechanism. Other assays use fresh platelets to supply the phospholipid component. In the present invention, the phospholipid is supplied by freeze-dried platelets rather than fresh platelets. Thus, the experiments show not only that freeze-dried platelets have similar physical properties as fresh platelets, but that they have similar functionalities as well.

Example 25

Use of Freeze-Dried Platelets as Calibrating Reagents for Platelet Poor Plasma

The concept of the ability of freeze-dried platelets to give standard clotting time responses when mixed with normal plasma was extended to determine if freeze-dried platelets could serve as a calibrating agent for platelet-poor plasma. That is, previous experiments proved that freeze-dried platelets could participate, in a reproducible and predictable way, in blood clotting in mixtures containing normal plasma. Experiments were performed to determine whether freeze-dried platelets could likewise participate in clotting reactions in conjunction with plasma that was abnormal in that it was deficient in platelets. Platelets were purposely removed from the plasma, and freeze-dried platelets were added in order to replace the fresh platelets. The count of fresh platelets in the sample was negligible (about 5000 platelets/ul).

Figure 22:
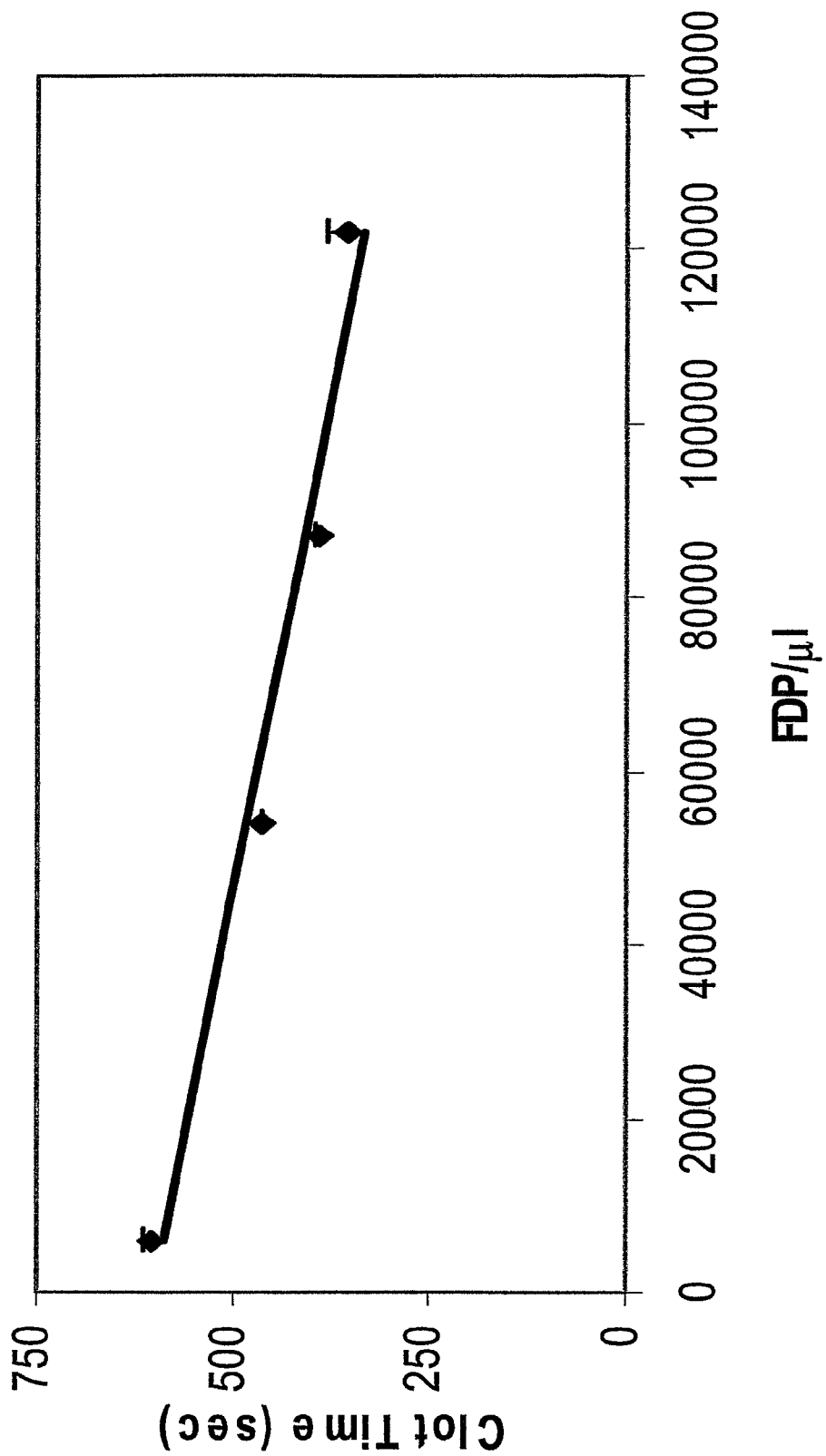
FIG. 22 depicts a standard curve of freeze-dried platelets vs. clotting time using platelet-poor plasma.

As can be seen from FIG. 22, the amount of freeze-dried platelets added to a given amount of platelet-poor plasma yields a standard curve in which clot time is proportional to the amount of freeze-dried platelets. Thus, the freeze-dried platelets can not only participate in clot formation in platelet-poor plasma, but can be used to identify clotting times for such plasma. By comparison to the normal time for clotting for a given amount of freeze-dried platelets and normal plasma, one can not only identify anomalies in the blood clotting abilities of individual samples, such as those obtained from patients having or suspected of having a disease or disorder of the blood clotting system, but one can also quantitate the number of platelets in the platelet-poor sample. Indeed, one conclusion that can be drawn from this experiment is that, in plasma without any platelets (or plasma with extremely low platelet counts), freeze-dried platelets can be used as a calibrating agent to calibrate for other blood components (i.e., coagulation factor inhibitors or any other defect within the coagulation pathways). In normal plasma, freeze-dried platelets can also be used as a calibrating agent for the same purpose. The system disclosed here uses freeze-dried platelets as a reagent in any given plasma samples independent of platelets present to probe for coagulation protein defects or to probe for certain coagulation inhibitors. For example, in hemophilia plasma, freeze-dried platelets were used on frozen plasma with various defects and were able to identify and correct factor IX, X, and XI defects, but not factor VIII and II defects. One value in this is that a lab can receive frozen plasma and using this freeze-dried platelet reagent to rapidly determine coagulation protein defects.

This Example shows that, in plasma with out any platelets (or plasma with extremely low platelet counts), freeze-dried platelets can be used as a calibrating agent to calibrate for other blood components (i.e., coagulation factor inhibitors or any other defect within the coagulation pathways). It is evident then that, in normal plasma, freeze-dried platelets can also be used as a calibrating agent for the same purpose. The system can use freeze-dried platelets as a reagent in any given plasma sample, independent of whether platelets are present, to probe for coagulation protein defects or to probe for certain coagulation inhibitors. For example, in the hemophilia plasma, freeze-dried platelets were used with frozen plasma having various defects. The combination was able to identify and correct factor IX, X, and XI defects. Correction of defects in factor VIII and II were not shown, however. One advantage of this system is that a lab can receive frozen plasma and, using the freeze-dried platelets and systems of the present invention, rapidly determine coagulation protein defects.

Example 26

Use of Freeze-Dried Platelets as Diagnostic Reagent for Coagulation Factor Defects With the knowledge that freeze-dried platelets can be used to identify defects in clotting ability of plasma, experiments were designed to determine whether freeze-dried platelets can be used to identify specific defects in the blood clotting pathway. To assay clotting time, 100 ul of APCT (activated plasma clot time, Analytical Control Systems, Inc., Fishers, Ind.) reagent was mixed with 25 ul of various concentrations of water-reconstituted freeze-dried platelets and 25 ul of factor deficient plasma obtained from commercial suppliers. The mixture was incubated at 37° C. in a water bath for 3 minutes, then 100 ul of 0.02 M $CaCl_2$ (37° C.) was added, and clot time determined.

Figure 23:
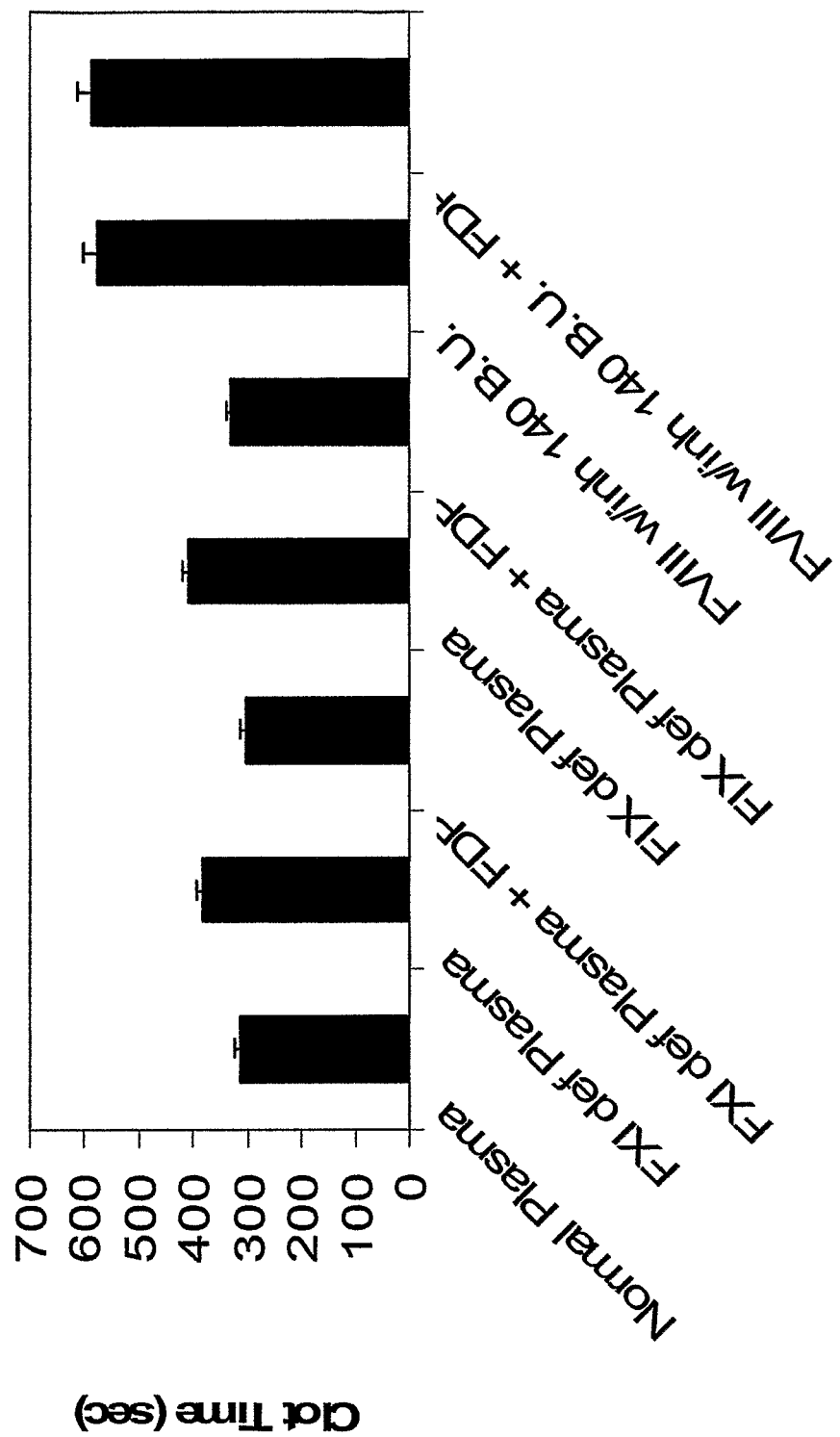
FIG. 23 depicts detection of clotting defects in hemophilia plasma.

As can be seen in FIG. 23, freeze-dried platelets can overcome the clotting deficiencies of defects in clotting factors XI, X, and IX, but not VIII. Thus, assays can be performed to distinguish between clotting defects based on factor VIII as compared to factors XI, X, and IX, and can identify deficiencies in the intrinsic pathway of clot formation. Because freeze-dried platelets can overcome factor XI, X, and IX defects, a calibration curve can be set up to accurately determine the amount of these factors' presence or absence in blood. By the same token, for patients on warfarin (coumadin), where vitamin-K dependent factors are compromised, freeze-dried platelets can be used to monitor for the deficiency.

Example 27

Figure 24:
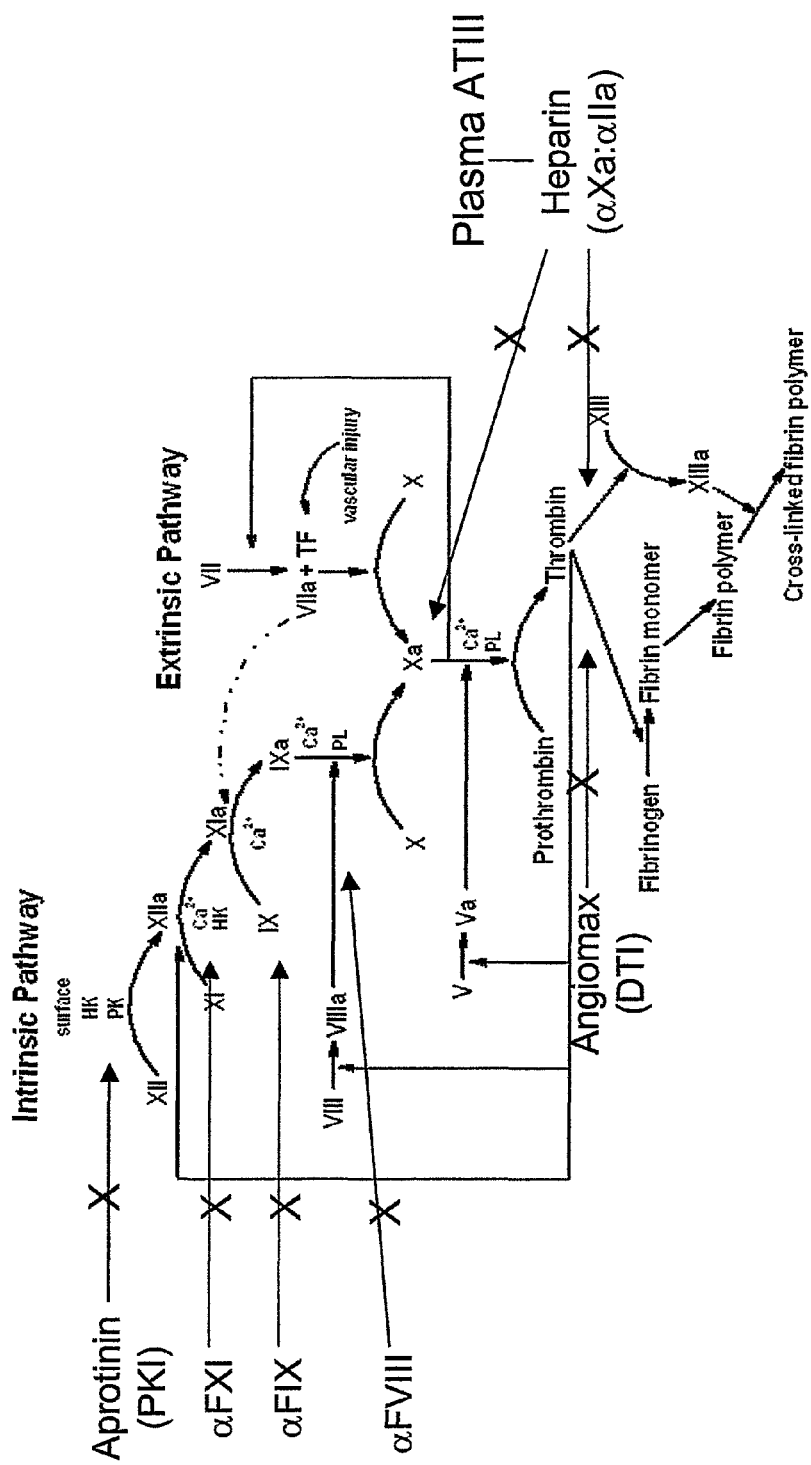
FIG. 24 depicts a general schema for coagulation and inhibitors of coagulation.

Use of Freeze-Dried Platelets as a Diagnostic Tool to Identify Specific Coagulation Factor Defects With the realization that freeze-dried platelets can be used to identify defects in intrinsic coagulation factors in a plasma based system, the ability of freeze-dried platelets to be used as a diagnostic tool to pinpoint the same kind of defects in a whole blood system was tested. The ability to do this would distinguish freeze-dried platelet-base diagnostics from other commercially available assays (e.g., aPTT, PT, ELISA, PCR etc.), where whole blood has to be processed to extract plasma, serum, or individual blood components to quantitatively determine the specific defects. For ease of reference, FIG. 24 depicts an overview of the blood coagulation system and blood coagulation inhibitors.

Figure 25:
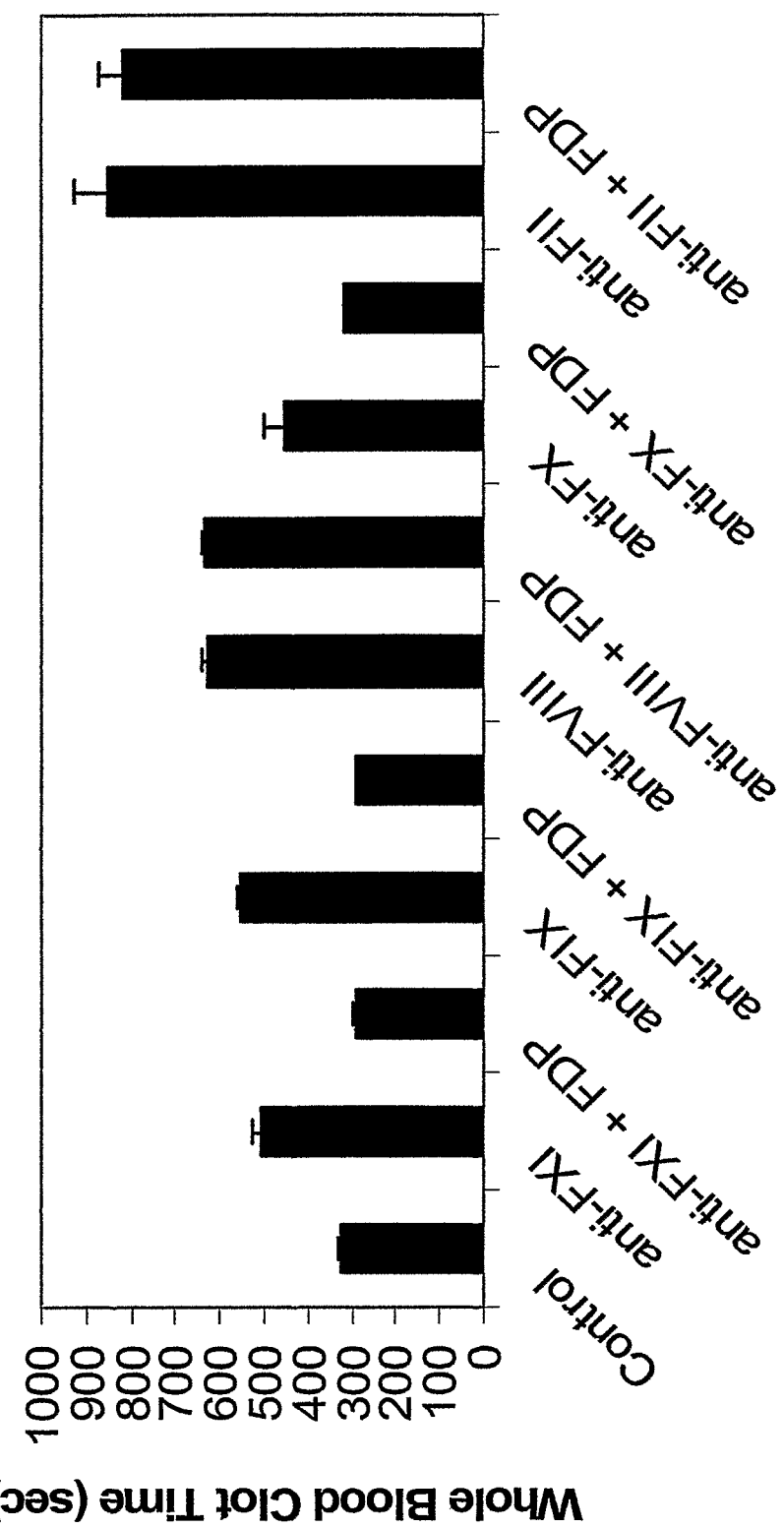
FIG. 25 depicts results of assays distinguishing coagulation protein defects in whole blood.

FIG. 25 depicts the effect of freeze-dried platelets on the clotting ability of blood samples having a known defect in a blood clotting component. The data shown in the Figure was obtained as follows: clot time as determined for a mixture containing 400 ul of ACD whole blood (either incubated with various antibodies targeted against specific coagulation factors or with anti-coagulation drugs that are currently used in health care facilities), 25 ul of 0.2 M $CaCl_2$, 25 ul saline, and 50 ul of various concentrations of reconstituted (rehydrated) freeze-dried platelets.

As can be seen from the Figure, the results of the whole blood assays agree with those of the plasma based assays. Freeze-dried platelets were able to reduce clotting times for defects in factors IX, X, and XI, but not factor VIII. This result indicates that freeze-dried platelets can be used in conjunction with both plasma and whole blood to identify defects in factors IX, X, and XI, and distinguish those defects from those of factor VIII. One advantage of this is that freeze-dried platelets can work well with whole blood, thus avoiding the complication of processing plasmas.

This Example demonstrates that the reaction profiles of freeze-dried platelets are virtually the same as that of the plasma-based system when specific antibodies are added to the whole blood. Furthermore, when whole blood was treated with various anti-coagulant drugs, it was found that freeze-dried platelets are also sensitive to these anticoagulants with different kinetics and reaction profiles (see below).

Thus, it has been found that the use of freeze-dried platelets has several distinctive advantages, including:

freeze-dried platelets can be used as a stand alone reagent to identity defects in factors involved in the intrinsic pathway;

freeze-dried platelets can be used with any existing clinical equipment known to be suitable for use with fresh platelets;

freeze-dried platelets can be used in conjunction with exiting diagnostic kits as calibrate reagent; and freeze-dried platelets can be used with whole blood or plasma to identity defects in factors involved in the intrinsic pathway.

Example 28

Freeze-Dried Platelets Show Distinctive Reaction Profiles with Whole Blood

With the knowledge that freeze-dried platelets can be used to identify specific defects in blood clotting systems, the ability of such platelets to identify the presence or effect of various anti-coagulants was tested. Freshly drawn blood in ACD was incubated with the indicated amount of inhibitors. The freeze-dried platelets, at various concentrations, were added and incubated at room temperature for 30 seconds. Blood was then recalcified with 10 mM $CaCl_2$ and clot time was determined.

Figure 26:
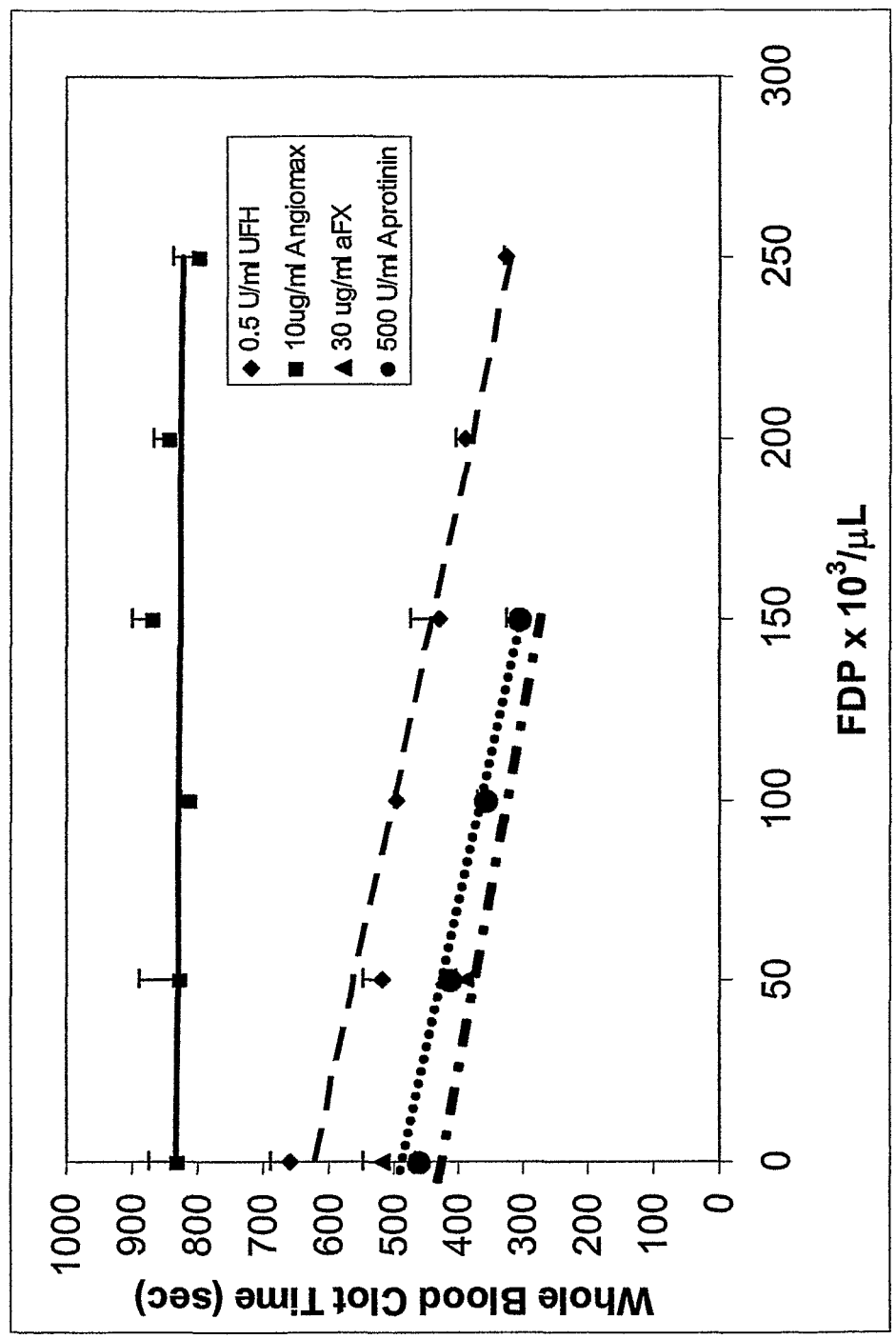
FIG. 26 depicts specific reaction of freeze-dried platelets of the invention with anti-coagulants.

As can be seen from FIG. 26, freeze-dried platelets can be used to identify the presence and/or effect of anti-coagulants in whole blood. Because the freeze-dried platelets react to specific anti-coagulants with distinctive reaction profiles, they can be used not only to detect the presence of the anti-coagulant, but to determine how much of the anti-coagulant is present in the blood. In this way, the anti-coagulant can be monitored in the blood, for example, to ensure that the proper dose is being taken. This is particularly helpful for cardiopulmonary by pass (CBP) patients who are on heparin therapy. Blood from these patients can be monitored at the bedside to determine the levels of heparin in the blood and when it would be safe for surgery.

Example 29

Use of Freeze-Dried Platelets to Monitor Vitamin-K Dependent Clotting Factors Many clotting factors in the clotting cascade are vitamin-K dependent and bind to negatively charged phospholipids on cell membranes. In addition, the Annexin-V marker is a marker for platelet pro-coagulant activity, as it binds to negatively charged phospholipids in a $Ca^{2+}$-dependent manner similar to vitamin-K dependent proteins. To analyze binding of these proteins to freeze-dried platelets, the following experiments were performed on a Becton Dickenson FACS caliber instrument using log-log settings. Platelets were characterized by their representative forward and side scatter light profiles (performed using gel filtered platelets) and/or by the binding of the Fluorescence-labeled proteins. Platelets were diluted to ~50,000 per ul in HBMT in separate tubes and Fluorescence-labeled proteins were added at saturation for 30 minutes at ambient temperature. Samples were diluted with 2 ml HMBT and 10,000 individual events collected. The fluorescence histogram and percentage of positive cells were recorded, and this represented the platelet population that bound to the fluorescence labeled protein.

Figure 27:
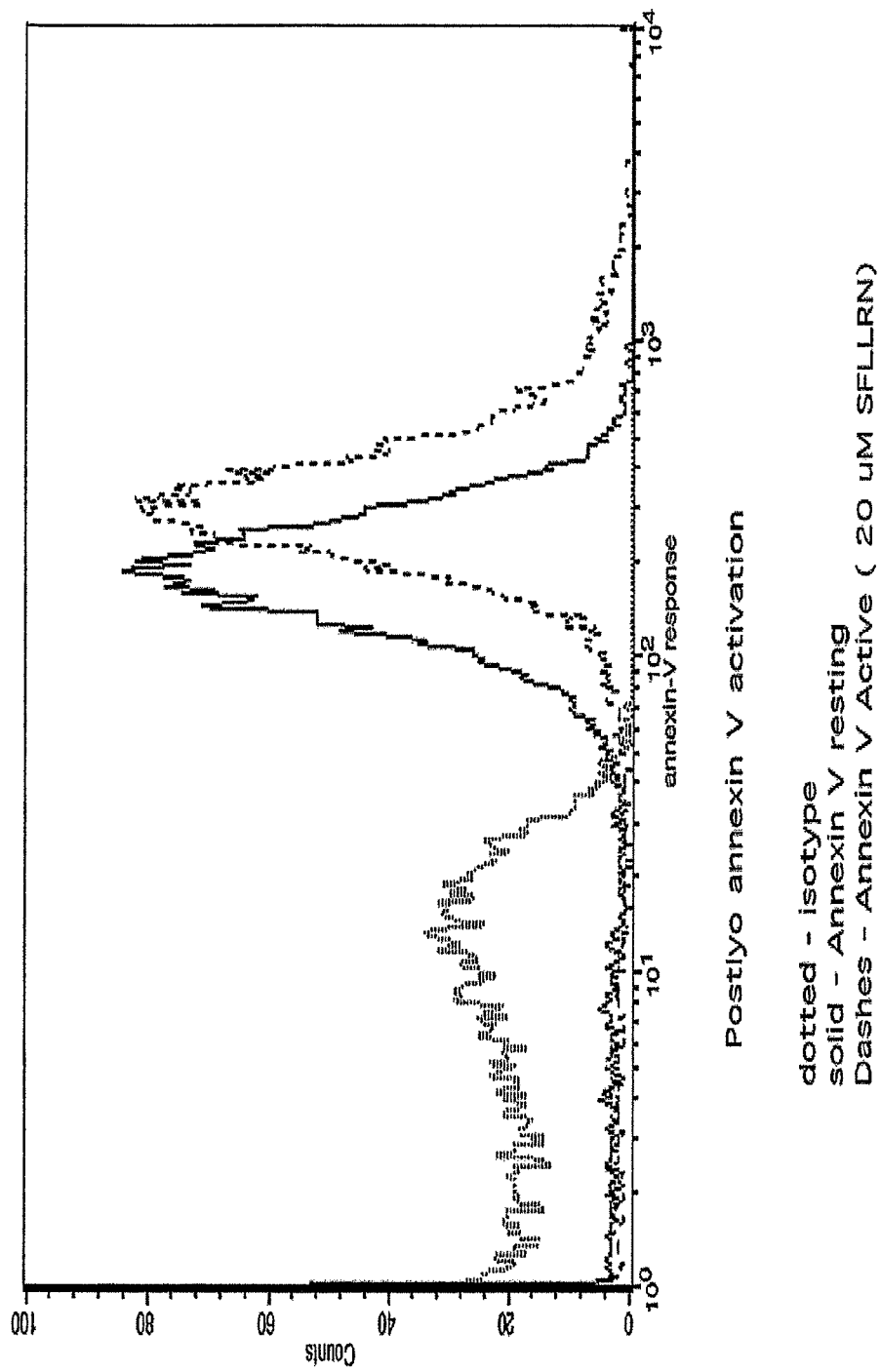
FIG. 27 shows that freeze-dried platelets are activated with ionophores, which expose additional binding sites for FITC-Annexin V binding to freeze-dried platelets.
Figure 28:
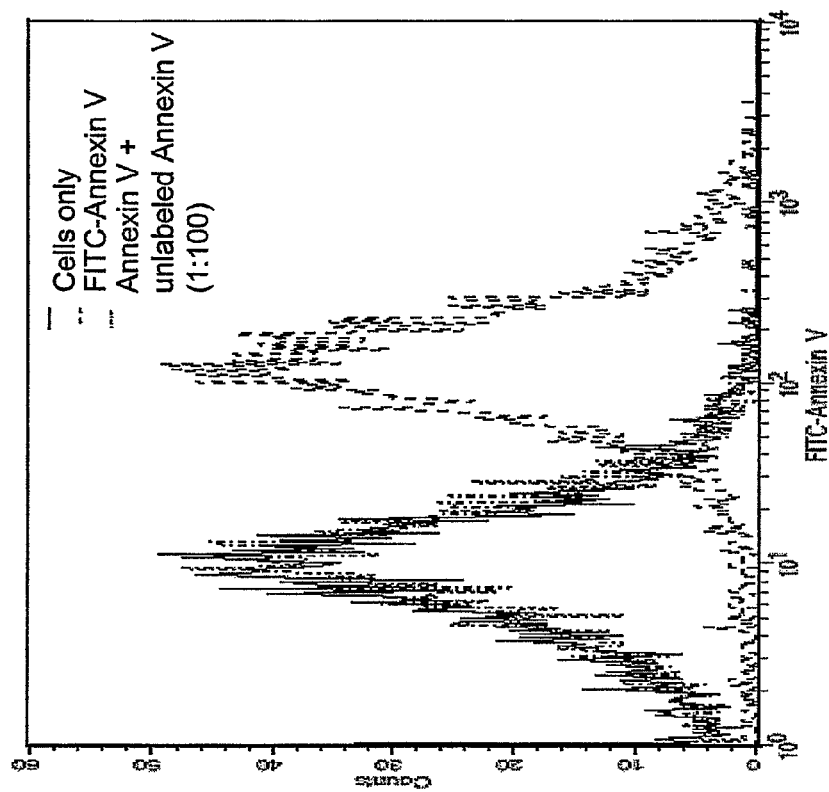
FIG. 28 shows that freeze-dried platelets binding to 50 nM FITC-Annexin V can be competed with 100 fold excess of unlabled Annexin V.

As can be seen from FIG. 27, freeze-dried platelets bind to 25 mM of FITC-labeled Annexin-V (denoted Annexin V resting). Upon addition of with 20 uM of the TRAP peptide (SFLLRN), freeze-dried platelets exposed additional negatively charged phospholipids, resulting in additional Annexin V binding (denoted Annexin V Active). To ascertain that the binding of FITC-Annexin V to resting freeze-dried platelets is specific, 100-fold excess of unlabeled Annexin V was added. As can be seen from FIG. 28, the binding of FITC-Annexin V can be competed off by unlabeled Annexin V, suggesting that the negatively charged surface of the freeze-dried platelets is structured with defined binding sites.

Figure 29:
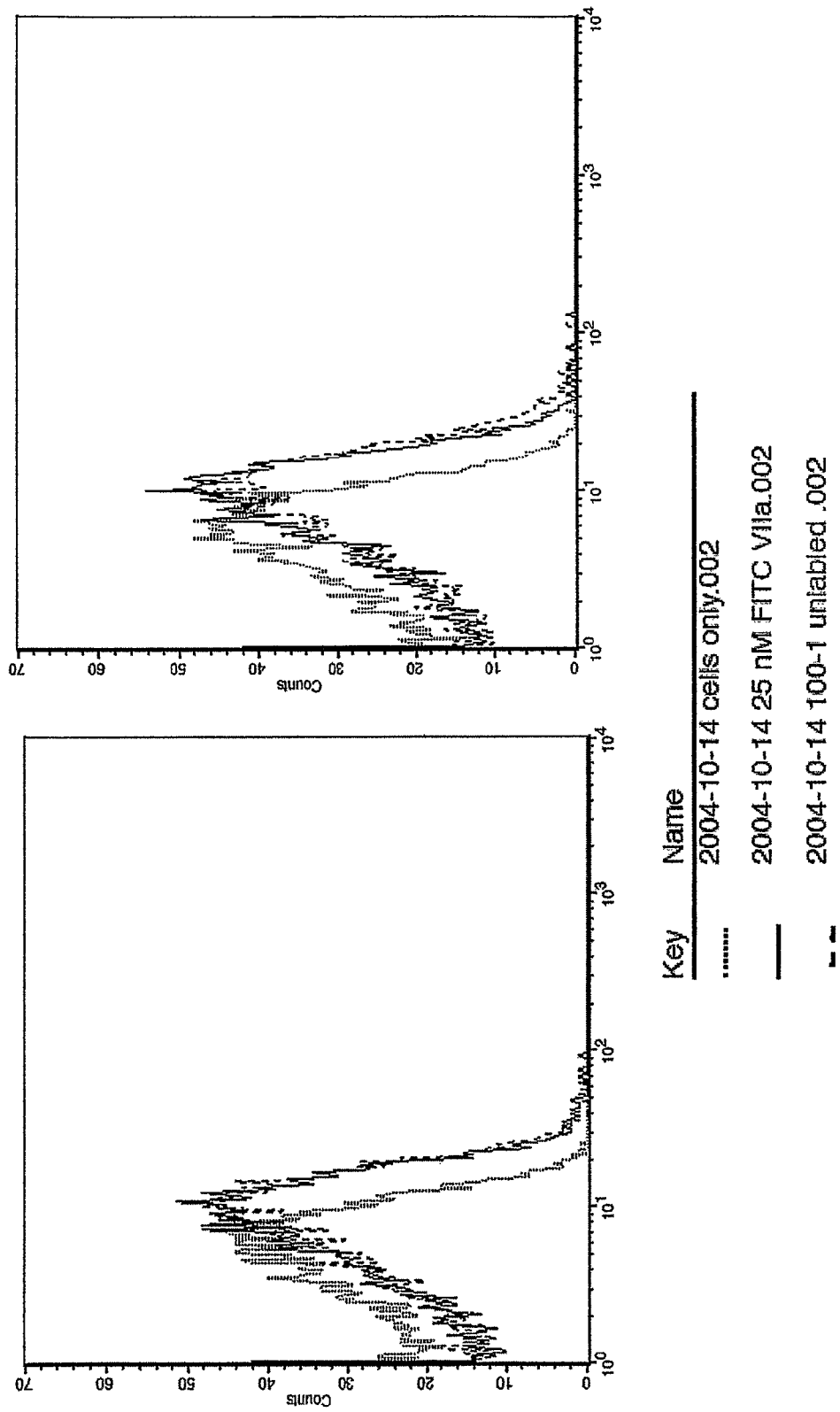
FIG. 29 shows that 25 nM of labeled FVIIa failed to bind to both unactivated and ionophore activated fresh platelets.
Figure 30:
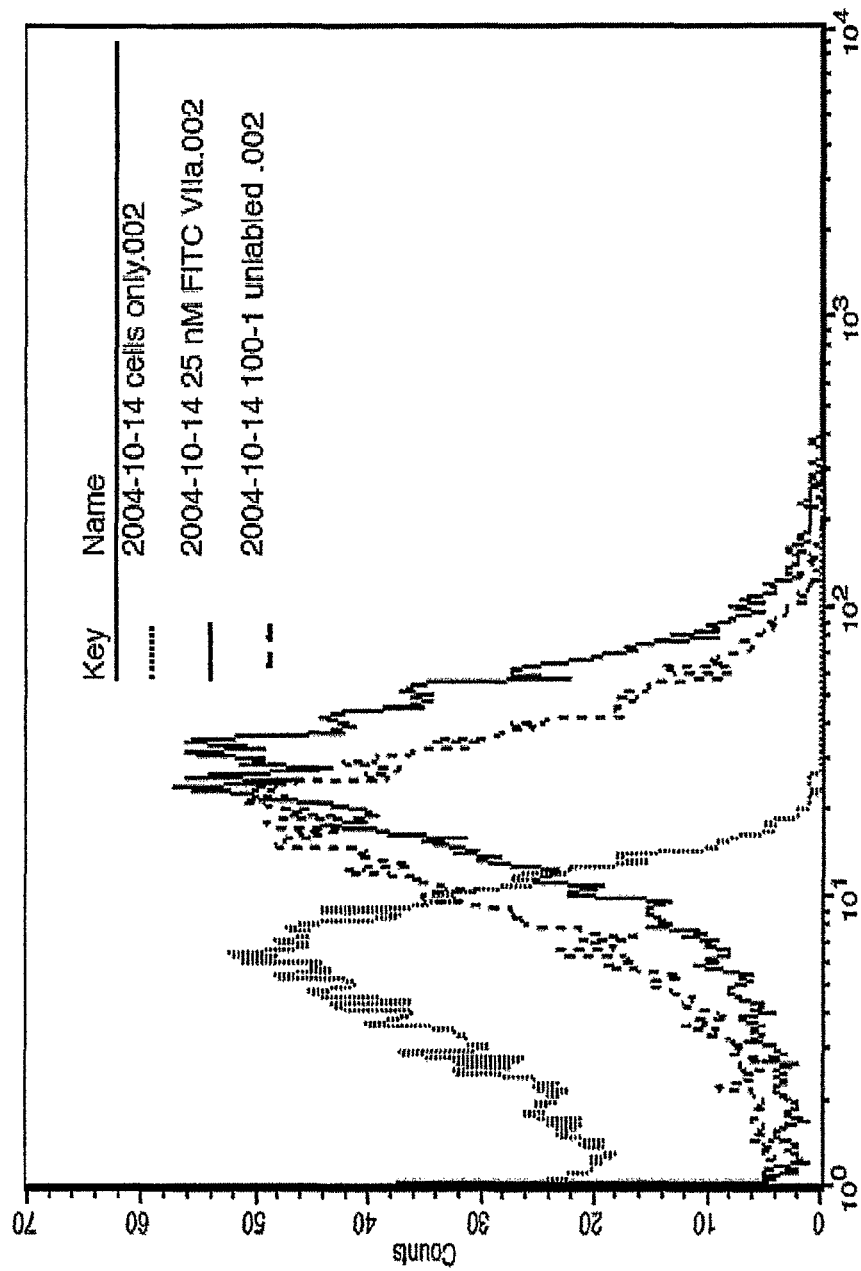
FIG. 30 depicts direct binding of 25 nM of FVIIa to freeze-dried platelets and shows that the binding can be competed off using 2500 nM unlabeled FVIIa.

To be more specific, vitamin K dependent proteins were used in the binding assay. When FITC-labeled PPACK-FVIIa (active site inhibited FVIIa) was tested for binding, it was found that FVIIa failed to bind to fresh unactivated platelets as well as fresh activated platelets at a concentration of 25 nM (FIG. 29). However, when freeze-dried platelets were used, FITC-FVIIa showed specific binding at 25 nM and this binding can be competed with unlabeled FVIIa (FIG. 30).

Figure 31:
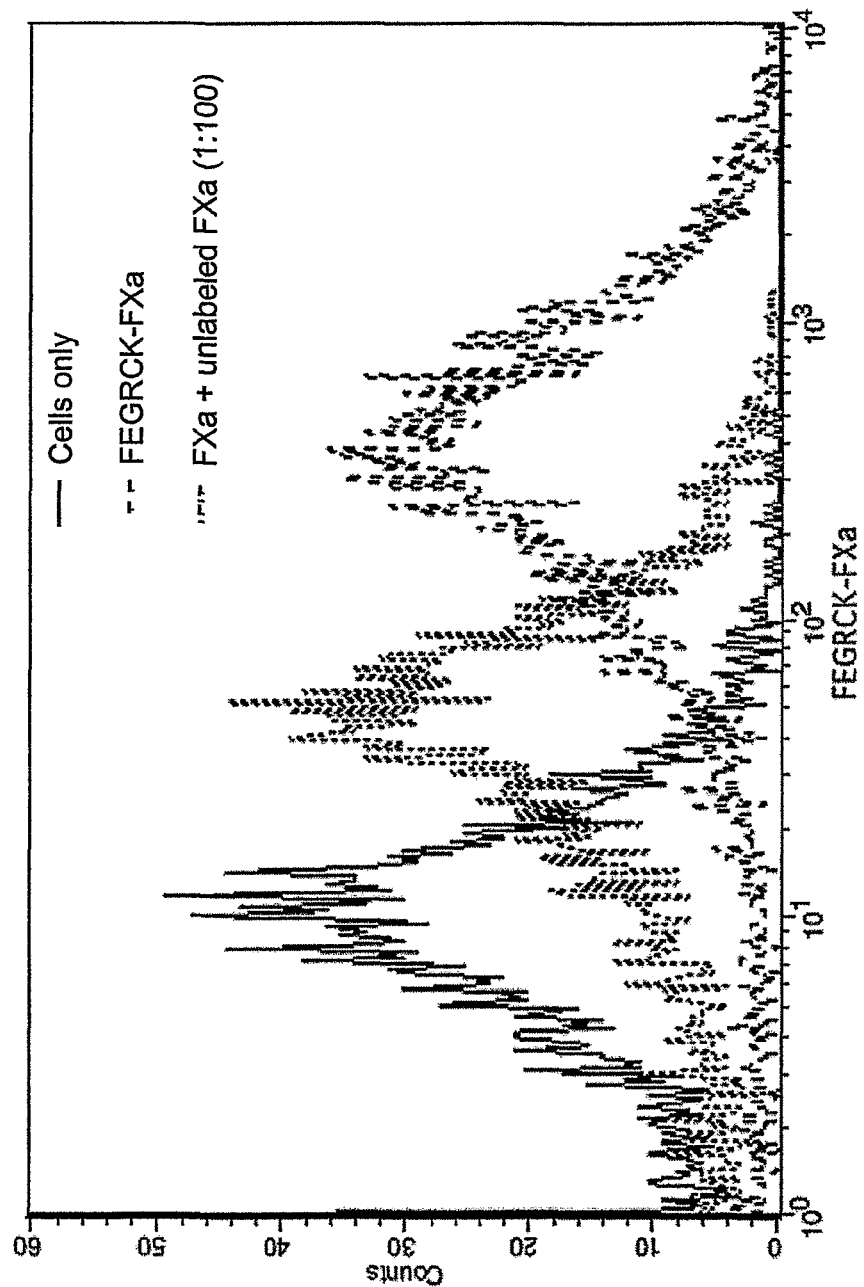
FIG. 31 depicts direct binding of 100 nM of FXa to freeze-dried platelets and shows that the binding can be competed off using 10000 nM unlabeled Fxa.

The binding of FITC-labeled EGR-FXa (active sited inhibited FXa) to freeze-dried platelets was also investigated. As can be seen in FIG. 31, the binding of FXa to freeze-dried platelets was specific since it can be competed off by 100-fold excess unlabeled FXa.

Thus, an advantage of using freeze-dried platelets to monitor vitamin K dependent coagulation factors functionality or concentration in whole blood or plasma is evident from these experiments. These coagulation factors bind to the surface to of the freeze dried platelets in a specific manner. Furthermore, this specific binding to the surface of the freeze-dried platelets can be modified. For example, the surface of freeze-dried platelets can be coupled to an agent (luminescence or otherwise) that is specific to each of the Vitamin K dependent factors. The signal (luminescence or otherwise) can be interpreted to pinpoint the identity of the missing factor(s) or factor(s) that is or are under the influence of anticoagulation medication.

Example 30

Use of Freeze-Dried Platelets as Diagnostic Reagents to Identify Platelet Defects Other experiments showed that the freeze-dried platelets of the invention have similar physical and functional characteristics as fresh platelets. To better characterize the physical characteristics, freeze-dried platelets were tested for their response to various agonists that are known to have an inhibitory action on coagulation of fresh platelets.

The experiments in this Example were performed as follows: fresh platelets and/or freeze-dried platelets were diluted to a final concentration of 250,000 platelets per ul in HEPES-Tyrodes Buffer containing 0.3% bovine serum albumin (BSA). Various agonists were added to each composition, as outlined below. 400 ul of the composition was placed in aggregometry cuvettes, and aggregation of the platelets followed over time.

Alpha-FIIa: 0.05-1 U/ml;
Gamma-FII: 0.03 ug/ml;
A23187: 10 mM;
Thrombin Receptor Activating Peptide (TRAP): SFLLRN: 10 mM;
Risto +: 1 mg/ml (20% Autologous Citrated Plasma);
Risto −: 1 mg/ml;
Collagen (Chronolog): 10 ug/ml;
Epinephrine: 300 uM;
Arachidonic Acid: 0.5 mg/ml;
ADP: 20 uM;
Control: No Agonist.

Figure 32:
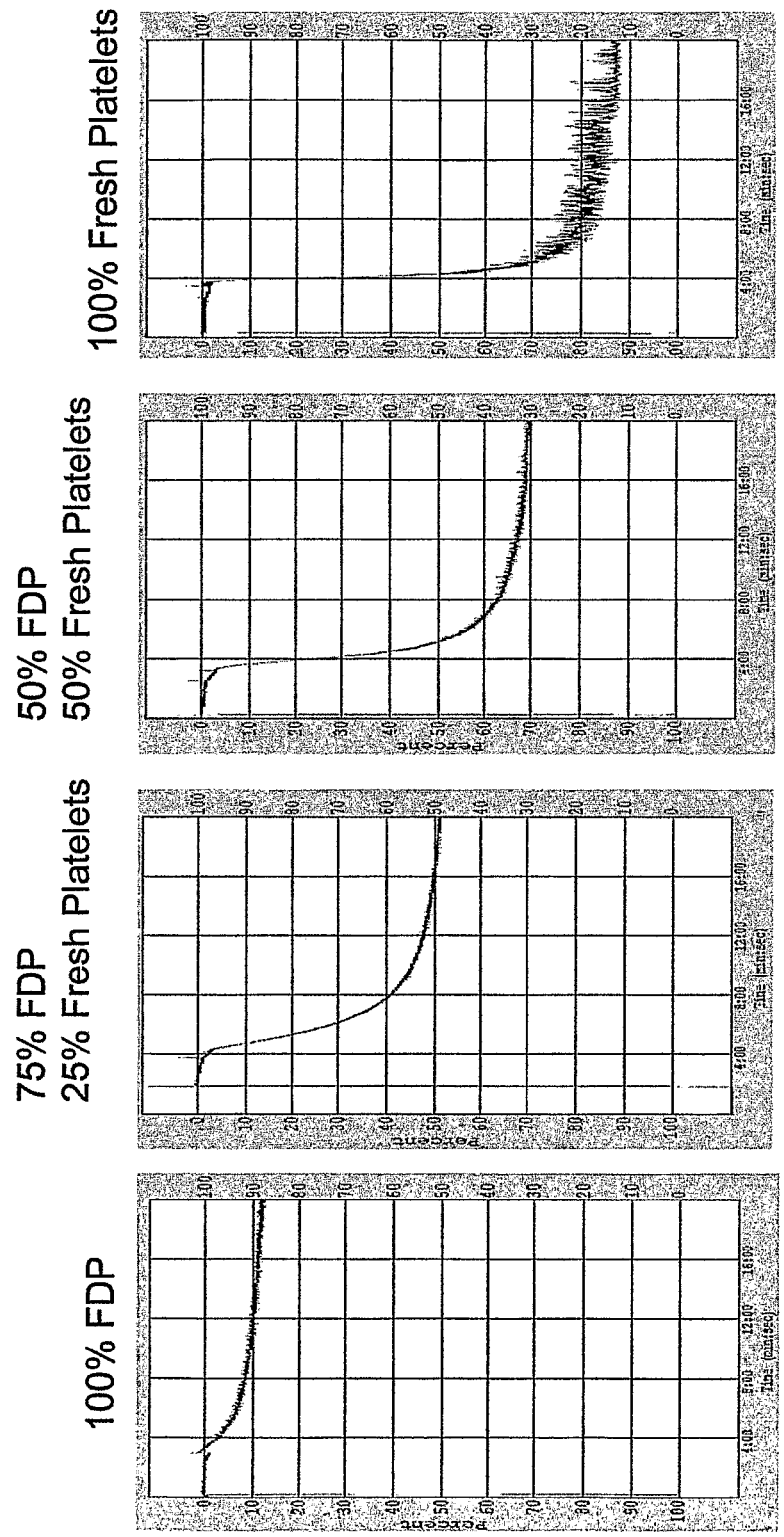
FIG. 32 depicts the effects on collagen-mediated aggregation of freeze-dried platelets, fresh platelets, and combinations of the two.

The results of the assays using collagen are presented in FIG. 32. Panel A depicts the percent aggregation when 100% freeze-dried platelets were used. The panel shows a low amount of aggregation (about 10%), indicating that the freeze-dried platelets are only partially sensitive to collagen. In contrast, Panel D shows the effect of collagen on fresh washed platelets. In Panel D, almost 90% aggregation is seen over the same time period that resulted in a little over 10% aggregation of freeze-dried platelets. As can be seen from Panels C and D, mixtures of varying amounts of freeze-dried platelets and fresh platelets gives intermediate levels of aggregation, the amount being dependent on the relative amounts of freeze-dried platelets and fresh platelets added.

In a second set of experiments designed to determine the effect of freeze-dried platelets on the aggregating function of fresh platelets, varying amounts of freeze-dried platelets (rehydrated platelets, or RH) were combined with varying amounts of fresh platelets. The reconstituted platelets were mixed with fresh platelets at the concentrations indicated. To each of these, 10 ug/ml (400 ul platelets+4 ul of 200 mM MgCl (2 mM)+4 ul of 1 mg/ml Collagen (10 ug/ml)) were added to the mixture. After 5 minutes at room temperature, platelets were counted using a standard Complete Blood Count machine (ACT 10 from Beckman coulter).

Figure 33:
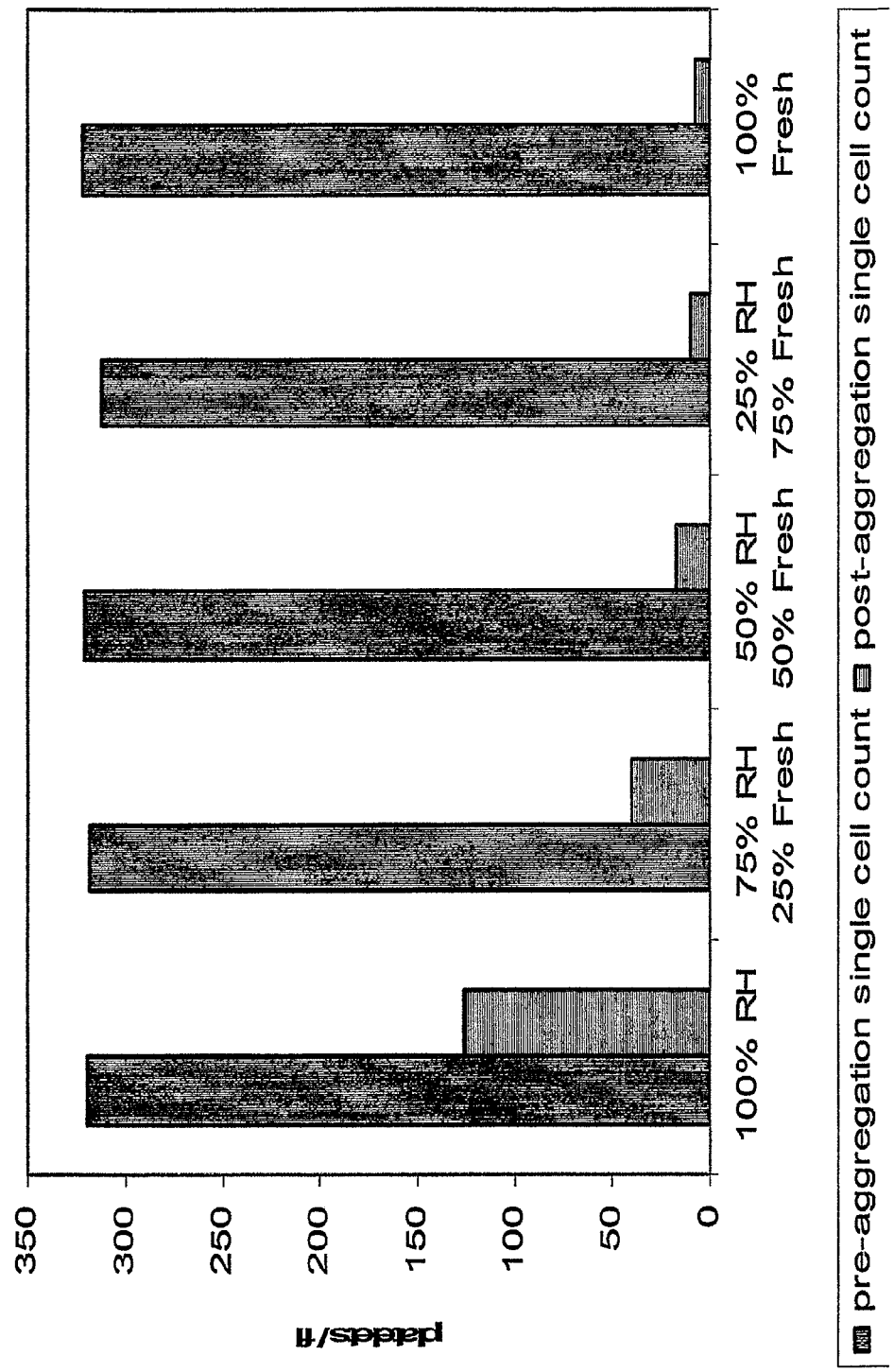
FIG. 33 depicts the effects of collagen-mediated aggregation as judged by single cell count of freeze-dried platelets, fresh platelets, and combinations of the two.

As can be seen from FIG. 33, various mixtures of freeze-dried platelets and fresh platelets have intermediate aggregating characteristics, depending on the relative amounts of each present in the mixture.

Figure 34:
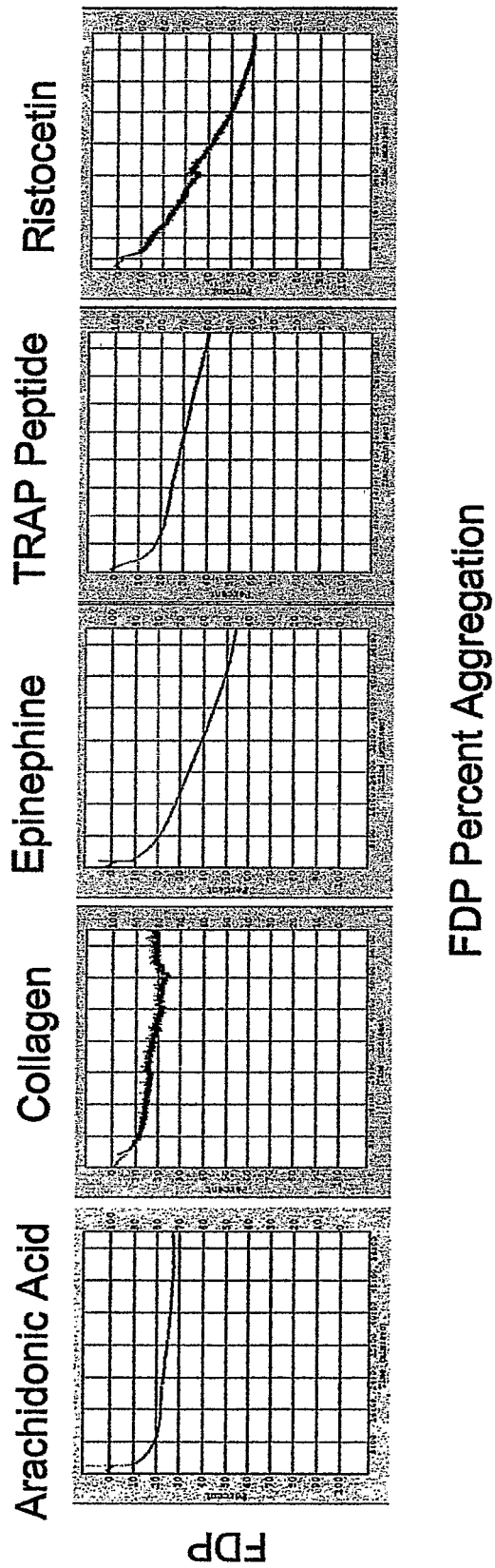
FIG. 34 depicts the effect on freeze-dried platelets when exposed to arachidonic acid, collagen, epinephrine, thrombin receptor activating peptide (TRAP), and ristocetin mediated aggregation of freeze-dried platelets. The figure also depicts the percent aggregation of freeze-dried platelets as judged by single cell count.

Furthermore, it was also seen that freeze-dried platelets aggregated in response to Arachidonic Acid, Collagen, Epinephrine, thrombin receptor activating peptide (TRAP) and Ristocetin, with aggregation percentage determined to be 77, 83, 86, 93, and 97 respectively (FIG. 34).

The results of FIGS. 32, 33, and 34 indicate that freeze-dried platelets contain at least partially functional receptors that are responsive to all agonist listed above, and have low, but detectable levels of self-aggregation. In a reaction where freeze-dried platelets were mixed with fresh platelets, we demonstrated that the mixture was able to aggregate synergistically in a dose dependant manner. Thus, the use of freeze-dried platelets as a platelet specific diagnostic tool offers several advantages in its various embodiments:

a unique technology to perform such assays—platelets that are fixed with formaldehyde agglutinate do not aggregate, whereas freeze-dried platelets according to the invention are;

freeze-dried platelets preserve relevant surface markers that can be used to monitor platelet function defects, such as Glanzman's thrombasthenia, Bernard-Soulier syndrome, Gray platelet syndrome, Quebec Platelet disorder, Hermansky-Pudlak Syndrome, Chediak-Higashi syndrome, Wiskott-Aldrich syndrome, release defects, vWF disorder, Afibrinogenenia, Scott syndrome, and other congenital disorders;

a patient's own platelets can be freeze-dried and used as a control reagent to monitor the patient's own platelet function during the course of a therapy regimen;

pooled platelets can be freeze-dried and used as global platelet reagent for the same purpose; and compositions of the invention can be stand-alone products, which can be used on any existing equipment that is suitable for analysis of platelets.

Example 31

Induction of Pseudo-Hemophilia C and Treatment with Platelets

Figure 35A:
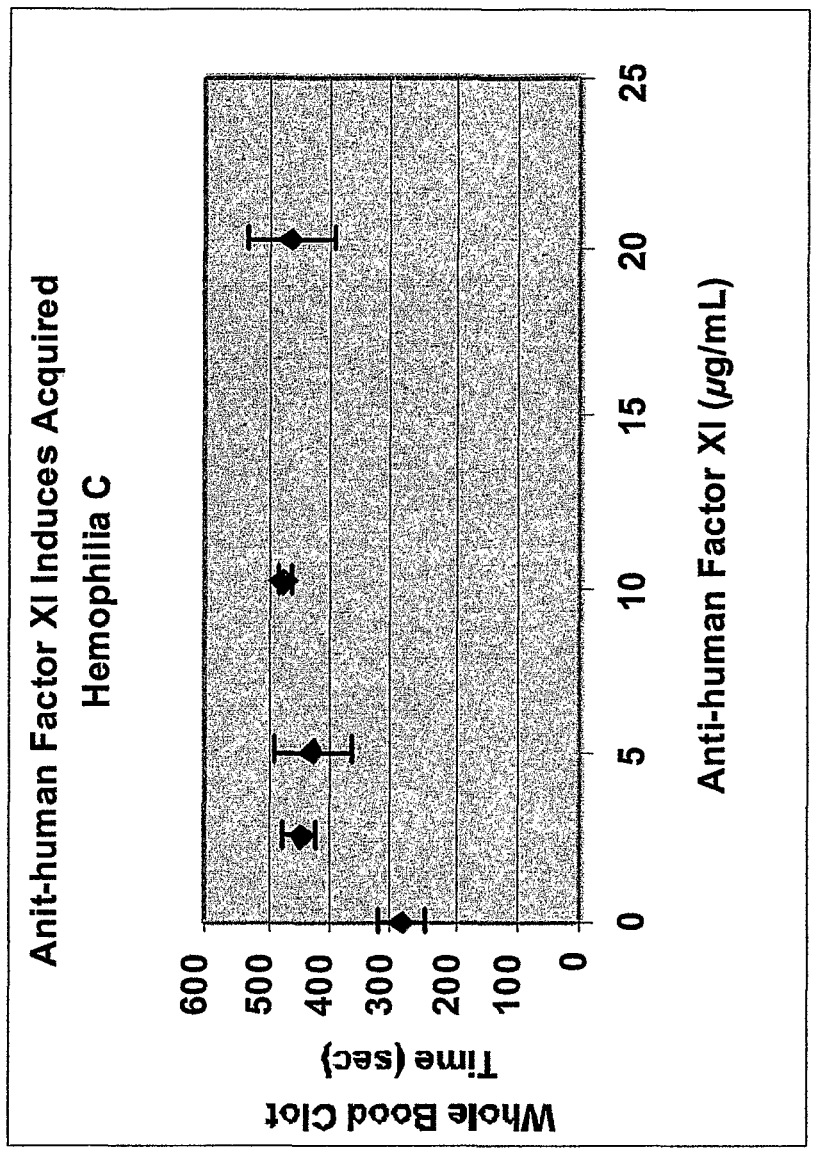
FIG. 35A shows that a monoclonal antibody against Factor XI induces a pseudo-acquired Hemophilia C by increasing clotting time from about 300 seconds to almost 500 seconds.
Figure 35B:
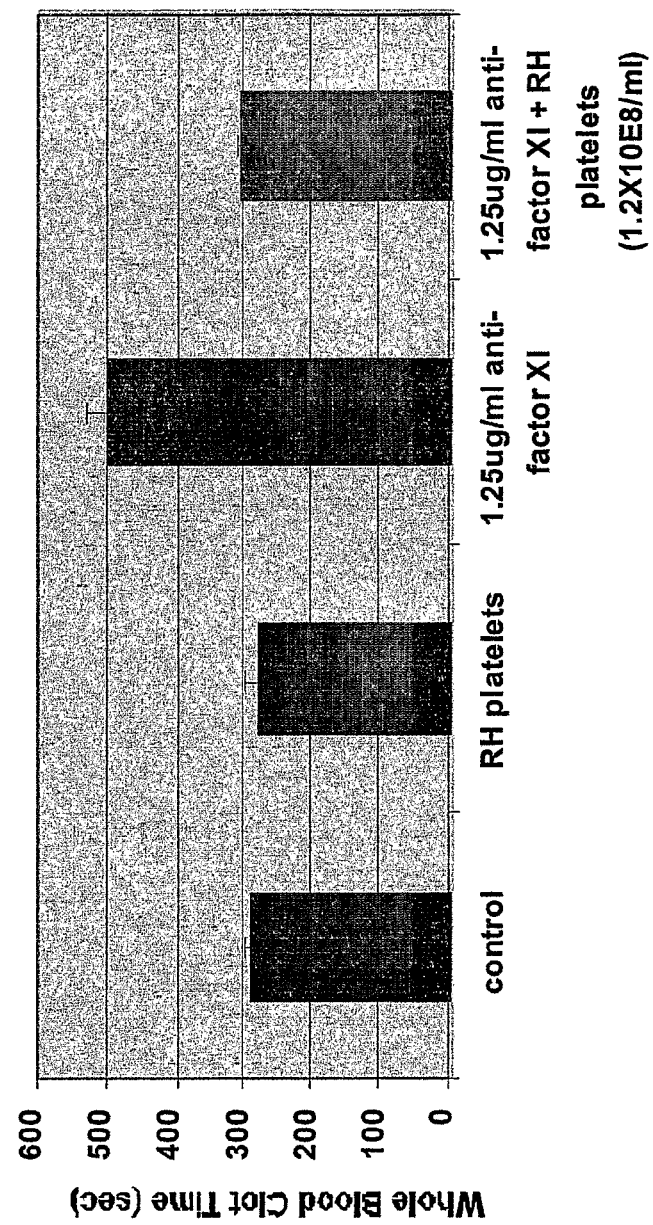
FIG. 35B shows that a composition of the invention comprising rehydrated platelet derivatives shortens clot times in whole blood models of Acquired Hemophilia C (Inhibitor to Factor XI).

A model for treatment of Hemophilia C was developed to determine if the platelets of the invention could treat this disorder. To do so, blood was collected into 1/10 volume of 3.8% sodium citrate, pooled, and separated into 1 ml aliquots. Monoclonal antibody to Factor XI (Hematologic Technologies, Inc, Essex Junction Vt.) or saline control was added to between 0 and 30 ug/ml and incubated for 15 minutes at ambient temperatures. 400 ul of the blood was transferred to tubes containing 25 ul of 0.2 M Calcium chloride (10 mM Final) and 75 ul of buffer control or rehydrated platelets to initiate clotting. The tubes were instantly placed in an Actalyke-activated clotting time machine (Helena Labs, Beaumont, Tex.) and the clotting times automatically recorded. The data presented in FIGS. 35A and 35B show that, in an induced model of Hemophilia C, platelets of the invention can overcome the inhibition or loss of Factor XI and return clotting times to the normal range.

Example 32

Induction of Pseudo-Hemophilia B and Treatment with Platelets

Figure 36:
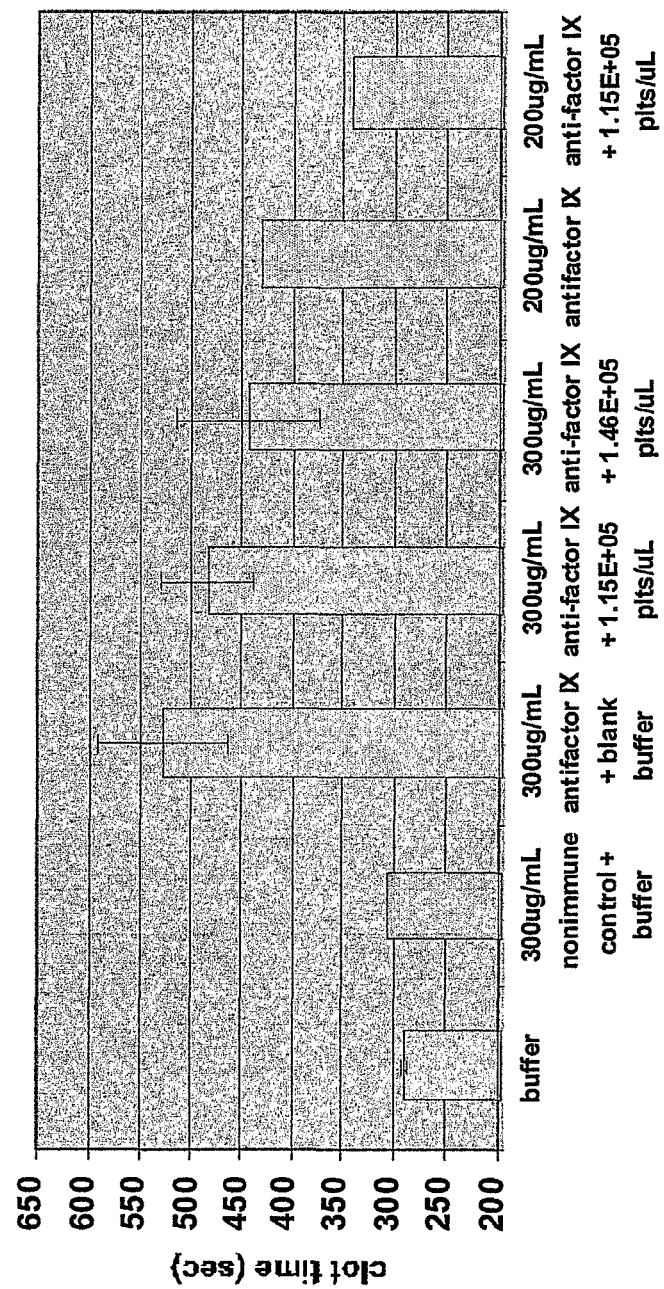
FIG. 36 shows that a monoclonal antibody to Factor IX induces pseudo-Acquired Hemophilia B and that rehydrated platelet derivatives shorten clot times in whole blood models of Acquired Hemophilia B (Inhibitor to Factor IX).

A model for treatment of Hemophilia B was developed to determine if the platelets of the invention could treat this disorder. Experiments were performed as described under Example 31, except sheep polyclonal antibody to Factor 1× or a non-immune sheep antibody control were utilized. The data presented in FIG. 36 show that, in an induced model of Hemophilia B, platelets of the invention can overcome the inhibition of Factor IX and return clotting times to the normal range.

Example 33

Induction of Acquired Hemophilia with Inhibitors and Treatment with Platelets

Figure 37:
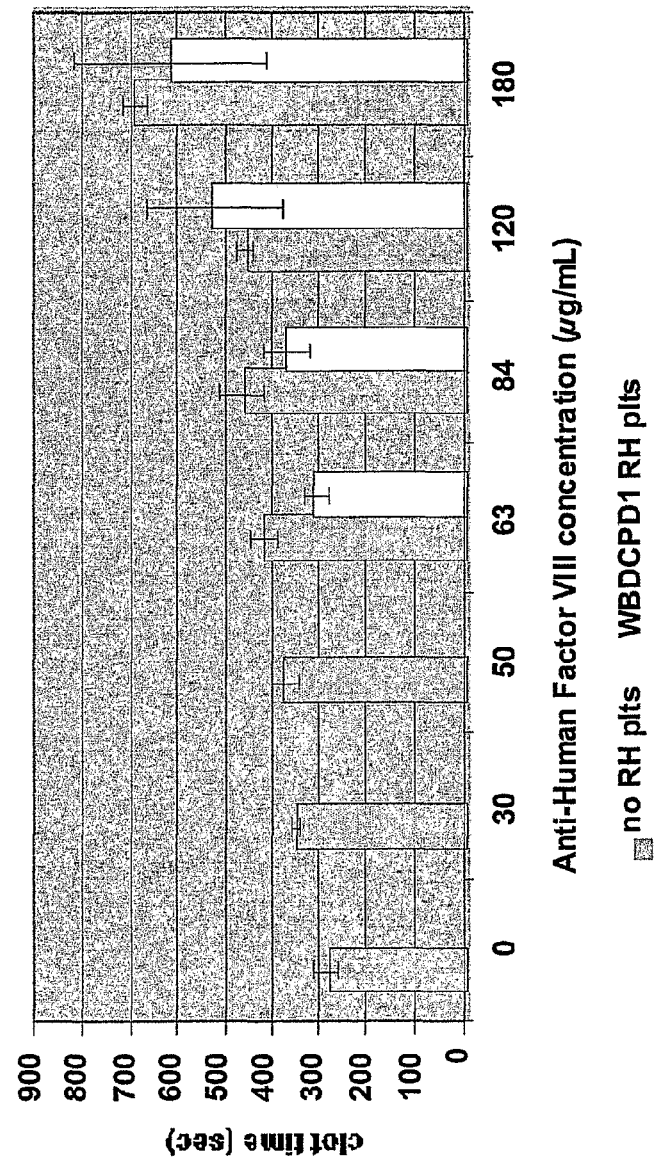
FIG. 37 shows that a monoclonal antibody to Factor VIII induces pseudo-Acquired Hemophilia A and that rehydrated platelet derivatives shorten clot times in whole blood models of Acquired Hemophilia A (Inhibitor to Factor VIII).

A model for treatment of Acquired Hemophilia with Inhibitors was developed to determine if the platelets of the invention could treat this disorder. Experiments were performed as described under Example 31, except sheep polyclonal antibody to Factor vm or a non-immune sheep antibody control were utilized. The data presented in FIG. 37 show that, in an induced model of Acquired Hemophilia with Inhibitors, platelets of the invention can overcome the inhibition of Factor VIII and return clotting times to the normal range.

Example 34

Treatment of Hemophiliac Blood With Platelets

Figure 38:
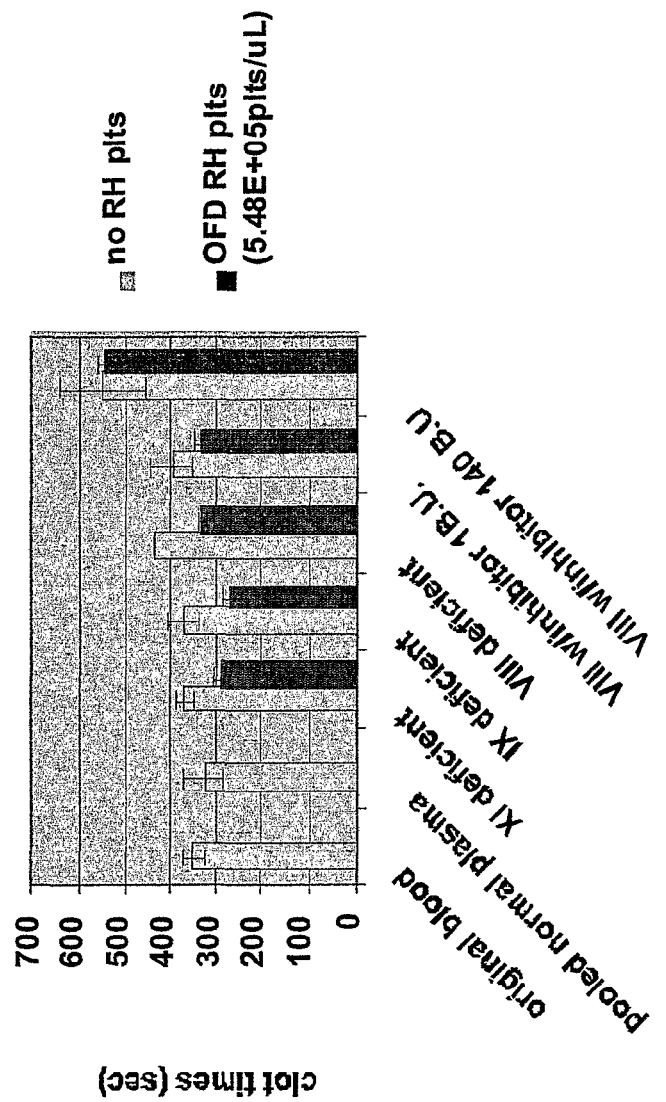
FIG. 38 shows that rehydrated platelet derivatives shorten clot times of reconstituted whole blood derived from bona fide hemophilia plasma.

To test the platelets of the invention on bona fide hemophilia blood, samples of blood from persons known to be affected by the various forms of hemophilia were tested, along with normal blood and plasma. Plasma from patients having Congenital Hemophilia A, B, or C, or low titer (I Bethesda Unit) and high titer (140 Bethesda Units), and control pooled normal plasma were obtained form George King Biomedical (Overland Park, Kans.). Citrated blood from a normal Type O donor was freshly obtained, divided into 2 ml aliquots, and centrifuged at 2000×g for 15 minutes to pellet the cells. The plasma was removed and the spun cells reconstituted with an equivalent volume of autologous plasmas obtained above to 45% hematocrit. Such reconstituted bloods (400 ul) were placed in the clotting tubes and clotting initiated by re-calcification in the presence or absence of rehydrated platelet derivatives, as described above. The data presented in FIG. 38 show that platelets of the invention can overcome the loss of Factors XI, IX, and VIII, and inhibition of Factor VIII by an in vivo inhibitor, in hemophiliac blood, and return clotting times to the normal range. The data thus confirm the results obtained in the model systems presented in Examples 31-33, and validates the models used in those Examples.

Example 35

Induction of Clotting Deficiency With Aprotinin and Treatment with Platelets

Figure 39A:
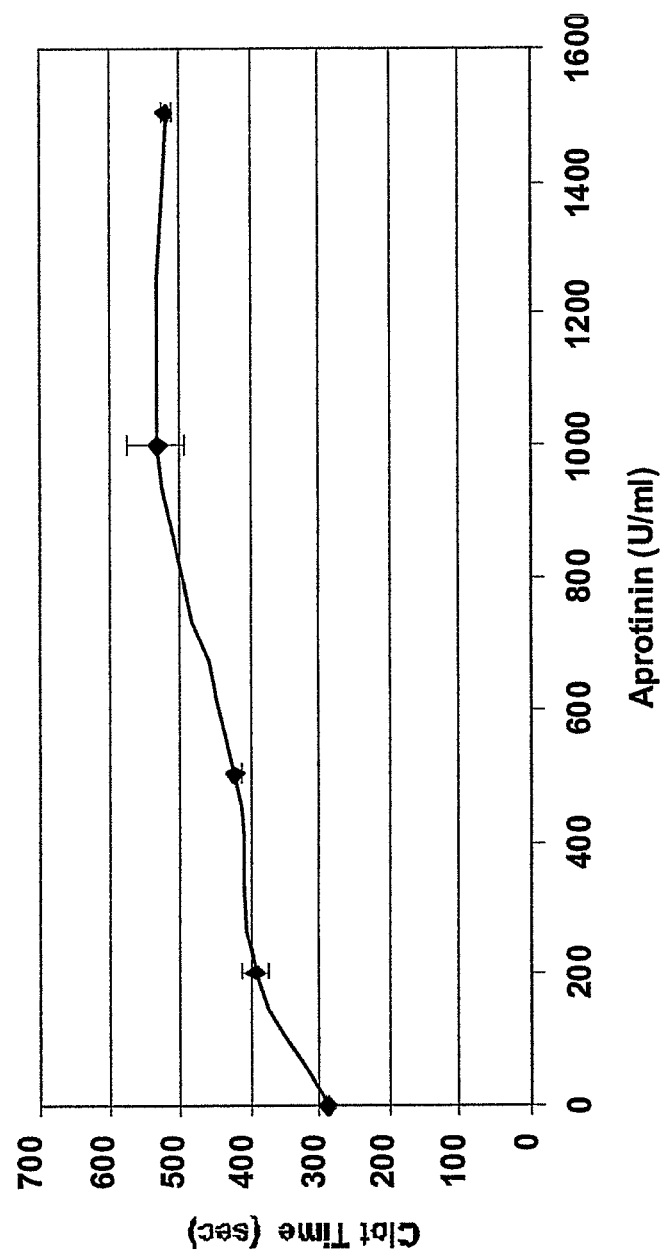
FIG. 39A shows Aprotinin inhibition as a model of drug induced coagulopathy.
Figure 39B:
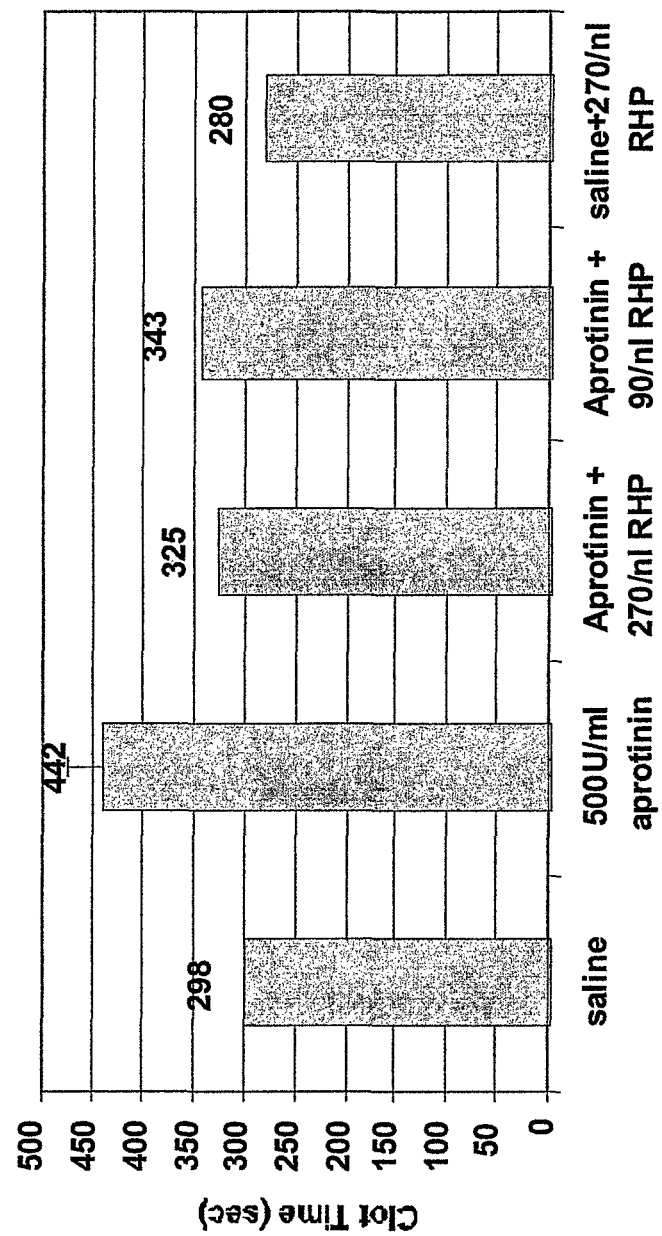
FIG. 39B shows that the inhibition by Aprotinin can be reversed by rehydrated platelet derivatives (RHP).

A model for treatment of delayed clotting due to treatment with anti-clotting agents was developed to determine if the platelets of the invention could treat this effect. Normal citrated blood was incubated with 0-2000 U/ml Aprotinin (Calbiochem) or saline control, then 400 ul were placed in the clotting tubes and clotting initiated by re-calcification in the presence or absence of rehydrated platelets, as described above. The data presented in FIGS. 39A and 39B show that, in an induced model of delayed blood clotting due to treatment with anticoagulants, platelets of the invention can overcome the effects of the anti-clotting factor and return clotting times to the normal range.

Example 36

Figure 40A:
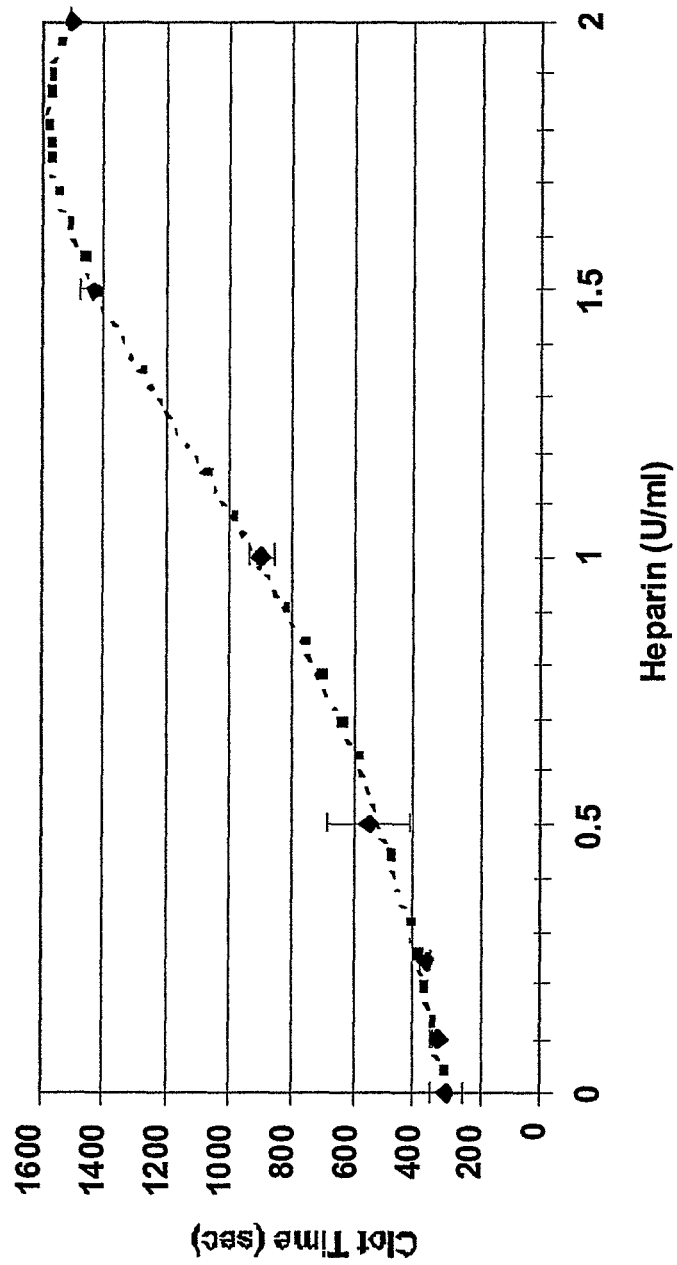
FIG. 40A shows heparin inhibition as a model of drug induced coagulopathy.
Figure 40B:
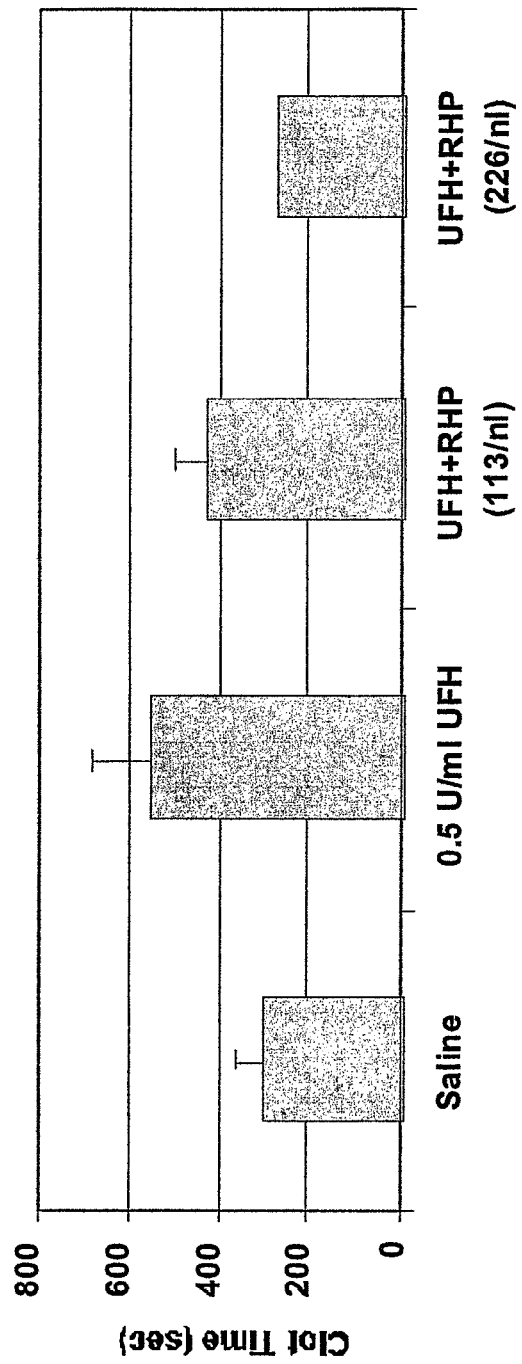
FIG. 40B shows that the inhibition by heparin can be reversed by rehydrated platelet derivatives.

Induction of Clotting Deficiency (Drug Induced Coagulopathy) With Heparin and Treatment with Platelets A second model for treatment of delayed clotting due to treatment with anti-clotting agents was developed to determine if the platelets of the invention could treat this effect. In this model, whole blood was treated with heparin to delay or inhibit clotting. Experiments were performed as described for Example 35, except that unfractionated Lithium heparin was utilized instead of Aprotinin. The data presented in FIGS. 40A and 40B show that, in an induced model of delayed blood clotting due to treatment with anticoagulants, platelets of the invention can overcome the effects of the anti-clotting factor and return clotting times to the normal range.

Example 37

Effect of Platelets on Activity of Recombinant Factor VIIa

To determine the effect of platelets of the invention on the activity of known clotting agents that are used to treat hemophilia, recalcified whole blood was treated with a sub-pharmacologic concentration (5 nM) of recombinant Factor VIIa, either alone or in the presence of platelets of the invention. The results of the experiments are shown in FIG. 41. The test system employed was a whole blood recalcified clotting time assay performed on a standard Activated Clotting Time (ACT) machine using custom assay tubes devoid of any exogenous clot promoting agents, such as Kaolin, Celite, or Glass.

The data presented in FIG. 41A were generated as follows. Citrated blood from a normal donor was freshly obtained, divided into 2 ml aliquots, and centrifuged at 2000×g for 15 minutes to pellet the cells. The plasma was removed and the spun cells reconstituted with an equivalent volume of autologous plasma (PPP, no plts), autologous PRP (PRP), or PPP containing rehydrated platelet preparations from two independent lots (RH lot 1, RH lot 2). Final platelet count in all samples was 150,000/ul and 45% hematocrit. Such reconstituted bloods (400 ul) were placed in the clotting tubes and clotting initiated by re-calcification in the presence or absence of rehydrated platelet derivatives, as described above.

The data presented in FIGS. 41B and 41C were generated as follows. Rehydrated platelets were diluted to 50,000-100,000 per ul in Divalent Cation Free HEPES Tyrodes Buffer containing 0.35% bovine albumin and supplemented with either nothing, 1 mM $MgCl_2$, 2 mM $CaCl_2$, or both. 50 ul of diluted platelets were incubated alone or with 5 nM (sub-pharmacologic) or 25 nM (pharmacologic) FITC-PPACK-FVIIa for 30 minutes at ambient temperature, then washed with 2 ml of the same buffer, and analyzed by flow cytometry on log-log settings, and data obtained for the platelet only gate.

Figure 41A:
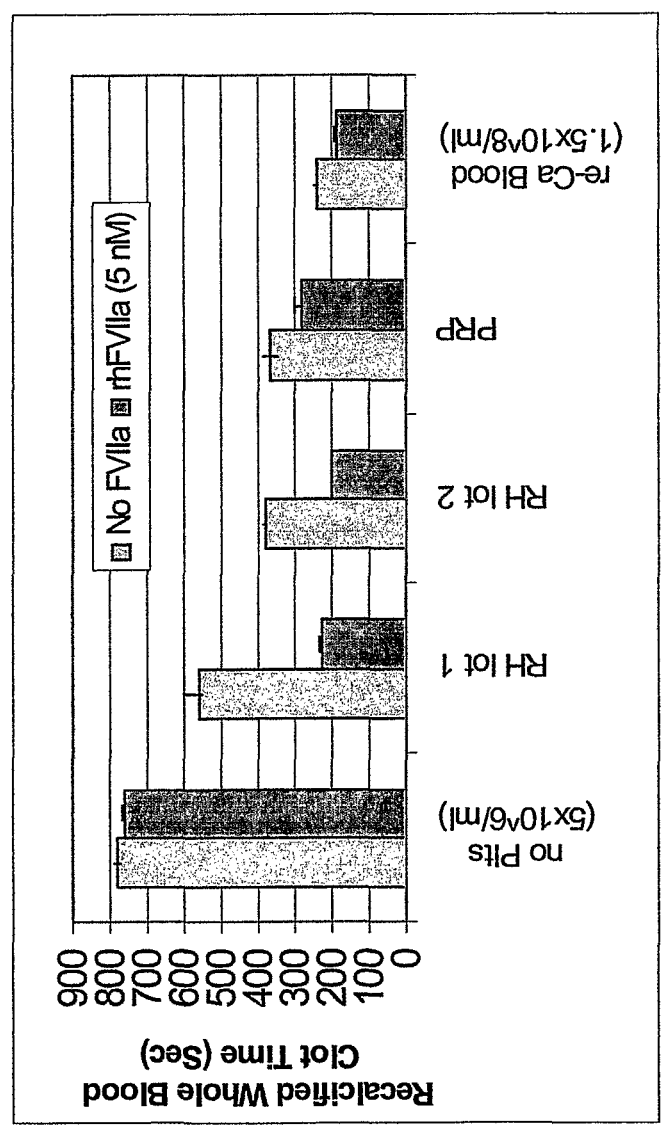
FIG. 41A shows that RHP enhance the activity of sub-pharmacologic quantities of recombinant human Factor VIIa (NovoSeven®, from Novo Nordisk).

As can be seen from FIGS. 41A, 41B, and 41C, rehydrated platelets of the invention enhanced the activity of recombinant Factor VIIa to the point where sub-pharmacologic quantities of the recombinant human Factor VIIa could effectively reduce clotting times to their normal range. Moreover, the Figure demonstrates the direct binding of a Factor FVII variant to the rehydrated platelet surface in a reaction augmented by $Ca^{2+}$. This is a significant finding in view of the cost of recombinant Factor VIIa and other clotting factors, and will no doubt reduce the cost of treating hemophilia significantly.

Example 38

Binding of Annexin-V to Platelets of the Invention

Figure 42:
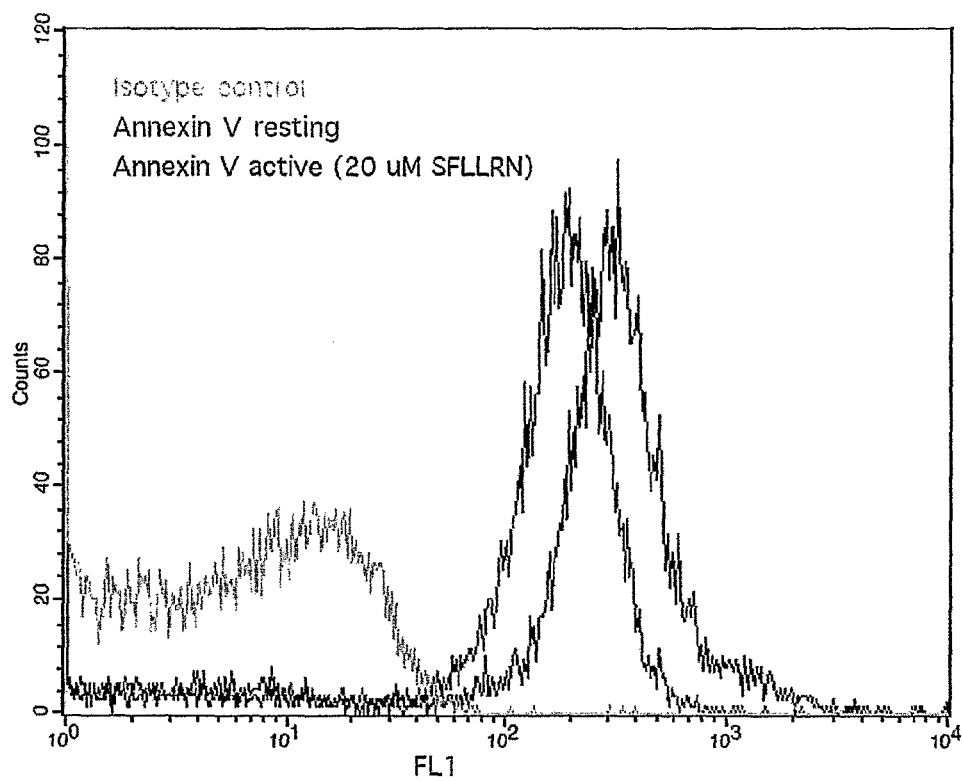
FIG. 42 shows the procoagulant properties of RHP as judged by Annexin V binding.

To further characterize the properties of the platelets of the invention, binding of Annexin-V to platelets of the invention was assayed. Annexin-V is a marker for platelet procoagulant activity because it binds to negatively charged phospholipids in a calcium-dependent manner, analogous to the vitamin K dependent clotting factors. FIG. 42 shows flow cytometry profile data demonstrating that Annexin-V binds to rehydrated platelets of the invention.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention. It is intended that the specification and Examples be considered as exemplary only, with a true scope and spirit of the invention being indicated by the following claims.

REFERENCES CITED

Christenson, J T, A Kalangos, 2004, Autologous fibrin glue reinforced by platelets in surgery of ascending aorta*: Thorac. Cardiovasc. Surg., v. 52, p. 225-229.

Gilbert, G E, P J Sims, T Wiedmer, B Furie, B C Furie, S J Shattil, 1991, Platelet-derived microparticles express high affinity receptors for factor VIII: J. Biol. Chem., v. 266, p. 17261-17268.

Giles A R, Mann K G, Nesheim M E, "A combination of factor Xa and phosphatidylcholine-phosphatidylserine vesicles bypasses factor VIII in vivo", Br. J. Haematol. 69(4): 4917, August 1988.

Hoffman, M, D M Monroe, H R Roberts, 1992, Coagulation factor IXa binding to activated platelets and platelet-derived microparticles: a flow cytometric study: Thromb. Haemost., v. 68, p. 74-78.

Holme, P A, F Brosstad, N 0 Solum, 1995, Platelet-derived microvesicles and activated platelets express factor Xa activity: Blood Coagul. Fibrinolysis, v. 6, p. 302-310.

Hrachovinova I, Cambien B, HafeziMoghadam A, Kappelmayer J, Camphausen R T, Widom A, Xia L, Kazazian H H Jr, Schaub R G, McEver R P, Wagner DD, "Interaction of P-selectin and PSGL1 generates microparticles that correct hemostasis in a mouse model of hemophilia A", Nat. Med. 9(8): 10205, August 2003.

Kirby C J, Gregoriadis G., "Preparation of liposomes containing factor VIII for oral treatment of haemophilia", J. Microencapsul. 1(1):3345, January-March 1984.

Mazzucco, L, D Medici, M Serra, R Panizza, G Rivara, S Orecchia, R Libener, E Cattana, A Levis, P G Betta, P Borzini, 2004, The use of autologous platelet gel to treat difficult-to-heal wounds: a pilot study: Transfusion, v. 44, p. 1013-1018.

Nieuwland, R, R J Berckmans, R C Rotteveel-Eijkman, K N Maquelin, K J Roozendaal, P G Jansen, K ten Have, L Eijsman, C E Hack, A Sturk, 1997, Cell-derived microparticles generated in patients during cardiopulmonary bypass are highly procoagulant: Circulation, v. 96, p. 3534-3541.

Oikarinen, K S, G K Sandor, V T Kainulainen, M Salonen-Kemppi, 2003, Augmentation of the narrow traumatized anterior alveolar ridge to facilitate dental implant placement: Dent. Traumatol., v. 19, p. 19-29.

Pierce, G F, T A Mustoe, J Lingelbach, V R Masakowski, G L Griffin, R M Senior, T F Deuel, 1989, Platelet-derived growth factor and transforming growth factor-beta enhance tissue repair activities by unique mechanisms: J. Cell Biol., v. 109, p. 429-440.

Prior, J J, D G Wallace, A Hanier, N Powers, 1999, A sprayable hemostat containing fibrillar collagen, bovine thrombin, and autologous plasma: Ann. Thorac. Surg., v. 68, p. 479-485.

Rosing, J, E M Bevers, P Comfurius, H C Hemiker, G van Dieij en, H J Weiss, R F Zwaal, 1985, Impaired factor X and prothrombin activation associated with decreased phospholipid exposure in platelets from a patient with a bleeding disorder: Blood, v. 65, p. 1557-1561.

Serebruany, V L, J V Ordonez, V V Yurovsky, P A Gurbel, 1998, Crossreactivity of Human versus Swine Platelet Surface Antigens Is Similar for Glycoproteins Ib and IIIa, but Not for the Glycoprotein IIb/IIIa Complex: J. Thromb. Thrombolysis., v. 5, p. 37-41.

Sims, P J, E M Faioni, T Wiedmer, S J Shattil, 1988, Complement proteins C5b-9 cause release of membrane vesicles from the platelet surface that are enriched in the membrane receptor for coagulation factor Va and express prothrombinase activity: J. Biol. Chem., v. 263, p. 18205-18212.

Sims, P J, S A Rollins, T Wiedmer, 1989, Regulatory control of complement on blood platelets. Modulation of platelet procoagulant responses by a membrane inhibitor of the C5b-9 complex: J. Biol. Chem., v. 264, p. 19228-19235.

Steed, D L, 1997, The role of growth factors in wound healing: Surg. Clin. North Am., v. 77, p. 575-586.

Tans, G, J Rosing, M C Thomassen, M J Heeb, R F Zwaal, J H Griffin, 1991, Comparison of anticoagulant and procoagulant activities of stimulated platelets and platelet-derived microparticles: Blood, v. 77, p. 2641-2648.

Wajon, P, J Gibson, R Calcroft, C Hughes, B Thrift, 2001, Intraoperative plateletpheresis and autologous platelet gel do not reduce chest tube drainage or allogeneic blood transfusion after reoperative coronary artery bypass graft: Anesth. Analg., v. 93, p. 536-542.

Yarovoi H V, Kufrin D, Eslin D E, Thornton M A, Haberichter S L, Shi Q, Zhu H, Camire R, Fakharzadeh S S, Kowalska M A, Wilcox D A, Sachais B S, Montgomery R R, Poncz M, "Factor VIII ectopically expressed in platelets: efficacy in hemophilia A treatment", Blood 102(12):400613, Dec. 1, 2003.

All references cited herein are incorporated herein by reference in their entireties.

The invention claimed is:

1. A process for making freeze-dried platelets, said process comprising:
   incubating isolated platelets in the presence of at least one saccharide under the following conditions: a temperature of from 20° C. to 42° C. for about 10 minutes to about 180 minutes,
   adding to the platelets at least one cryoprotectant, and lyophilizing the platelets,
   wherein the process does not include isolating the platelets between the incubating and adding steps, and
   wherein the process does not include exposing the platelets to a platelet activation inhibitor.

2. The process of claim 1, wherein the cryoprotectant is a polysugar, the process further comprising:
   heating the lyophilized platelets at a temperature of 70° C. to 80° C. for 8 to 24 hours.

3. The process of claim 2, wherein the step of adding to the platelets at least one cryoprotectant further comprises exposing the platelets to ethanol.

4. The process of claim 3, wherein the step of incubating isolated platelets in the presence of at least one saccharide comprises incubating in the presence of at least one saccharide and fibrinogen.

5. The process of claim 2, wherein the step of incubating isolated platelets in the presence of at least one saccharide comprises incubating in the presence of at least one saccharide and fibrinogen.

6. The process of claim 1, wherein the conditions for incubating comprise incubating for about 100 minutes to about 150 minutes.

7. The process of claim 1, wherein the conditions for incubating comprise incubating for about 110 minutes to about 130 minutes.

8. The process of claim 1, wherein the conditions for incubating comprise incubating for about 120 minutes.

9. The process of claim 1, wherein the conditions for incubating comprise incubating at 35° C. to 40° C.

10. The process of claim 1, wherein the conditions for incubating comprise incubating at 37° C.

11. The process of claim 1, wherein the conditions for incubating comprise incubating at 35° C. to 40° C. for 110 minutes to 130 minutes.

12. The process of claim 1, wherein the conditions for incubating comprise incubating at 37° C. for 120 minutes.

13. The process of claim 1, wherein the at least one saccharide is trehalose, sucrose, or both trehalose and sucrose.

14. The process of claim 1, wherein the at least one saccharide is trehalose.

15. The process of claim 1, wherein the at least one saccharide is sucrose.

* * * * *